(12) United States Patent
Schmidt-Dannert et al.

(10) Patent No.: US 7,604,968 B2
(45) Date of Patent: Oct. 20, 2009

(54) MICROORGANISMS FOR THE RECOMBINANT PRODUCTION OF RESVERATROL AND OTHER FLAVONOIDS

(75) Inventors: Claudia Schmidt-Dannert, Shoreview, MN (US); Kevin Watts, Minneapolis, MN (US)

(73) Assignee: Regents of the University of Minnesota, Saint Paul, MN (US)

(*) Notice: Subject to any disclaimer, the term of this patent is extended or adjusted under 35 U.S.C. 154(b) by 11 days.

(21) Appl. No.: 11/069,633

(22) Filed: Mar. 1, 2005

(65) Prior Publication Data

US 2005/0208643 A1    Sep. 22, 2005

Related U.S. Application Data

(60) Provisional application No. 60/549,077, filed on Mar. 1, 2004.

(51) Int. Cl.
| | |
|---|---|
| C12P 9/00 | (2006.01) |
| C12N 9/10 | (2006.01) |
| C12N 9/88 | (2006.01) |
| C12N 21/02 | (2006.01) |
| A61K 31/047 | (2006.01) |
| A61K 31/05 | (2006.01) |
| C07C 39/10 | (2006.01) |

(52) U.S. Cl. .............. 435/183; 435/69.1; 435/193; 435/232; 514/733; 514/734; 514/738; 568/729

(58) Field of Classification Search ............... 435/183, 435/193, 232, 69.1; 568/729; 514/733, 734, 514/738

See application file for complete search history.

(56) References Cited

U.S. PATENT DOCUMENTS

| | | | |
|---|---|---|---|
| 4,683,195 | A | 7/1987 | Mullis et al. |
| 5,349,125 | A | 9/1994 | Holton et al. |
| 5,569,832 | A | 10/1996 | Holton et al. |
| 5,639,870 | A | 6/1997 | Holton et al. |
| 5,859,334 | A | 1/1999 | Brugliera et al. |
| 5,861,487 | A | 1/1999 | Holton et al. |
| 5,948,955 | A | 9/1999 | Holton et al. |
| 6,005,167 | A | 12/1999 | Van Tunen et al. |
| 6,270,780 | B1* | 8/2001 | Carson et al. ......... 424/401 |
| 2002/0051998 | A1* | 5/2002 | Schmidt-Dannert et al. ... 435/7.1 |

FOREIGN PATENT DOCUMENTS

| | | |
|---|---|---|
| WO | WO 06/10117 | 1/2006 |
| WO | WO 06/89898 | 8/2006 |

OTHER PUBLICATIONS

Becker et al., "Metabolic engineering of *Saccharomyces cerevisiae* for the synthesis of the wine-related antioxidant resveratrol," FEMS Yeast Research 4:79-85, 2003.*

(Continued)

*Primary Examiner*—Rosanne Kosson
(74) *Attorney, Agent, or Firm*—Fish & Richardson P.C.

(57) ABSTRACT

The invention provides methods and materials related to producing flavonoids as well as other organic compounds. For example, the invention provides isolated nucleic acids, polypeptides, host cells, and methods and materials for producing flavonoids and other organic compounds.

15 Claims, 37 Drawing Sheets

OTHER PUBLICATIONS

James et al., "Expression of two *Escherichia coli* acetyl-coA carboxylase subunits is autoregulated," J Biol Chem 279(4):2520-2527, 2003.*

International Union of Biochemistry and Molecular Biology Enzyme Nomenclature, on-line database, record for phenylalanine ammonia lyase/tyrosine ammonia lyase, http://www.chem.qmul.ac.uk/iubmb/enzyme/EC4/3/1/5.html, printed on Oct. 16, 2007.*

Faulkner et al., "High-level expression of the phenylalanine ammonia lyase-encoding gene from Rhodosporidium toruloides in *Saccharomyces cerevisiae* and *Escherichia coli* using a bifunctional expression system," Gene 143(1):13-20, 1994.*

Chao and Liao, "Alteration of Growth Yield by Overexpression of Phosphoenolpyruvate Carboxylase and Phosphoenolpyruvate Carboxykinase in *Escherichia coli*," *Appl. Environ. Microbiol.*, 1993, 59(12):4261-4265.

Austin and Noel, "The chalcone synthase superfamily of type III polykedite synthases," *Nat. Prod. Rep.*, 2003, 20:79-110.

Becker and Guarente, "High-Efficiency Transformation of Yeast by Electroporation," *Meth. Enzymol.*, 1991, 194:182-187.

Burritt et al., "Filamentous Phage Display of Oligopeptide Libraries," *Anal. Biochem.*, 1996, 238:1-13.

Chen et al., "Separation and determination of flavonoids and other phenolic compounds in cranberry juice by high-performance liquid chromatography," *J. Chromatography A.*, 2001, 913:387-395.

Cusanovich and Meyer, "Photoactive Yellow Protein: A Prototypic PAS Domain Sensory Protein and Development of a Common Signaling Mechanism," *Biochemistry*, 2003, 42(17):4759-4770.

Durrens et al., "Expression of the avian *gag-myc* oncogene in *Saccharomyces cerevisiae*," *Curr. Genet.*, 1990, 18;7-12.

Guzman et al., "Tight Regulation, Modulation, and High-Level Expression by Vectors Containing the Arabinose $P_{BAD}$ Promoter," *J. Bacteriol.*, 1995, 177(14):4121-4130.

GenBank Accession No. AAB81682 dated Oct. 26, 2000, 2 pages.
GenBank Accession No. AAL16143 dated Oct. 18, 2001, 2 pages.
GenBank Accession No. AAM13084 dated Apr. 21, 2002, 2 pages.
GenBank Accession No. AAM91686 dated Sep. 18, 2002, 2 pages.
GenBank Accession No. AB013596 dated Jun. 6, 2005, 2 pages.
GenBank Accession No. AB027606 dated Dec. 21, 1999, 2 pages.
GenBank Accession No. AF112086 dated Oct. 16, 2000, 2 pages.
GenBank Accession No. AF277052 dated Jul. 18, 2000, 2 pages.
GenBank Accession No. AH009204 dated Dec. 3, 2001,4 pages.
GenBank Accession No. AY167424 dated Jan. 7, 2003, 2 pages.
GenBank Accession No. AY303128 dated Jul. 13, 2005, 3 pages.
GenBank Accession No. BAA19659 dated Feb. 24, 1998, 2 pages.
GenBank Accession No. BAA31259 dated Apr. 14, 2000, 2 pages.
GenBank Accession No. L02902 dated Sep. 24, 1993, 2 pages.
GenBank Accession No. L02904 dated Sep. 24, 1993, 2 pages.
GenBank Accession No. L02905 dated Sep. 24, 1993, 2 pages.
GenBank Accession No. M86358 dated Apr. 2, 1999, 2 pages.
GenBank Accession No. NM_119167 dated Jun. 9, 2006, 3 pages.
GenBank Accession No. NM_123645 dated Jun. 9, 2006, 2 pages.
GenBank Accession No. NP_195634 dated Jun. 9, 2006, 2 pages.
GenBank Accession No. NP_565107 dated Jun. 9, 2006, 2 pages.
GenBank Accession No. Q96323 dated May 16, 2006, 10 pages.
GenBank Accession No. Q96330 dated May 16, 2006, 3 pages.
GenBank Accession No. T51560 dated Feb. 6, 1995, 2 pages.
GenBank Accession No. U18675 dated Mar. 3, 2000, 2 pages.
GenBank Accession No. U33932 dated Mar. 1, 1996, 2 pages.
GenBank Accession No. U71080 dated May 31, 1997, 3 pages.
GenBank Accession No. X66017 dated Apr. 18, 2005, 3 pages.
GenBank Accession no. X80007 dated Apr. 18, 2005, 4 pages.
GenBank Accession No. X82366 dated Apr. 18, 2005, 2 pages.

Hughes et al., "A tandem mass spectrometric study of selected characteristic flavonoids," *Int. J. Mass Spectrom.*, 2001, 210/211:371-385.

Hull and Celenza, "Bacterial Expression and Purification of the Arabidopsis NADPH-Cytochrome P450 Reductase ATR2," *Prot. Expr. Purif.*, 2000, 18:310-315.

Hwang et al., "Production of Plant-Specific Flavanones by *Escherichia coli* Containing an Artificial Gene Cluster," *Appl. Environ. Microbiol.*, 2003, 69(5):2699-2706.

Ito et al., "Transformation of Intact Yeast Cells Treated with Alkali Cations," *J. Bacteriol.*, 1983, 153:163-168.

Justesen et al., "Quantitative analysis of flavonols, flavones, and flavanones in fruits, vegetables and beverages by high-performance liquid chromatography with photo-diode array and mass spectrometric detection," *J. Chromatography A.*, 1998, 799:101-110.

Kaneko et al., "Heterologous production of flavanones in *Escherichia coli*: potential for combinatorial biosynthesis of flavonoids in bacteria," *J. Ind. Microbiol. Biotechnol.*, 2003, 30(8):456-461.

Khlebnikov et al., "Homogeneous expression of the $P_{BAD}$ promoter in *Escherichia coli* by constitutive expression of the low-affinity high-capacity AraE transporter," *Microbiology*, 2001, 147:3241-3247.

Kyndt et al., "Characterization of a bacterial tyrosine ammonia lyase, a biosynthetic enzyme for the photoactive yellow protein," *FEBS Lett.*, 2002, 512:240-244.

Lee et al., "Biosynthesis of Structurally Novel Carotenoids in *Escherichia coli*," *Chem. Biol.*, 2003, 10:453-462.

Mol et al., "Spontaneous and Enzymic Rearrangement of Naringenin Chalcone to Flavanone," *Phytochemistry*, 1985, 24(10):2267-2269.

Paiva, "An Introduction to the Biosynthesis of Chemicals Used in Plant-Microbe Communication," J. Plant Growth Regul., 2000, 19:131-143.

Schmidt-Dannert et al., "Molecular breeding of carotenoid biosynthetic pathways," *Nat. Biotechnol.*, 2000, 18:750-753.

Weisshaar and Jenkins, "Phenylpropanoid biosynthesis and its regulation," *Curr. Opin. Plant Biol.*, 1998, 1:251-257.

Winkel-Shirley, "Flavonoid Biosynthesis. A Colorful Model for Genetics, Biochemistry, Cell Biology, and Biotechnology," *Plant Physiol.*, 2001, 126:485-493.

Yanisch-Perron et al., "Improved M13 phage cloning vectors and host strains: nucleotide sequences of the M13mp18 and pUC19 vectors," *Gene*, 1985, 33:103-119.

Beritognolo et al., "Expression of genes encoding chalcone synthase, flavanone 3-hydroxylase and dihydroflavonol 4-reductase correlates with flavanol accumulation during heartwood formation in Juglans nigra," *Tree Physiology*, 2002, 22:291-300.

ExPASy (Expected Protein Analysis System) EC Enzyme: 4.3.1-4.3.25, 1 page, 2008.

Lee et al., "Two Divergent Members of a Tobacco 4-Coumarate:Coenzyme A Ligase (4CL) Gene Family," *Plant Physiol.* (1996) 112:193-205.

Watts et al., "Discovery of A Substrate Selectivity Switch in Tyrosine Ammonia-Lyase, a Member of the Aromatic Amino Acid Lyase Family," *Chem & Biol.* 13, 1317-1326, Dec. 2006.

Dok-Go et al., "Neuroprotective effects of antioxidative flavonoids, quercetin, (+)-dihydroquercetin and quercetin 3-methyl ether, isolated from Opuntia ficus-indica var. saboten," *Brain Res.*, 2003, 965:130-136.

Lee et al., "The *Arabidopsis thaliana* 4-coumarate:CoA ligase (4CL) gene: stress and developmentally regulated expression and nucleotide sequence of its cDNA," *Plant Mol. Biol.*, 1995, 28(5):871-884.

Watts et al., "Biosynthesis of plant-specified stilbene polyketides in metabolically engineered *Escherichia coli*," *BMC Biotech.*, 2006, 6:22.

Watts et al., "Exploring recombinant flavonoid biosynthesis in metabolically engineered *Escherichia coli*," *Chembiochem.*, 2004, 5(4):500-507.

Yamaguchi et al. "Cross-reaction of chalcone synthase and stilbene synthase overexpressed in *Escherichia coli*," *FEMS Letters*, 1999, 460(3):457-461.

\* cited by examiner

Figure 3

ATGGCGCCACAAGAACAAGCAGTTTCTCAGGTGATGGAGAAACAGAGCAAC
AACAACAACAGTGACGTCATTTTCCGATCAAAGTTACCGGATATTTACATCCC
GAACCACCTATCTCTCCACGACTACATCTTCCAAAACATCTCCGAATTCGCCA
CTAAGCCTTGCCTAATCAACGGACCAACCGGCCACGTGTACACTTACTCCGA
CGTCCACGTCATCTCCCGCCAAATCGCCGCCAATTTTCACAAACTCGGCGTTA
ACCAAAACGACGTCGTCATGCTCCTCCTCCCAAACTGTCCCGAATTCGTCCTC
TCTTTCCTCGCCGCCTCCTTCCGCGGCGCAACCGCCACCGCCGCAAACCCTTT
CTTCACTCCGGCGGAGATAGCTAAACAAGCCAAAGCCTCCAACACCAAACTC
ATAATCACCGAAGCTCGTTACGTCGACAAAATCAAACCACTTCAAAACGACG
ACGGAGTAGTCATCGTCTGCATCGACGACAACGAATCCGTGCCAATCCCTGA
AGGCTGCCTCCGCTTCACCGAGTTGACTCAGTCGACAACCGAGGCATCAGAA
GTCATCGACTCGGTGGAGATTTCACCGGACGACGTGGTGGCACTACCTTACTC
CTCTGGCACGACGGGATTACCAAAAGGAGTGATGCTGACTCACAAGGGACTA
GTCACGAGCGTTGCTCAGCAAGTCGACGGCGAGAACCCGAATCTTTATTTCC
ACAGCGATGACGTCATACTCTGTGTTTTGCCCATGTTTCATATCTACGCTTTG
AACTCGATCATGTTGTGTGGTCTTAGAGTTGGTGCGGCGATTCTGATAATGCC
GAAGTTTGAGATCAATCTGCTATTGGAGCTGATCCAGAGGTGTAAAGTGACG
GTGGCTCCGATGGTTCCGCCGATTGTGTTGGCCATTGCGAAGTCTTCGGAGAC
GGAGAAGTATGATTTGAGCTCGATAAGAGTGGTGAAATCTGGTGCTGCTCCT
CTTGGTAAAGAACTTGAAGATGCCGTTAATGCCAAGTTTCCTAATGCCAAACT
CGGTCAGGGATACGGAATGACGGAAGCAGGTCCAGTGCTAGCAATGTCGTTA
GGTTTTGCAAAGGAACCTTTTCCGGTTAAGTCAGGAGCTTGTGGTACTGTTGT
AAGAAATGCTGAGATGAAAATAGTTGATCCAGACACCGGAGATTCTCTTTCG
AGGAATCAACCCGGTGAGATTTGTATTCGTGGTCACCAGATCATGAAAGGTT
ACCTCAACAATCCGGCAGCTACAGCAGAGACCATTGATAAAGACGGTTGGCT
TCATACTGGAGATATTGGATTGATCGATGACGATGACGAGCTTTTCATCGTTG
ATCGATTGAAAGAACTTATCAAGTATAAAGGTTTTCAGGTAGCTCCGGCTGA
GCTAGAGGCTTTGCTCATCGGTCATCCTGACATTACTGATGTTGCTGTTGTCG
CAATGAAAGAAGAAGCAGCTGGTGAAGTTCCTGTTGCATTTGTGGTGAAATC
GAAGGATTCGGAGTTATCAGAAGATGATGTGAAGCAATTCGTGTCGAAACAG
GTTGTGTTTTACAAGAGAATCAACAAAGTGTTCTTCACTGAATCCATTCCTAA
AGCTCCATCAGGGAAGATATTGAGGAAAGATCTGAGGGCAAAACTAGCAAA
TGGATTGTGA (SEQ ID NO:1)

Figure 4

MAPQEQAVSQVMEKQSNNNNSDVIFRSKLPDIYIPNHLSLHDYIFQNISEFATKPC
LINGPTGHVYTYSDVHVISRQIAANFHKLGVNQNDVVMLLLPNCPEFVLSFLAAS
FRGATATAANPFFTPAEIAKQAKASNTKLIITEARYVDKIKPLQNDDGVVIVCIDD
NESVPIPEGCLRFTELTQSTTEASEVIDSVEISPDDVVALPYSSGTTGLPKGVMLTH
KGLVTSVAQQVDGENPNLYFHSDDVILCVLPMFHIYALNSIMLCGLRVGAAILIM
PKFEINLLLELIQRCKVTVAPMVPPIVLAIAKSSETEKYDLSSIRVVKSGAAPLGKE
LEDAVNAKFPNAKLGQGYGMTEAGPVLAMSLGFAKEPFPVKSGACGTVVRNAE
MKIVDPDTGDSLSRNQPGEICIRGHQIMKGYLNNPAATAETIDKDGWLHTGDIGL
IDDDDELFIVDRLKELIKYKGFQVAPAELEALLIGHPDITDVAVVAMKEEAAGEV
PVAFVVKSKDSELSEDDVKQFVSKQVVFYKRINKVFFTESIPKAPSGKILRKDLR
AKLANGL (SEQ ID NO:2)

Figure 5

ATGGTGATGGCTGGTGCTTCTTCTTTGGATGAGATCAGACAGGCTCAGAGAG
CTGATGGACCTGCAGGCATCTTGGCTATTGGCACTGCTAACCCTGAGAACCAT
GTGCTTCAGGCGGAGTATCCTGACTACTACTTCCGCATCACCAACAGTGAAC
ACATGACCGACCTCAAGGAGAAGTTCAAGCGCATGTGCGACAAGTCGACAAT
TCGGAAACGTCACATGCATCTGACGGAGGAATTCCTCAAGGAAAACCCACAC
ATGTGTGCTTACATGGCTCCTTCTCTGGACACCAGACAGGACATCGTGGTGGT
CGAAGTCCCTAAGCTAGGCAAAGAAGCGGCAGTGAAGGCCATCAAGGAGTG
GGGCCAGCCCAAGTCAAAGATCACTCATGTCGTCTTCTGCACTACCTCCGGC
GTCGACATGCCTGGTGCTGACTACCAGCTCACCAAGCTTCTTGGTCTCCGTCC
TTCCGTCAAGCGTCTCATGATGTACCAGCAAGGTTGCTTCGCCGGCGGTACTG
TCCTCCGTATCGCTAAGGATCTCGCCGAGAACAACCGTGGAGCACGTGTCCT
CGTTGTCTGCTCTGAGATCACAGCCGTTACCTTCCGTGGTCCCTCTGACACCC
ACCTTGACTCCCTCGTCGGTCAGGCTCTTTTCAGTGATGGCGCCGCCGCACTC
ATTGTGGGGTCGGACCCTGACACATCTGTCGGAGAGAAACCCATCTTTGAGA
TGGTGTCTGCCGCTCAGACCATCCTTCCAGACTCTGATGGTGCCATAGACGGA
CATTTGAGGGAAGTTGGTCTCACCTTCCATCTCCTCAAGGATGTTCCCGGCCT
CATCTCCAAGAACATTGTGAAGAGTCTAGACGAAGCGTTTAAACCTTTGGGG
ATAAGTGACTGGAACTCCCTCTTCTGGATAGCCCACCCTGGAGGTCCAGCGA
TCCTAGACCAGGTGGAGATAAAGCTAGGACTAAAGGAAGAGAAGATGAGGG
CGACACGTCACGTGTTGAGCGAGTATGGAAACATGTCGAGCGCGTGCGTTCT
CTTCATACTAGACGAGATGAGGAGGAAGTCAGCTAAGGATGGTGTGGCCACG
ACAGGAGAAGGGTTGGAGTGGGGTGTCTTGTTTGGTTTCGGACCAGGTCTCA
CTGTTGAGACAGTCGTCTTGCACAGCGTTCCTCTCTAA (SEQ ID NO:3)

Figure 6

MVMAGASSLDEIRQAQRADGPAGILAIGTANPENHVLQAEYPDYYFRITNSEHM
TDLKEKFKRMCDKSTIRKRHMHLTEEFLKENPHMCAYMAPSLDTRQDIVVVEVP
KLGKEAAVKAIKEWGQPKSKITHVVFCTTSGVDMPGADYQLTKLLGLRPSVKRL
MMYQQGCFAGGTVLRIAKDLAENNRGARVLVVCSEITAVTFRGPSDTHLDSLV
GQALFSDGAAALIVGSDPDTSVGEKPIFEMVSAAQTILPDSDGAIDGHLREVGLTF
HLLKDVPGLISKNIVKSLDEAFKPLGISDWNSLFWIAHPGGPAILDQVEIKLGLKE
EKMRATRHVLSEYGNMSSACVLFILDEMRRKSAKDGVATTGEGLEWGVLFGFG
PGLTVETVVLHSVPL (SEQ ID NO:4)

Figure 7

ATGGTGTCTGTGAGTGGAATTCGCAAGGTTCAAAGAGCAGAAGGTCCTGCAA
CCGTATTAGCGATTGGCACAGCAAATCCACCAAACTGTGTTGATCAGAGCAC
ATACGCAGATTACTATTTTAGAGTAACCAATAGCGAGCACATGACCGACCTC
AAGAAGAAATTTCAGCGCATTTGTGAGAGAACACAGATCAAGAACAGACAT
ATGTATCTAACGGAAGAAATACTGAAGGAGAATCCTAACATGTGCGCATACA
AAGCACCGTCCTTGGATGCAAGGGAAGACATGATGATCAGGGAGGTACCAA
GGGTTGGAAAAGAGGCTGCAACTAAGGCAATCAAGGAATGGGGTCAGCCAA
TGTCTAAGATCACACATTTGATCTTCTGCACCACCAGCGGTGTTGCGTTGCCT
GGCGTTGATTACGAACTCATCGTACTCTTAGGGCTCGACCCAAGCGTCAAGA
GGTACATGATGTACCACCAAGGCTGCTTCGCTGGCGGCACTGTCCTTCGTTTG
GCTAAGGACTTGGCTGAAAACAACAAGGATGCTCGTGTGCTTATTGTTTGTTC
TGAAAATACTTCAGTCACTTTTCGTGGTCCTAGTGAGACAGACATGGATAGTC
TTGTAGGACAAGCATTGTTTGCCGATGGAGCTGCTGCAATTATCATTGGTTCT
GATCCTGTTCCAGAGGTTGAGAATCCTCTCTTTGAGATTGTTTCAACTGATCA
ACAACTTGTCCCTAACAGCCATGGAGCCATCGGTGGTCTCCTTCGTGAAGTTG
GACTTACATTCTATCTTAACAAGAGTGTTCCGGATATTATTTCACAAAACATC
AATGATGCACTCAGTAAAGCTTTTGATCCACTAGGTATATCTGATTATAACTC
AATATTTTGGATTGCACATCCTGGTGGACGTGCAATTTTGGACCAAGTTGAAG
AGAAGGTGAACTTGAAGCCAGAGAAGATGAAAGCCACCAGAGATGTGCTTA
GCAATTATGGTAACATGTCAAGTGCGTGTGTGTTCTTCATTATGGATTTGATG
AGAAAGAAGTCACTTGAAGCAGGACTTAAAACCACCGGAGAAGGACTTGAT
TGGGGTGTACTTTTTGGTTTTGGTCCTGGTCTCACTATTGAAACTGTTGTTCTC
CGCAGCATGGCCATATAA (SEQ ID NO:5)

Figure 8

MVSVSGIRKVQRAEGPATVLAIGTANPPNCVDQSTYADYYFRVTNSEHMTDLK
KKFQRICERTQIKNRHMYLTEEILKENPNMCAYKAPSLDAREDMMIREVPRVGK
EAATKAIKEWGQPMSKITHLIFCTTSGVALPGVDYELIVLLGLDPSVKRYMMYH
QGCFAGGTVLRLAKDLAENNKDARVLIVCSENTSVTFRGPSETDMDSLVGQALF
ADGAAAIIIGSDPVPEVENPLFEIVSTDQQLVPNSHGAIGGLLREVGLTFYLNKSV
PDIISQNINDALSKAFDPLGISDYNSIFWIAHPGGRAILDQVEEKVNLKPEKMKAT
RDVLSNYGNMSSACVFFIMDLMRKKSLEAGLKTTGEGLDWGVLFGFGPGLTIET
VVLRSMAI (SEQ ID NO:6)

Figure 9

ATGAAGCCAATGCTCGCCATGAGCCCCCCGAAGCCGGCCGTCGAGCTGGATC
GCCACATCGATCTGGACCAGGCCCATGCCGTGGCGAGCGGCGGCGCGCGGAT
TGTCCTTGCCCCTCCGGCGCGCGACCGGTGCCGTGCGTCCGAAGCGCGGCTC
GGCGCTGTCATCCGCGAGGCGCGCCATGTCTACGGACTGACAACCGGCTTCG
GTCCCCTTGCGAACCGCCTGATCTCAGGTGAGAATGTCCGAACGCTGCAGGC
CAATCTTGTCCATCATCTGGCCAGCGGCGTGGGACCGGTGCTTGACTGGACG
ACGGCGCGCGCCATGGTTCTGGCGCGTCTGGTGTCGATCGCTCAGGGAGCCT
CCGGTGCCAGCGAGGGGACCATCGCTCGCCTGATCGACCTGCTCAATTCCGA
GCTCGCTCCGGCCGTTCCCAGCCGCGGCACGGTGGGCGCGTCGGGTGACCTG
ACACCGCTTGCGCATATGGTGCTCTGCCTCCAGGGCCGGGGAGACTTCCTGG
ACCGGGACGGGACGCGGCTTGACGGCGCAGAAGGGCTCCGGCGCGGACGGC
TGCAACCGCTCGATCTCTCCCATCGCGATGCACTGGCGCTGGTCAACGGGAC
CTCCGCCATGACCGGGATCGCGCTGGTGAATGCTCACGCCTGCCGCCATCTC
GGCAACTGGGCGGTGGCGTTGACGGCCCTGCTTGCGGAATGTCTGAGAGGCC
GGACCGAGGCATGGGCCGCGGCACTGTCCGACCTGCGGCCGCATCCCGGACA
GAAGGACGCCGCAGCGAGGCTGCGCGCCCGCGTGGACGGCAGCGCGCGGGT
GGTCCGGCACGTCATTGCCGAGCGGAGGCTCGACGCCGGCGATATCGGGACG
GAGCCGGAGGCGGGGCAGGATGCCTACAGCCTGCGCTGCGCTCCGCAGGTTC
TCGGGGCGGGCTTCGACACGCTCGCATGGCATGACCGGGTGCTGACGATCGA
GCTGAACGCGGTGACCGACAATCCGGTGTTTCCGCCCGATGGCAGCGTGCCC
GCCCTGCACGGGGGCAATTTCATGGGCCAGCATGTGGCGCTGACGTCCGATG
CGCTCGCCACGGCCGTCACCGTTCTGGCGGGCCTTGCGGAGCGCCAGATTGC
ACGTCTGACAGATGAAAGGCTGAACCGTGGGCTGCCCCCCTTCCTCCACCGG
GGCCCCGCCGGGTTGAATTCCGGCTTCATGGGCGCACAGGTGACGGCGACCG
CGCTCCTGGCCGAGATGCGAGCCACGGGACCTGCCTCGATCCATTCGATCTC
CACGAACGCCGCCAATCAGGATGTGGTCTCGCTTGGGACCATCGCCGCGCGC
CTCTGCCGCGAGAAGATCGACCGTTGGGCGGAGATCCTTGCGATCCTCGCTC
TCTGTCTTGCACAAGCTGCGGAGCTGCGCTGCGGCAGCGGCCTAGACGGGGT
GTCTCCCGCGGGGAAGAAGCTGGTGCAGGCCCTGCGCGAGCAGTTCCCGCCG
CTTGAGACGGACCGGCCCCTGGGACAGGAAATTGCCGCGCTTGCTACGCACC
TCTTGCAGCAATCTCCCGTCTGA (SEQ ID NO:7)

Figure 10

MKPMLAMSPPKPAVELDRHIDLDQAHAVASGGARIVLAPPARDRCRASEARLG
AVIREARHVYGLTTGFGPLANRLISGENVRTLQANLVHHLASGVGPVLDWTTAR
AMVLARLVSIAQGASGASEGTIARLIDLLNSELAPAVPSRGTVGASGDLTPLAHM
VLCLQGRGDFLDRDGTRLDGAEGLRRGRLQPLDLSHRDALALVNGTSAMTGIAL
VNAHACRHLGNWAVALTALLAECLRGRTEAWAAALSDLRPHPGQKDAAARLR
ARVDGSARVVRHVIAERRLDAGDIGTEPEAGQDAYSLRCAPQVLGAGFDTLAW
HDRVLTIELNAVTDNPVFPPDGSVPALHGGNFMGQHVALTSDALATAVTVLAGL
AERQIARLTDERLNRGLPPFLHRGPAGLNSGFMGAQVTATALLAEMRATGPASI
HSISTNAANQDVVSLGTIAARLCREKIDRWAEILAILALCLAQAAELRCGSGLDG
VSPAGKKLVQALREQFPPLETDRPLGQEIAALATHLLQQSPV (SEQ ID NO:8)

Figure 11

ATGGAGATTAACGGGGCACACAAGAGCAACGGAGGAGGAGTGGACGCTATG
TTATGCGGCGGAGACATCAAGACAAAGAACATGGTGATCAACGCGGAGGAT
CCTCTCAACTGGGGAGCTGCAGCGGAGCAAATGAAAGGTAGCCATTTGGATG
AAGTGAAGAGAATGGTTGCTGAGTTTAGGAAGCCAGTTGTGAATCTTGGTGG
TGAGACTCTGACCATTGGACAAGTGGCTGCGATCTCAACTATTGGTAACAGT
GTGAAGGTGGAGCTATCGGAGACAGCTAGAGCCGGTGTGAATGCTAGTAGTG
ATTGGGTTATGGAGAGTATGAACAAAGGCACTGATAGTTATGGTGTTACTAC
TGGTTTTGGTGCTACTTCTCATCGGAGAACCAAAAACGGTGTCGCACTTCAGA
AGGAACTTATTAGATTCCTTAACGCCGGAATATTCGGAAGCACGAAAGAAAC
AAGCCACACATTGCCACACTCCGCCACAAGAGCCGCCATGCTTGTACGAATC
AACACTCTCCTCCAAGGATTTTCCGGTATCCGATTTGAGATTCTCGAAGCAAT
TACCAGTTTCCTCAACAACAACATCACTCCATCTCTCCCCCTCCGTGGTACAA
TCACCGCCTCCGGAGATCTCGTTCCTCTCTCCTACATCGCCGGACTTCTCACC
GGTCGTCCCAATTCCAAAGCTACTGGTCCCAACGGTGAAGCTTTAACAGCAG
AGGAAGCTTTCAAATTAGCAGGAATCAGCTCCGGATTCTTTGATCTCCAGCCT
AAGGAAGGTCTCGCGCTAGTCAATGGCACGGCGGTTGGATCTGGAATGGCGT
CAATGGTGTTATTCGAAACGAATGTTCTCTCTGTTTGGCTGAGATTTGTCG
GCGGTTTTCGCAGAGGTGATGAGTGGTAAGCCTGAGTTCACCGATCATCTCA
CTCACAGACTTAAACATCATCCCGGTCAAATCGAAGCGGCGGCGATAATGGA
GCATATCCTCGACGGAAGCTCGTACATGAAATTAGCTCAGAAGCTTCACGAG
ATGGATCCGTTACAGAAACCTAAACAAGATCGTTACGCTCTTCGTACTTCTCC
TCAATGGTTAGGTCCTCAAATCGAAGTGATCCGTTACGCAACGAAATCGATC
GAGCGTGAGATTAACTCCGTCAACGATAATCCGTTGATCGATGTTTCGAGGA
ACAAGGCGATTCACGGTGGTAACTTCCAAGGAACACCAATCGGAGTTTCAAT
GGATAACACGAGATTGGCGATAGCAGCGATTGGTAAACTCATGTTTGCTCAA
TTCTCAGAGCTTGTGAATGATTTCTACAACAATGGTTTACCCTCGAATCTAAC
CGCTTCGAGGAATCCAAGTTTGGATTATGGATTCAAGGGAGCTGAGATTGCA
ATGGCTTCTTATTGTTCAGAGCTTCAATACTTAGCTAATCCTGTGACTAGCCA
TGTTCAATCAGCAGAGCAACATAACCAAGATGTCAACTCTTTGGGACTAATC
TCGTCTCGCAAAACTTCTGAAGCTGTTGATATTCAAGCTTATGTCAACAAC
GTTCCTCGTTGCGATTTGTCAAGCTGTGGATTTGAGACATTTGGAGGAGAATT
TGAGACAGACTGTGAAGAACACTGTCTCTCAAGTGGCGAAGAAAGTTCTTAC
TACTGGAGTCAATGGTGAGCTTCATCCTTCTCGCTTCTGCGAAAAGGATTTAC
TCAAAGTTGTAGACCGTGAACAAGTCTACACATACGCGGATGATCCTTGTAG
CGCAACGTACCCGTTGATTCAGAAGCTGAGACAAGTTATTGTTGACCATGCTT
TGATCAATGGTGAGAGTGAGAAGAATGCAGTGACTTCAATCTTCCATAAGAT
TGGAGCTTTCGAGGAGGAGCTTAAGGCAGTGCTACCGAAAGAAGTGGAAGC
AGCAAGAGCAGCCTACGATAACGGAACATCGGCTATCCCGAACAGGATCAA
GGAATGTAGGTCGTATCCATTGTATAGATTCGTGAGGGAAGAGCTTGGAACA
GAGCTTTTGACCGGAGAGAAAGTGACGTCGCCTGGAGAAGAGTTCGACAAG
GTTTTCACGGCGATTTGTGAAGGTAAAATCATTGATCCGATGATGGAATGTCT
CAACGAGTGGAACGGAGCTCCCATTCCAATATGTTAA (SEQ ID NO:9)

Figure 12

MEINGAHKSNGGGVDAMLCGGDIKTKNMVINAEDPLNWGAAAEQMKGSHLDE
VKRMVAEFRKPVVNLGGETLTIGQVAAISTIGNSVKVELSETARAGVNASSDWV
MESMNKGTDSYGVTTGFGATSHRRTKNGVALQKELIRFLNAGIFGSTKETSHTLP
HSATRAAMLVRINTLLQGFSGIRFEILEAITSFLNNNITPSLPLRGTITASGDLVPLS
YIAGLLTGRPNSKATGPNGEALTAEEAFKLAGISSGFFDLQPKEGLALVNGTAVG
SGMASMVLFETNVLSVLAEILSAVFAEVMSGKPEFTDHLTHRLKHHPGQIEAAAI
MEHILDGSSYMKLAQKLHEMDPLQKPKQDRYALRTSPQWLGPQIEVIRYATKSI
EREINSVNDNPLIDVSRNKAIHGGNFQGTPIGVSMDNTRLAIAAIGKLMFAQFSEL
VNDFYNNGLPSNLTASRNPSLDYGFKGAEIAMASYCSELQYLANPVTSHVQSAE
QHNQDVNSLGLISSRKTSEAVDILKLMSTTFLVAICQAVDLRHLEENLRQTVKNT
VSQVAKKVLTTGVNGELHPSRFCEKDLLKVVDREQVYTYADDPCSATYPLIQKL
RQVIVDHALINGESEKNAVTSIFHKIGAFEEELKAVLPKEVEAARAAYDNGTSAIP
NRIKECRSYPLYRFVREELGTELLTGEKVTSPGEEFDKVFTAICEGKIIDPMMECL
NEWNGAPIPIC (SEQ ID NO:10)

Figure 13

ATGGACCTCCTCTTGCTGGAGAAGTCTCTAATCGCCGTCTTCGTGGCGGTGAT
TCTCGCCACGGTGATTTCAAAGCTCCGCGGCAAGAAATTGAAGCTACCTCCA
GGTCCTATACCAATTCCGATCTTCGGAAACTGGCTTCAAGTAGGAGATGATCT
CAACCACCGTAATCTCGTCGATTACGCTAAGAAATTCGGCGATCTCTTCCTCC
TCCGTATGGGTCAGCGTAACCTAGTCGTCGTCTCTTCACCGGATCTAACCAAG
GAAGTGCTCCACACACAAGGCGTTGAGTTTGGATCTAGAACGAGAAACGTCG
TGTTCGACATTTTCACCGGGAAAGGTCAAGATATGGTGTTCACTGTTTACGGC
GAGCATTGGAGGAAGATGAGAAGAATCATGACGGTTCCTTTCTTCACCAACA
AAGTTGTTCAACAGAATCGTGAAGGTTGGGAGTTTGAAGCAGCTAGTGTTGT
TGAAGATGTTAAGAAGAATCCAGATTCTGCTACGAAAGGAATCGTGTTGAGG
AAACGTTTGCAATTGATGATGTATAACAATATGTTCCGTATCATGTTCGATAG
AAGATTTGAGAGTGAGGATGATCCTCTTTTCCTTAGGCTTAAGGCTTTGAATG
GTGAGAGAAGTCGATTAGCTCAGAGCTTTGAGTATAACTATGGAGATTTCAT
TCCTATCCTTAGACCATTCCTCAGAGGCTATTTGAAGATTTGTCAAGATGTGA
AAGATCGAAGAATCGCTCTTTTCAAGAAGTACTTTGTTGATGAGAGGAAGCA
AATTGCGAGTTCTAAGCCTACAGGTAGTGAAGGATTGAAATGTGCCATTGAT
CACATCCTTGAAGCTGAGCAGAAGGGAGAAATCAACGAGGACAATGTTCTTT
ACATCGTCGAGAACATCAATGTCGCCGCGATTGAGACAACATTGTGGTCTAT
CGAGTGGGGAATTGCAGAGCTAGTGAACCATCCTGAAATCCAGAGTAAGCTA
AGGAACGAACTCGACACGGTTCTTGGACCGGGTGTGCAAGTCACCGAGCCTG
ATCTTCACAAACTTCCATACCTTCAAGCTGTGGTTAAGGAGACTCTTCGTCTG
AGAATGGCGATTCCTCTCCTCGTGCCTCACATGAACCTCCATGATGCGAAGCT
CGCTGGCTACGATATCCAGCAGAAAGCAAAATCCTTGTTAATGCTTGGTGG
CTAGCAAACAACCCCAACAGCTGGAAGAAGCCTGAAGAGTTTAGACCAGAG
AGGTTCTTTGAAGAAGAATCGCACGTGGAAGCTAACGGAAATGACTTCAGGT
ATGTGCCGTTTGGTGTTGGACGTAGAAGCTGTCCCGGGATTATATTGGCATTA
CCTATTTTGGGGATCACCATTGGTAGGATGGTCCAGAACTTCGAGCTTCTTCC
TCCTCCAGGACAGTCTAAAGTGGATACTAGTGAGAAGGTGGACAATTCAGC
TTGCACATCCTTAACCACTCCATAATCGTTATGAAACCAAGGAACTGTTAA
(SEQ ID NO:11)

Figure 14

MDLLLLEKSLIAVFVAVILATVISKLRGKKLKLPPGPIPIPIFGNWLQVGDDLNHR
NLVDYAKKFGDLFLLRMGQRNLVVVSSPDLTKEVLHTQGVEFGSRTRNVVFDIF
TGKGQDMVFTVYGEHWRKMRRIMTVPFFTNKVVQQNREGWEFEAASVVEDVK
KNPDSATKGIVLRKRLQLMMYNNMFRIMFDRRFESEDDPLFLRLKALNGERSRL
AQSFEYNYGDFIPILRPFLRGYLKICQDVKDRRIALFKKYFVDERKQIASSKPTGS
EGLKCAIDHILEAEQKGEINEDNVLYIVENINVAAIETTLWSIEWGIAELVNHPEIQ
SKLRNELDTVLGPGVQVTEPDLHKLPYLQAVVKETLRLRMAIPLLVPHMNLHDA
KLAGYDIPAESKILVNAWWLANNPNSWKKPEEFRPERFFEEESHVEANGNDFRY
VPFGVGRRSCPGIILALPILGITIGRMVQNFELLPPPGQSKVDTSEKGGQFSLHILN
HSIIVMKPRNC (SEQ ID NO:12)

Figure 15

ATGTCCTCTTCTTCTTCTTCGTCAACCTCCATGATCGATCTCATGGCAGCAATC
ATCAAAGGAGAGCCTGTAATTGTCTCCGACCCAGCTAATGCCTCCGCTTACG
AGTCCGTAGCTGCTGAATTATCCTCTATGCTTATAGAGAATCGTCAATTCGCC
ATGATTGTTACCACTTCCATTGCTGTTCTTATTGGTTGCATCGTTATGCTCGTT
TGGAGGAGATCCGGTTCTGGGAATTCAAAACGTGTCGAGCCTCTTAAGCCTTT
GGTTATTAAGCCTCGTGAGGAAGAGATTGATGATGGGCGTAAGAAAGTTACC
ATCTTTTTCGGTACACAAACTGGTACTGCTGAAGGTTTTGCAAAGGCTTTAGG
AGAAGAAGCTAAAGCAAGATATGAAAGACCAGATTCAAAATCGTTGATTTG
GATGATTACGCGGCTGATGATGATGAGTATGAGGAGAAATTGAAGAAAGAG
GATGTGGCTTTCTTCTTCTTAGCCACATATGGAGATGGTGAGCCTACCGACAA
TGCAGCGAGATTCTACAAATGGTTCACCGAGGGGAATGACAGAGGAGAATG
GCTTAAGAACTTGAAGTATGGAGTGTTTGGATTAGGAAACAGACAATATGAG
CATTTTAATAAGGTTGCCAAAGTTGTAGATGACATTCTTGTCGAACAAGGTGC
ACAGCGTCTTGTACAAGTTGGTCTTGGAGATGATGACCAGTGTATTGAAGAT
GACTTACCGCTTGGCGAGAAGCATTGTGGCCCGAGCTTGATACAATACTGA
GGGAAGAAGGGGATACAGCTGTTGCCACACCATACACTGCAGCTGTGTTAGA
ATACAGAGTTTCTATTCACGACTCTGAAGATGCCAAATTCAATGATATAAAC
ATGGCAAATGGGAATGGTTACACTGTGTTTGATGCTCAACATCCTTACAAAG
CAAATGTCGCTGTTAAAAGGGAGCTTCATACTCCCGAGTCTGATCGTTCTTGT
ATCCATTTGGAATTTGACATTGCTGGAAGTGGACTTACGTATGAAACTGGAG
ATCATGTTGGTGTACTTTGTGATAACTTAAGTGAAACTGTAGATGAAGCTCTT
AGATTGCTGGATATGTCACCTGATACTTATTTCTCACTTCACGCTGAAAAAGA
AGACGGCACACCAATCAGCAGCTCACTGCCTCCTCCCTTCCCACCTTGCAACT
TGAGAACAGCGCTTACACGATATGCATGTCTTTGAGTTCTCCAAAGAAGTCT
GCTTTAGTTGCGTTGGCTGCTCATGCATCTGATCCTACCGAAGCAGAACGATT
AAAACACCTTGCTTCACCTGCTGGAAAGGATGAATATTCAAAGTGGGTAGTA
GAGAGTCAAAGAAGTCTACTTGAGGTGATGGCCGAGTTTCCTTCAGCCAAGC
CACCACTTGGTGTCTTCTTCGCTGGAGTTGCTCCAAGGTTGCAGCCTAGGTTC
TATTCGATATCATCATCGCCCAAGATTGCTGAAACTAGAATTCACGTCACATG
TGCACTGGTTTATGAGAAAATGCCAACTGGCAGGATTCATAAGGGAGTGTGT
TCCACTTGGATGAAGAATGCTGTGCCTTACGAGAAGAGTGAAAACTGTTCCT
CGGCGCCGATATTTGTTAGGCAATCCAACTTCAAGCTTCCTTCTGATTCTAAG
GTACCGATCATCATGATCGGTCCAGGGACTGGATTAGCTCCATTCAGAGGAT
TCCTTCAGGAAAGACTAGCGTTGGTAGAATCTGGTGTTGAACTTGGGCCATC
AGTTTTGTTCTTTGGATGCAGAAACCGTAGAATGGATTTCATCTACGAGGAAG
AGCTCCAGCGATTTGTTGAGAGTGGTGCTCTCGCAGAGCTAAGTGTCGCCTTC
TCTCGTGAAGGACCCACCAAAGAATACGTACAGCACAAGATGATGGACAAG
GCTTCTGATATCTGGAATATGATCTCTCAAGGAGCTTATTTATATGTTTGTGG
TGACGCCAAAGGCATGGCAAGAGATGTTCACAGATCTCTCCACACAATAGCT
CAAGAACAGGGGTCAATGGATTCAACTAAAGCAGAGGGCTTCGTGAAGAAT
CTGCAAACGAGTGGAAGATATCTTAGAGATGTATGGTAA (SEQ ID NO:13)

Figure 16

MSSSSSSSTSMIDLMAAIIKGEPVIVSDPANASAYESVAAELSSMLIENRQFAMIVT
TSIAVLIGCIVMLVWRRSGSGNSKRVEPLKPLVIKPREEEIDDGRKKVTIFFGTQT
GTAEGFAKALGEEAKARYEKTRFKIVDLDDYAADDDEYEEKLKKEDVAFFFLAT
YGDGEPTDNAARFYKWFTEGNDRGEWLKNLKYGVFGLGNRQYEHFNKVAKVV
DDILVEQGAQRLVQVGLGDDDQCIEDDFTAWREALWPELDTILREEGDTAVATP
YTAAVLEYRVSIHDSEDAKFNDINMANGNGYTVFDAQHPYKANVAVKRELHTP
ESDRSCIHLEFDIAGSGLTYETGDHVGVLCDNLSETVDEALRLLDMSPDTYFSLH
AEKEDGTPISSSLPPPFPPCNLRTALTRYACLLSSPKKSALVALAAHASDPTEAER
LKHLASPAGKDEYSKWVVESQRSLLEVMAEFPSAKPPLGVFFAGVAPRLQPRFY
SISSSPKIAETRIHVTCALVYEKMPTGRIHKGVCSTWMKNAVPYEKSENCSSAPIF
VRQSNFKLPSDSKVPIIMIGPGTGLAPFRGFLQERLALVESGVELGPSVLFFGCRN
RRMDFIYEEELQRFVESGALAELSVAFSREGPTKEYVQHKMMDKASDIWNMISQ
GAYLYVCGDAKGMARDVHRSLHTIAQEQGSMDSTKAEGFVKNLQTSGRYLRD
VW (SEQ ID NO:14)

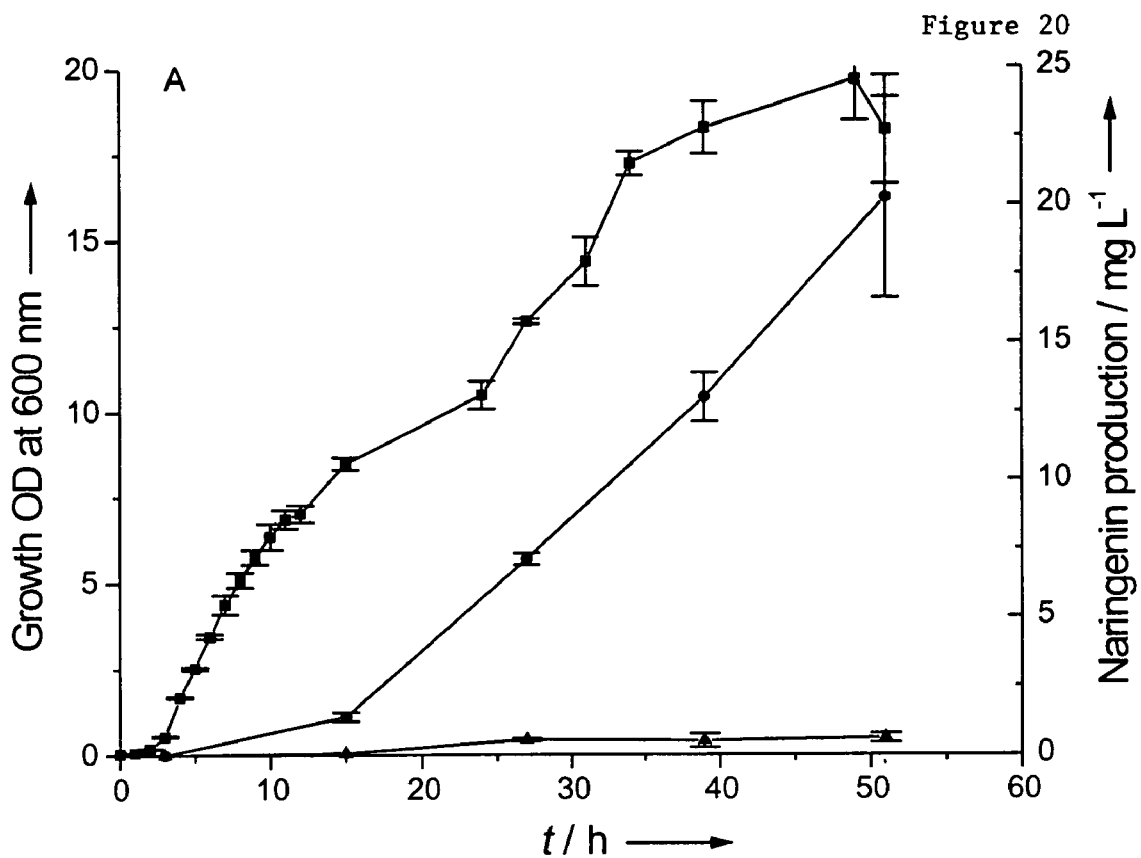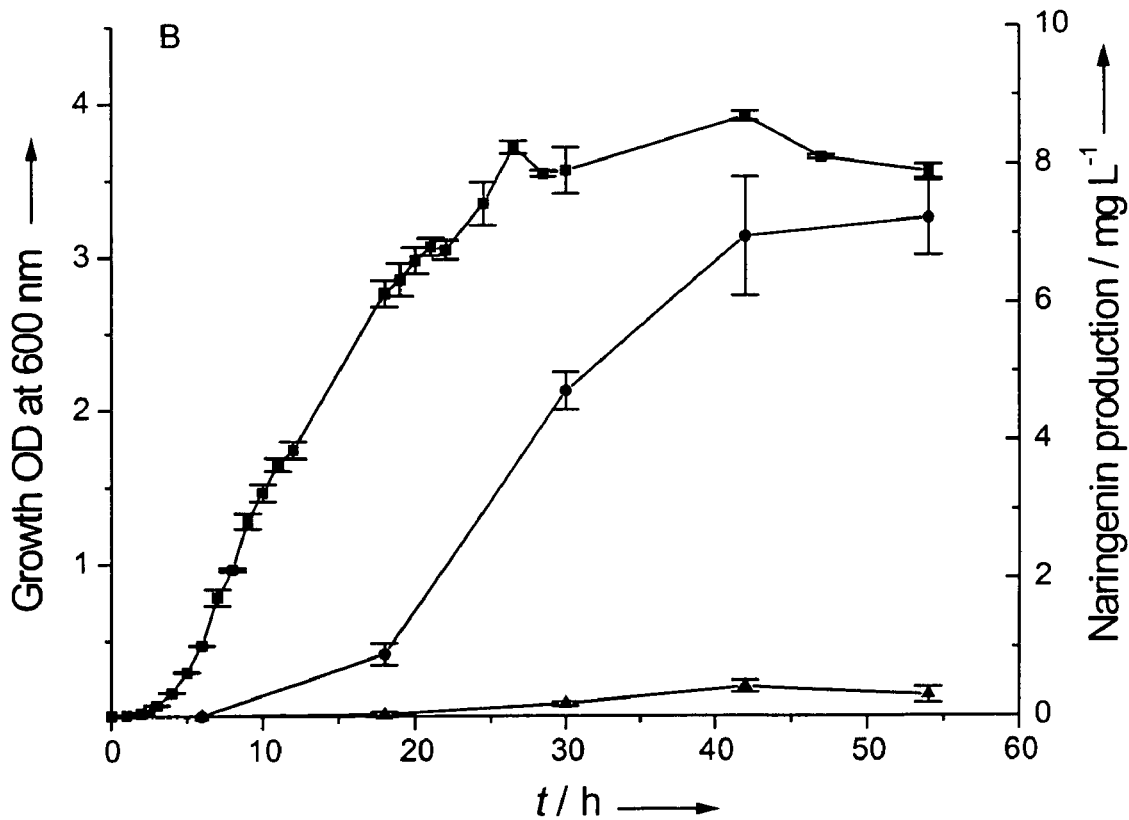
Figure 20

Figure 22

ATGGTTAGTGTGTCTGAAATTCGCAATGCTCAAAGGGCAGAAGGCCCTGCAA
CCATTTTAGCCATTGGCACTGCAAACCCAGCCAATTGTGTTGAACAAAGCAC
ATATCCTGATTTCTACTTCAAAATCACAAATAGTGAACACAAGACTGAACTC
AAAGAGAAATTCCAACGCATGTGTGATAAATCTATGATCAAGAGGAGATATA
TGTACCTAACAGAGGAGATTTTGAAAGAGAATCCTAGTGTTTGTGAATACAT
GGCACCTTCATTGGATGCTAGGCAAGACATGGTGGTGGTAGAGGTACCTAGA
CTAGGGAAGGAGGCTGCAGTGAAGGCCATAAAAGAATGGGGTCAACCAAAG
TCAAAGATTACTCACTTGATCGTTTGCACCACAAGTGGTGTAGACATGCCTGG
AGCTGATTACCAACTCACAAAACTCTTAGGTCTTCGCCCATATGTGAAAAGGT
ATATGATGTACCAACAAGGTTGCTTTGCAGGAGGCACGGTCCTTCGTTTGGCT
AAAGATTTAGCTGAAAACAACAAAGGTGCTCGTGTGTTGGTTGTCTGTTCTGA
AGTCACTGCAGTCACATTTCGCGGCCCTAGTGATACTCACTTGGACAGCCTTG
TTGGACAAGCACTATTTGGAGATGGAGCTGCTGCACTAATTGTTGGTTCAGAT
CCAGTACCAGAAATTGAGAAACCAATATTTGAGATGGTTTGGACTGCACAAA
CAATTGCTCCAGATAGTGAAGGAGCCATTGATGGTCACCTTCGTGAAGCTGG
ACTAACATTTCACCTTCTTAAAGATGTTCCTGGGATTGTTTCAAAGAACATCA
ATAAAGCATTGGTTGAGGCTTTTGAACCATTAGGAATTTCTGATTACAATTCA
ATCTTTTGGATTGCACACCCTGGTGGACCTGCAATTCTAGATCAAGTTGAGCA
AAAGTTAGCCTTAAAGCCTGAAAAGATGAAAGCCACCAGAGAAGTGCTTAGT
GAATATGGAAATATGTCAAGTGCCTGTGTTTGTTTATCTTAGATGAAATGAG
AAAGAAGTCAGCTCAAGATGGATTGAAGACCACAGGAGAAGGACTTGAATT
TGGTGTTTTATTTGGCTTTGGACCGGGTCTTACCATTGAAACTGTTGTTTTGCG
AAGTATCGCTATATG (SEQ ID NO:15)

MVSVSEIRNAQRAEGPATILAIGTANPANCVEQSTYPDFYFKITNSEHKTELKEKF
QRMCDKSMIKRRYMYLTEEILKENPSVCEYMAPSLDARQDMVVVEVPRLGKEA
AVKAIKEWGQPKSKITHLIVCTTSGVDMPGADYQLTKLLGLRPYVKRYMMYQQ
GCFAGGTVLRLAKDLAENNKGARVLVVCSEVTAVTFRGPSDTHLDSLVGQALF
GDGAAALIVGSDPVPEIEKPIFEMVWTAQTIAPDSEGAIDGHLREAGLTFHLLKD
VPGIVSKNINKALVEAFEPLGISDYNSIFWIAHPGGPAILDQVEQKLALKPEKMKA
TREVLSEYGNMSSACVLFILDEMRKKSAQDGLKTTGEGLEFGVLFGFGPGLTIET
VVLRSIAI (SEQ ID NO:16)

Figure 23

ATGGTGAGTGTATCTGAAATTCGCAAGGCTCAAAGGGCAGAAGGTCCTGCAA
CCATATTGGCCATTGGCACTGCAAATCCAGCAAACTGTGTTGAACAAAGCAC
ATATCCTGATTTTTACTTTAAAATCACAAATAGCGAACACAAAACTGAGCTCA
AAGAAAAATTTCAACGCATGTGTGACAAATCCATGATCAAAAGAAGATACAT
GTATCTAACAGAGGAGATTTTAAAAGAGAATCCTAATGTTTGTGAATACATG
GCACCTTCATTGGATGCTAGACAAGACATGGTGGTGGTAGAAGTACCTAGAC
TAGGGAAGGAGGCTGCAGTGAAGGCTATAAAAGAATGGGGTCAACCAAAGT
CAAAGATTACTCACTTAATCGTTTGCACCACAAGCGGTGTAGACATGCCTGG
GGCCGATTATCAACTCACTAAACTCTTAGGTCTTCGTCCATATGTAAAAGAT
ACATGATGTACCAGCAAGGTTGTTTTGCAGGTGGCACGGTACTTCGTTTGGCT
AAGGATTTGGCTGAGAACAACAAAGGTGCTCGTGTGTTAGTTGTTTGTTCTGA
AGTCACTGCAGTCACATTTCGTGGTCCCAGTGATACACACTTGGACAGTCTTG
TTGGACAAGCACTATTTGGAGATGGAGCAGCTGCACTTATTGTTGGGTCTGAT
CCGGTACCAGAAATTGAAAAACCTATATTTGAGATGATTTGGACAGCACAAA
CAATTGCTCCTGATAGTGAAGGTGCCATTGATGGTCATCTTCGTGAAGCTGGG
TTAACATTTCACCTTCTTAAAGATGTTCCTGGGATTGTGTCAAAAAATATAAA
TAAAGCATTAGTTGAGGCTTTCCAACCATTGGGAATCTCTGATTACAACTCAA
TCTTTTGGATTGCACACCCTGGTGGACCTGCAATTTTAGACCAAGTAGAGCAA
AAGTTAGCCTTAAAGCCCGAAAAGATGAGAGCCACACGGGAGGTGCTAAGT
GAATATGGAAATATGTCAAGTGCATGTGTATTGTTTATCTTGGATGAAATGAG
AAAGAAATCAACTCAAAATGGTTTGAAGACAACCGGAGAAGGGCATGAATG
GGGTGTGCTATTCGGCTTTGGACCAGGACTTACCATTGAGACTGTTGTCTTGC
GCAGTGTAGCTATATAA (SEQ ID NO:17)

MVSVSEIRKAQRAEGPATILAIGTANPANCVEQSTYPDFYFKITNSEHKTELKEKF
QRMCDKSMIKRRYMYLTEEILKENPNVCEYMAPSLDARQDMVVVEVPRLGKEA
AVKAIKEWGQPKSKITHLIVCTTSGVDMPGADYQLTKLLGLRPYVKRYMMYQQ
GCFAGGTVLRLAKDLAENNKGARVLVVCSEVTAVTFRGPSDTHLDSLVGQALF
GDGAAALIVGSDPVPEIEKPIFEMIWTAQTIAPDSEGAIDGHLREAGLTFHLLKDV
PGIVSKNINKALVEAFQPLGISDYNSIFWIAHPGGPAILDQVEQKLALKPEKMRAT
REVLSEYGNMSSACVLFILDEMRKKSTQNGLKTTGEGHEWGVLFGFGPGLTIET
VVLRSVAI (SEQ ID NO:18)

Figure 24

ATGGTGACTGTGGAGGAGATTCGTAAGGCTCAACGTTCCAATGGCCCTGCCA
CTATCTTGGCTTTTGGCACTGCCACTCCTTCTCACTGTGTCACTCAAGCTGAAT
ATCCTGATTACTACTTTCGTATCACCAACAGTGAGCACATGACTGACCTTAAG
GAAAAATTCAAGCGCATGTGTGAAAAATCGATGATAAAGAAACGTTACATGC
ACATAACAGAAGAATTTCTGAAAGAGAATCCAAACATGTGTGCATACATGGC
ACCATCACTAGACGCAAGACAAGATTTAGTGGTAGTGGAAGTACCAAAGCTA
GGTAAAGATGCTGCAAAAAAGCCATAGCTGAATGGGGTCAACCAAAATCC
AAAATCACCCACGTAGTTTTCTGCACAACTTCTGGTGTAGACATGCCGGGTGC
CGATTACCAACTCACTAAACTCTTAGGCCTAAAACCATCTGTCAAACGTCTCA
TGATGTATCAACAAGGTTGTTTCGCAGGCGGCACAGTTCTCCGCTTAGCGAA
AGATCTTGCTGAGAATAACAAAAATGCAAGAGTTCTTGTTGTTTGTTCTGAAA
TCACTGCAGTTACTTTCCGTGGTCCATCAGATACTCATTTAGATTCACTTGTA
GGACAGGCGCTCTTCGGTGATGGAGCCGCAGCAATGATTATTGGTGCGGATC
CAGATTTAACCGTGGAGCGTCCGATTTTTGAGATTGTCTCGGCTGCTCAGACT
ATTCTTCCTGATTCTGATGGCGCGATTGACGGACATCTCCGTGAAGTTGGGCT
CACTTTTCATCTTCTCAAAGATGTTCCTGGAATTATCTCAAAGAATATTGAAA
AGAGTTTGGTTGAGGCTTTTGCACCAATTGGAATAAGTGATTGGAATTCGATC
TTTTGGGTTGCACATCCAGGTGGACCGGCTATTTTAGACCAGGTTGAAGAAA
AACTCCGTCTTAAGGAGGAGAAACTCCGGTCCACCCGGCACGTGCTTAGTGA
ATATGGAAATATGTCGAGTGCTTGTGTTTGTTTATTTGGATGAAATGAGAA
AGAGGTCTAAGGAGGAAGGAAAGATTACAACCGGTGAAGGGTTGGAATGGG
GTGTTTTGTTTGGGTTTGGACCGGGTTTAACCGTTGAGACAGTTGTGCTTCAT
AGTGTTCCGGTTCAGGGTTAA (SEQ ID NO:19)

MVTVEEIRKAQRSNGPATILAFGTATPSHCVTQAEYPDYYFRITNSEHMTDLKEK
FKRMCEKSMIKKRYMHITEEFLKENPNMCAYMAPSLDARQDLVVVEVPKLGKD
AAKKAIAEWGQPKSKITHVVFCTTSGVDMPGADYQLTKLLGLKPSVKRLMMYQ
QGCFAGGTVLRLAKDLAENNKNARVLVVCSEITAVTFRGPSDTHLDSLVGQALF
GDGAAAMIIGADPDLTVERPIFEIVSAAQTILPDSDGAIDGHLREVGLTFHLLKDV
PGIISKNIEKSLVEAFAPIGISDWNSIFWVAHPGGPAILDQVEEKLRLKEEKLRSTR
HVLSEYGNMSSACVLFILDEMRKRSKEEGKITTGEGLEWGVLFGFGPGLTVETV
VLHSVPVQG (SEQ ID NO:20)

Figure 25

ATGGTGAGTGTATCTGAAATTCGCAAGGCTCAGAGGGCAGAAGGCCCTGCCA
CCATCATGGCCATTGGCACTGCAAATCCAGCCAACTGTGTTGAACAAAGCAC
ATATCCTGATTTTTACTTCAAAATCACAAACAGTGAGCACAAAGTTGAACTTA
AGAAAAATTTCAACGCATGTGTGATAAATCCATGATCAAGAGGAGATACAT
GTATCTTACCGAAGAAATTTTGAAAGAAATCCAAGTGTATGTGAATACATG
GCACCGTCATTGGATGCTAGGCAGGACATGGTGGTGGTAGAAGTACCTAGAC
TAGGAAAGGAGGCTGCAGTGAAAGCTATAAAAGAATGGGGCCAACCAAAAT
CAAAGATTACACACTTGATCTTTTGCACCACAAGTGGTGTAGACATGCCTGGC
GCTGATTACCAACTCACCAAACTCTTAGGTCTTCGTCCATATGTGAAGAGGTA
TATGATGTACCAACAAGGATGTTTTGCAGGTGGGACGGTGCTTCGTTTGGCCA
AGGACTTGGCTGAGAACAATAAAGGTGCTCGTGTGTTGGTTGTTTGTTCTGAA
GTTACTGCAGTGACATTCCGTGGTCCTAGTGATACTCATTTGGACAGTCTTGT
TGGACAAGCACTATTTGGAGATGGTGCTGCTGCACTCATTGTTGGTTCTGACC
CAATACCAGAAATTGAGAAACCTATATTTGAGATGGTTTGGACTGCACAAAC
AATTGCTCCAGACAGTGAGGGAGCCATTGATGGTCACCTTCGTGAAGCTGGT
CTAACATTTCACCTTCTTAAAGATGTTCCTGGGATTGTTTCAAAGAACATTGA
TAAAGCATTGGTCGAGGCTTTCCAACCATTAAACATCTCTGATTATAATTCAA
TCTTCTGGATTGCTCACCCAGGTGGACCCGCAATTCTAGACCAAGTTGAAGA
AAAGTTAGGCTTAAAACCTGAAAAAATGAAGGCCACTAGGGAAGTACTTAGT
GAATATGGTAACATGTCAAGCGCATGTGTATTGTTCATCTTGGATGAGATGA
GAAAGAAATCGGCTCAAGAGGGACTTAAAACCACAGGTGAAGGCCTTGACT
GGGGTGTGTTGTTTGGCTTTGGACCTGGACTCACCATTGAAACAGTTGTTCTC
CATAGCGTGGCTATATA (SEQ ID NO:21)

MVSVSEIRKAQRAEGPATIMAIGTANPANCVEQSTYPDFYFKITNSEHKVELKEK
FQRMCDKSMIKRRYMYLTEEILKENPSVCEYMAPSLDARQDMVVVEVPRLGKE
AAVKAIKEWGQPKSKITHLIFCTTSGVDMPGADYQLTKLLGLRPYVKRYMMYQ
QGCFAGGTVLRLAKDLAENNKGARVLVVCSEVTAVTFRGPSDTHLDSLVGQAL
FGDGAAALIVGSDPIPEIEKPIFEMVWTAQTIAPDSEGAIDGHLREAGLTFHLLKD
VPGIVSKNIDKALVEAFQPLNISDYNSIFWIAHPGGPAILDQVEEKLGLKPEKMKA
TREVLSEYGNMSSACVLFILDEMRKKSAQEGLKTTGEGLDWGVLFGFGPGLTIET
VVLHSVAI (SEQ ID NO:22)

Figure 26

ATGGTGACATTTGATGAGATCCGCCAGGCACAGAGGGCTGATGGCCCTGCCA
CCGTGTTGGCAATCGGCACTGCAACTCCTCAAAACTGCGTGGACCAGAGCAC
ATACCCTGACTACTATTTCCGCATCACAAACAGTGAACATAAGACTGAGCTC
AAAGAAAAATTTCAGCGCATGTGTGATAAGTCAATGATCAAGAAGAGATACA
TGTACTTGACAGAAGAGATCCTGAAAGAGAATCCAAGTGTATGCGAGTACAT
GGCACCTTCATTGGATGCAAGACAAGACATGGTGGTTGTGGAGGTACCAAGA
CTAGGAAAGAGGCAGCAACAAAGGCCATCAAGGAATGGGGTCAACCTAAG
TCCAAGATTACCCACCTCATCTTTTGCACCACCAGTGGCGTGGACATGCCCGG
TGCCGACTATCAGCTGACAAAGCTCTTGGGCCTTCGTCCATATGTGAAGCGTT
ACATGATGTACCAACAAGGTTGTTTTGCTGGTGGCACGGTGCTTCGTTTGGCT
AAAGACTTGGCTGAAAACAACAAAGGTGCTCGTGTGTTGGTAGTTTGTTCAG
AGATAACTGCAGTTACTTTCCGTGGACCCAGTGACACTCATCTTGATAGCCTT
GTGGGGCAAGCATTGTTTGGAGATGGTGCAGCAGCTGTGATCGTAGGTTCAG
ACCCATTACCACAAGTTGAGAAACCCTTGTTTGAATTGGTATGGACTGCACA
AACGATCCTTCCAGATAGTGAAGGAGCAATTGACGGTCACCTTCGTGAAGTC
GGGCTTACATTCCATCTCCTCAAGGATGTTCCTGGTCTTATCTCAAAGAACAT
TGAGAAAGCTCTTGCTGAGGCCTTTCAACCTTTAGGTATCTCTGATTACAATT
CCATCTTTTGGATCGCACACCCTGGTGGACCAGCAATTCTGGACCAAGTGGA
AGCCAAATTAAGCTTAAAGCCAGAGAAAATGCAAGCCACTCGACATGTGCTT
AGCGAGTATGGTAACATGTCAAGTGCATGTGTGTTATTCATCTTGGATGAGAT
GAGGAGGAAGTCAAAAGAAGACGGACTTGCCACAACAGGCGAGGGGCTGGA
ATGGGGTGTCCTATTTGGTTTCGGGCCCGGACTCACTGTTGAGACTGTAGTGC
TCCACAGTGTTGCCACTTA (SEQ ID NO:23)

MVTFDEIRQAQRADGPATVLAIGTATPQNCVDQSTYPDYYFRITNSEHKTELKEK
FQRMCDKSMIKKRYMYLTEEILKENPSVCEYMAPSLDARQDMVVVEVPRLGKE
AATKAIKEWGQPKSKITHLIFCTTSGVDMPGADYQLTKLLGLRPYVKRYMMYQ
QGCFAGGTVLRLAKDLAENNKGARVLVVCSEITAVTFRGPSDTHLDSLVGQALF
GDGAAAVIVGSDPLPQVEKPLFELVWTAQTILPDSEGAIDGHLREVGLTFHLLKD
VPGLISKNIEKALAEAFQPLGISDYNSIFWIAHPGGPAILDQVEAKLSLKPEKMQA
TRHVLSEYGNMSSACVLFILDEMRRKSKEDGLATTGEGLEWGVLFGFGPGLTVE
TVVLHSVAT (SEQ ID NO:24)

Figure 29

ATGGCACCGGAGGAGTCCAGGCATGCTGAAACTGCAGTTAACAGAGCCGCC
ACCGTCCTGGCCATCGGCACTGCCAACCCGCCAAACTGCTACTATCAAGCGG
ACTTTCCTGACTTCTACTTCCGTGCCACCAACAGCGACCACCTCACGCACCTC
AAGCAAAAATTTAAGCGCATTTGTGAGAAATCGATGATTGAAAAACGTTATC
TCCATTTGACGGAAGAAATTCTCAAGGAGAATCCAAATATTGCTTCCTTCGAG
GCGCCATCATTGGATGTAAGACATAACATTCAAGTGAAAGAAGTGGTGCTGC
TCGGAAAAGAGGCAGCTTTGAAGGCCATCAATGAGTGGGGCCAACCCAAGTC
AAAGATCACGCGCCTCATTGTGTGTTGTATTGCCGGCGTTGACATGCCCGGCG
CAGACTATCAACTCACTAAACTCCTTGGCTTACAACTTTCTGTTAAGCGATTT
ATGTTTTACCACCTAGGATGCTATGCCGGTGGCACCGTCCTTCGCCTTGCGAA
GGACATAGCAGAAAACAACAAGGAAGCTCGTGTTCTCATCGTTCGCTCTGAG
ATGACGCCAATCTGTTTCCGTGGGCCATCCGAAACCCACATAGACTCCATGG
TAGGGCAAGCAATATTTGGTGACGGTGCTGCGGCTGTTATAGTTGGTGCAAA
TCCCGACCTATCCATCGAAAGGCCGATTTCGAGTTGATTCTACATCCCAAA
CTATCATACCTGAATCCGATGGTGCGATTGAGGGACATTTGCTTGAAGTTGGA
CTCAGTTTCCAACTCTACCAGACTGTTCCCTCATTAATCTCTAATTGTATCGAA
ACTTGTCTTTCAAAGGCTTTCACACCTCTTAACATTAGTGATTGGAACTCACT
ATTCTGGATTGCACACCCTGGTGGCCGTGCTATCCTTGACGATATCGAGGCTA
CTGTTGGTCTCAAGAAGGAGAAACTTAAGGCAACAAGACAAGTTTTGAACGA
CTATGGGAACATGTCAAGTGCTTGCGTATTTTCATCATGGATGAGATGAGGA
AGAAGTCGCTCGCAAACGGTCAAGTAACCACTGGAGAAGGACTCAAGTGGG
GTGTTCTTTTTGGGTTCGGGCCAGGTGTTACTGTGGAAACTGTGGTTCTAAGC
AGTGTGCCGCTAATTACCTGA (SEQ ID NO:25)

MAPEESRHAETAVNRAATVLAIGTANPPNCYYQADFPDFYFRATNSDHLTHLKQ
KFKRICEKSMIEKRYLHLTEEILKENPNIASFEAPSLDVRHNIQVKEVVLLGKEAA
LKAINEWGQPKSKITRLIVCCIAGVDMPGADYQLTKLLGLQLSVKRFMFYHLGC
YAGGTVLRLAKDIAENNKEARVLIVRSEMTPICFRGPSETHIDSMVGQAIFGDGA
AAVIVGANPDLSIERPIFELISTSQTIIPESDGAIEGHLLEVGLSFQLYQTVPSLISNCI
ETCLSKAFTPLNISDWNSLFWIAHPGGRAILDDIEATVGLKKEKLKATRQVLNDY
GNMSSACVFFIMDEMRKKSLANGQVTTGEGLKWGVLFGFGPGVTVETVVLSSV
PLIT (SEQ ID NO:26)

Figure 30

ATGACCACCGGTGAGGCCAGCCTTATGAAGAATGGTCCAGCATCCCGCGCG
CAGAGAGGAGAGAGCAGATGGTCCGGCTACTGAGCTAGCCATTGGCACCG
CCAATCCGTCCAATGTGTTCGATCAGGAAACGTATCCTGACTTTTACTTCGAC
GTTACCAACAACACTGATAAGCCTGAGTTGAAGGCCAAATTCCAGCGCATGT
GTAACAGTCTGGAATCCAAAAAGGTACATGTGCTTCACGGAGGAGACGTTGA
AGGCCAACCTAGTATGGTGTTTATTGGCAGAATTCTTCTTGACGTGAGACAAG
GACGTCGTAGCAGAGCAAGTGCTAAGTTGGCAAAAGAGGCATCCCTGAAGG
CTTTGAGAGAGTGGGGTCAGCCCAATTCCAAGATCACCCATTTGGTCTTCTGC
ACCACCGCTCCAGTTACCCTGCCTGGAGTAGATGCTGCCCTGATACAGAGTTT
AGGCCTGAATCCTTCGGTCAAGCGGGTTCTGCTTTACATGCAGGGCTGCTTCG
CAGGTGGTACGGTGCTCAGACATGCCAAGGACCTTGCAGAGAACAACAGAG
GCGCCCGAGTCTTAGTGGTGTGCAGCGAGACGACCGCAGTCACATTCCGCGG
GCCGCATGAAAATCATCTTGACAATCTAGTAGGACAAGCCTTGTTTGCGGAT
GGGGCATCGGCCCTGATAGTAGGCTCGGATCCAATTTCAGATCTTGAGAAGC
CGTGGTTTGAGATAAGGTGGGCAGGATCGTACTTGATTCCGGAAAGCGGCCA
AGCTATTGCAGGGCAGCTCAAGGAAGTGGGGCTTGAATTTCATCTGACCAGA
GATGTCTCTGGGTTGGTCTCGAAGAACATTGTAACGATTCTAAACGAGGCCTT
CGAGGGAACAGGAATAACCGACTGGAATGATATATTTATCATTCCACATCCC
GGAGGCCCAGCCATTCTCGACGTAATACAGGACAGACTGAAGCTGCAACCTG
AGAAGCTACAAGCGAGCCGCCATGTGCTGGCCGAATTCGGCAACATGTCCAG
CGCTACTGTTCATTTAGTTTGGACCAGATGAGAAGGTCTTCTGTAGAGAAGG
GGTGTTCCACCACCGGTGAGGGCTACGAATTGGGAATTCTACTTGGGTTAGG
ACCGGGAATGACAGTGGAATCTATCCTCTTGAAGAGTGTACCCACATGGACA
GTAGCTTCATAG (SEQ ID NO:27)

MTTGEASLMKNGPASRARREERADGPATELAIGTANPSNVFDQETYPDFYFDVT
NNTDKPELKAKFQRMCNSLESKKVHVLHGGDVEGQPSMVFIGRILLDVRQGRRS
RASAKLAKEASLKALREWGQPNSKITHLVFCTTAPVTLPGVDAALIQSLGLNPSV
KRVLLYMQGCFAGGTVLRHAKDLAENNRGARVLVVCSETTAVTFRGPHENHLD
NLVGQALFADGASALIVGSDPISDLEKPWFEIRWAGSYLIPESGQAIAGQLKEVGL
EFHLTRDVSGLVSKNIVTILNEAFEGTGITDWNDIFIIPHPGGPAILDVIQDRLKLQP
EKLQASRHVLAEFGNMSSATVHFSLDQMRRSSVEKGCSTTGEGYELGILLGLGP
GMTVESIL LKSVPTWTVAS (SEQ ID NO:28)

Figure 31

ATGGCTTCAGTTGAGGAATTTAGAAACGCTCAACGTGCCAAGGGTCCGGCCA
CTATCCTAGCCATTGGCACAGCTACTCCTGACCACTGTGTCTACCAGTCTGAT
TATGCTGATTACTATTTCAGGGTCACTAAGAGCGAGCACATGACTGAGTTGA
AGAAGAAGTTCAATCGCATATGTGACAAATCAATGATCAAGAAGCGTTACAT
TCACTTGACCGAAGAAATGCTTGAGGAGCACCCAAACATTGGTGCTTATATG
GCTCCATCTCTTAACATACGCCAAGAGATTATCACTGCTGAGGTACCTAGACT
TGGTAGGGATGCAGCATTGAAGGCTCTTAAAGAGTGGGGCCAACCAAAGTCC
AAGATCACCCATCTTGTATTTTGTACAACCTCCGGTGTAGAAATGCCCGGTGC
GGATTACAAACTCGCTAATCTCTTAGGTCTTGAAACATCGGTTAGAAGGGTG
ATGTTGTACCATCAAGGGTGCTATGCAGGTGGAACTGTCCTTCGAACTGCTAA
GGATCTTGCAGAAAATAATGCAGGAGCACGAGTTCTTGTGGTGTGCTCTGAG
ATCACTGTTGTTACATTCCGTGGCCCTTCCGAAGATGCTTTGGACTCTTTAGTT
GGCCAAGCCCTTTTTGGTGATGGGTCTTCAGCTGTGATTGTGGATCAGATCC
AGATGTCTCGATTGAACGACCACTCTTCCAACTTGTTTCAGCAGCCCAAACAT
TTATTCCTAATTCAGCAGGAGCCATTGCCGGAAACTTACGTGAGGTGGGGCT
CACCTTTCATTTGTGGCCCAATGTGCCTACTTTGATTTCTGAGAACATAGAGA
AATGCTTGACCCAGGCTTTTGACCCACTTGGTATTAGCGATTGGAACTCGTTA
TTTTGGATTGCTCACCCAGGTGGCCCTGCAATTCTCGATGCAGTTGAAGCAAA
ACTCAATTTAGAGAAAAAGAAACTCGAAGCAACTAGGCATGTGTTAAGTGAG
TACGGTAACATGTCAAGTGCATGTGTTGTTTATTCTGGATGAGATGAGAAA
GAAATCCTTGAAGGGGGAAAAGGCTACCACAGGTGAAGGATTGGATTGGGG
AGTATTATTTGGTTTTGGGCCGGGCTTGACCATCGAAACTGTTGTGCTGCATA
GCGTTCCTACAGTTACAAATTAA (SEQ ID NO:29)

MASVEEFRNAQRAKGPATILAIGTATPDHCVYQSDYADYYFRVTKSEHMTELKK
KFNRICDKSMIKKRYIHLTEEMLEEHPNIGAYMAPSLNIRQEIITAEVPRLGRDAA
LKALKEWGQPKSKITHLVFCTTSGVEMPGADYKLANLLGLETSVRRVMLYHQG
CYAGGTVLRTAKDLAENNAGARVLVVCSEITVVTFRGPSEDALDSLVGQALFGD
GSSAVIVGSDPDVSIERPLFQLVSAAQTFIPNSAGAIAGNLREVGLTFHLWPNVPT
LISENIEKCLTQAFDPLGISDWNSLFWIAHPGGPAILDAVEAKLNLEKKKLEATRH
VLSEYGNMSSACVLFILDEMRKKSLKGEKATTGEGLDWGVLFGFGPGLTIETVV
LHSVPTVTN (SEQ ID NO:30)

Figure 32

ATGCAACCTGTCGAGCCACTGGCGCCGCTGCCGGCGCGCCTGCTCGAGCGCCTGGTG
CATTGGGCCCAGGTGCGCCCGGACACCACTTTCATCGCGGCACGCCAGGCAGACGGT
GCCTGGCGTTCGATCAGCTACGTGCAGATGCTCGCCGATGTGCGCACCATCGCCGCC
AACTTGCTAGGACTGGGCCTCAGTGCCGAGCGCCCGCTGGCGCTGCTTTCCGGCAAC
GACATCGAACACCTGCAAATCGCCCTCGGCGCCATGTATGCCGGTATTGCCTATTGC
CCGGTGTCGCCGGCCTACGCGCTGTTGTCGCAAGACTTCGCCAAGTTGCGCCATGTCT
GCGAGGTGCTCACCCCCGGAGTGGTCTTCGTCAGCGACAGCCAGCCGTTCCAGCGCG
CCTTCGAGGCGGTGCTGGACGATTCGGTCGGCGTGATCAGCGTGCGTGGCCAGGTCG
CAGGTCGCCCCCATATAAGCTTCGACAGCCTGTTGCAACCGGGTGACCTGGCGGCGG
CCGATGCGGCTTTCGCCGCCACCGGGCCGGACACCATCGCCAAATTCCTCTTCACCTC
GGGCTCGACCAAGCTGCCCAAGGCGGTGATCACCACCCAGCGCATGCTGTGCGCCAA
TCAGCAGATGCTTCTGCAGACTTTTCCGACGTTCGCCGAGGAGCCGCCGGTGCTGGT
GGACTGGCTGCCGTGGAACCACACGTTCGGCGGTAGCCACAACCTCGGCATCGTGCT
TTACAACGGGGGCAGTTTCTACCTGGACGCCGGCAAGCCGACCCCGCAAGGCTTCGC
CGAGACCTTGCGCAATCTGCGCGAGATTTCCCCCACGGCCTACCTCACCGTACCCAA
GGGCTGGGAGGAACTGGTCAAGGCACTGGAGCAGGACCCCGCGCTACGCGAGGTGT
TCTTTGCCCGCATCAAGCTGTTCTTCTTTGCCGCCGCAGGCCTGTCGCAAAGCGTCTG
GGACCGGCTGGACCGCATTGCCGAGCAACACTGTGGCGAACGCATCCGCATGATGG
CCGGCCTTGGCATGACCGAAGCCTCGCCATCGTGCACCTTCACCACCGGGCCTTTGTC
GATGGCCGGCTATGTCGGGCTGCCGGCACCTGGCTGCGAAGTGAAGCTGGTGCCGGT
GGGCGACAAGCTCGAGGCGCGCTTCCGTGGCCCGCATATCATGCCGGGCTACTGGCG
CTCGCCGCAGCAGACCGCCGAGGCGTTCGACGAGGAGGGCTTCTACTGTTCGGGCGA
CGCGTTGAAGCTGGCCGATGCCAGGCAGCCCGAGCTTGGCCTGATGTTCGATGGCCG
TATCGCTGAGGACTTCAAACTTTCGTCCGGGGTATTCGTCAGTGTCGGGCCGCTGCGC
AACCGCGCAGTGCTGGAGGGCTCGCCTTACGTACAGGACATCGTGGTCACCGCGCCG
GACCGTGAATGCCTGGGCCTGCTGGTGTTCCCGCGTCTGCCCGAGTGTCGGCGCCTG
GCCGGGCTGGCAGAGGATGCCAGCGATGCGCGGGTGCTGGCCAACGACACCGTGCG
CAGTTGGTTCGCTGACTGGCTGGAGCGCTTGAACCGCGATGCCCAAGGCAACGCCAG
CCGTATCGAATGGCTGTCGCTGCTGGCCGAGCCGCCGTCGATCGACGCCGGTGAAAT
CACCGACAAGGGCTCGATCAATCAGCGCGCCGTGCTGCAGCGGCGCGCCGCTCAGGT
CGAGGCGCTGTACCGTGGCGAAGACCCCGACGCATTGCACGCCAAGGTGCGGCCT
(SEQ ID NO:31)

MQPVEPLAPLPARLLERLVHWAQVRPDTTFIAARQADGAWRSISYVQMLADVRTIAANL
LGLGLSAERPLALLSGNDIEHLQIALGAMYAGIAYCPVSPAYALLSQDFAKLRHVCEVLT
PGVVFVSDSQPFQRAFEAVLDDSVGVISVRGQVAGRPHISFDSLLQPGDLAAADAAFAAT
GPDTIAKFLFTSGSTKLPKAVITTQRMLCANQQMLLQTFPTFAEEPPVLVDWLPWNHTFG
GSHNLGIVLYNGGSFYLDAGKPTPQGFAETLRNLREISPTAYLTVPKGWEELVKALEQDP
ALREVFFARIKLFFFAAAGLSQSVWDRLDRIAEQHCGERIRMMAGLGMTEASPSCTFTTG
PLSMAGYVGLPAPGCEVKLVPVGDKLEARFRGPHIMPGYWRSPQQTAEAFDEEGFYCSG
DALKLADARQPELGLMFDGRIAEDFKLSSGVFVSVGPLRNRAVLEGSPYVQDIVVTAPD
RECLGLLVFPRLPECRRLAGLAEDASDARVLANDTVRSWFADWLERLNRDAQGNASRIE
WLSLLAEPPSIDAGEITDKGSINQRAVLQRRAAQVEALYRGEDPDALHAKVRP(SEQ ID
NO:32)

Figure 33

ATGACAGCCGAGGGGCCTCTGGCACCGGAAGATCGGGTGCTCGACCGGGAG
GCGATCGGGCGCCTCTGCGTCTCCCTGATCGCGGCCGAGCAGCAGGACCTGC
TGCGGGAAGGGCGCGTCGGTCATCATCAGATGATCGGCGCGCCTCCTGAC
GGCAGGGCATCCGTCGCCCGACGACCTGCTGATCGACGAAGACACGCTGGGG
CTCGACAGTCTGCTCATGCTCTCGCTCGTCACCCGCGTGGCGGGCTTCTTCCA
TCTGTCGGATTCGAACACCGAGGATTATCTTCTCGTGCGACGCCGTCTGGGAG
AGTGGGTGGATCTGATCGATCATCACCACACCCTGATGGGGCCGAAGGCGCG
CTTCACCTTCGCGACCTCGGGAAGCACCGCAGGACCGAAGCCCGTGACCCAC
AGCGCCGCGGCACTGCTCTCGGAAGGGCAGGCCATCGCGAAGATCCTCACGG
AGCGGCCTCCCGAGGTGCGCCGCGTCCTCTCCTGCGTTCCGGCCCACCACATC
TACGGCTTCCTCTGGTCCTGCCTGTTTCCCTCCCGCCGCGGTCTCGAGGCGAA
GCAACTGGCGAACCTGTCCGCTTCCGGCATCATGCGGCACGCGCGCTCCGGC
GATCTGGTGGTGGGCACGCCCTTCATCTGGGAGCAGTTCGCGGATCTCGACT
ACCGGCTGCCCGGCGACGTGGTCGGGGTGACGTCCGGCGCACCCTCGACGGC
CGAGACATGGCGCTGCGCCTCTGCGCTCGGCCCGGCACGGATGCTGGACATC
TATGGCTCGACCGAAACCGGGGGCATCGGCTGGCGCGAGCGCCGGGACGAC
CCTTTCCGAACCCTGCCCGATCTCGCCTGCTTTCATGACACGTTGAGCAGGCT
GGGCCGGCGGCTGGACCTGCAGGACGAGATCGCCTGGGACAAGGACGGCGG
CTTCACGATTCTCGGCCGCAAGGACGAGATCCTGCAGGTCGCGGGATCGAAC
GTCTCTCCTGCCGCGGTCCGAGATATCCTGCTCCGGAACCCGCGTGTCCGGGA
TGCGGCGGTGCGGCTCGACGGACGCAGGCTGAAGGCCGTGATCTCTGTGGCG
GAGGGCGCTGACGAGGCAGAGATCGAGATCGAACTGCGCGCGACTGCGGCG
CGGCATCTTCCGGCACCTGCCAGGCCGGACCGGTTCCTTTTCGCGACGGAACT
CCCGCGCACGGGTGCAGGGAAATTGGCGGACTGGTAG (SEQ ID NO:33)

MTAEGPLAPEDRVLDREAIGRLCVSLIAAEQQDLLREGRVGHHQMIGARLLTAG
HPSPDDLLIDEDTLGLDSLLMLSLVTRVAGFFHLSDSNTEDYLLVRRRLGEWVDL
IDHHHTLMGPKARFTFATSGSTAGPKPVTHSAAALLSEGQAIAKILTERPPEVRRV
LSCVPAHHIYGFLWSCLFPSRRGLEAKQLANLSASGIMRHARSGDLVVGTPFIWE
QFADLDYRLPGDVVGVTSGAPSTAETWRCASALGPARMLDIYGSTETGGIGWRE
RRDDPFRTLPDLACFHDTLSRLGRRLDLQDEIAWDKDGGFTILC ∶KDEILQVAGS
NVSPAAVRDILLRNPRVRDAAVRLDGRRLKAVISVAEGADEAEIEIELRATAARH
LPAPARPDRFLFATELPRTGAGKLADW (SEQ ID NO:34)

Figure 34

GTGTTCCGCAGCGAGTACGCAGACGTCCCGCCCGTCGACCTGCCCATCCACG
ACGCCGTGCTCGGCGGGGCCGCCGCCTTCGGGAGCACCCCGGCGCTGATCGA
CGGCACCGACGGCACCACCCTCACCTACGAGCAGGTGGACCGGTTCCACCGG
CGCGTCGCCGCCGCCCTCGCCGAGACCGGCGTGCGCAAGGGCGACGTCCTCG
CCCTGCACAGCCCCAACACCGTCGCCTTCCCCCTGGCCTTCTACGCCGCCACC
CGCGCGGGCGCCTCCGTCACCACGGTGCATCCGCTCGCGACGGCGGAGGAGT
TCGCCAAGCAGCTGAAGGACAGCGCGGCCCGCTGGATCGTCACCGTCTCACC
GCTCCTGTCCACCGCCCGCCGGGCCGCCGAACTCGCGGGCGGCGTCCAGGAG
ATCCTGGTCTGCGACAGCGCGCCCGGTCACCGCTCCCTCGTCGACATGCTGGC
CTCGACCGCGCCCGAACCGTCCGTCGCCATCGACCCGGCCGAGGACGTCGCC
GCCCTGCCGTACTCCTCGGGCACCACCGGCACCCCCAAGGGCGTCATGCTCA
CACACCGGCAGATCGCCACCAACCTCGCCCAGCTCGAACCGTCGATGCCGTC
CGCGCCCGGCGACCGCGTCCTCGCCGTGCTGCCGTTCTTCCACATCTACGGCC
TGACCGCCCTGATGAACGCCCCGCTCCGGCTCGGCGCCACCGTCGTGGTCCT
GCCCCGCTTCGACCTGGAGCAGTTCCTCGCCGCCATCCAGAACCACCGCATC
ACCAGCCTGTACGTCGCCCCGCCGATCGTCCTGGCCCTCGCCAAACACCCCCT
GGTCGCCGACTACGACCTCTCCTCGCTGAGGTACATCGTCAGCGCCGCCGCC
CCGCTCGACGCGCGTCTCGCCGCCGCCTGCTCGCAGCGGCTCGGCCTGCCGC
CCGTCGGCCAGGCCTACGGCATGACCGAACTGTCCCCGGGCACCCACGTCGT
CCCCCTGGACGCGATGGCCGACGCGCCGCCCGGCACCGTCGGCAGGCTCATC
GCGGGCACCGAGATGCGCATCGTCTCCCTCACCGACCCGGGCACGGACCTCC
CCGCCGGAGAGTCCGGGGAGATCCTCATCCGCGGCCCCCAGATCATGAAGGG
CTACCTGGGCCGCCCCGACGCCACCGCCGCCATGATCGACGAGGAGGGCTGG
CTGCACACCGGGGACGTCGGACACGTCGACGCCGACGGCTGGCTGTTCGTCG
TCGACCGCGTCAAGGAACTGATCAAGTACAAGGGCTTCCAGGTGGCCCCCGC
CGAACTGGAGGCCCACCTGCTCACCCACCCCGGCGTCGCCGACGCGGCCGTC
GTCGGCGCCTACGACGACGACGGCAACGAGGTACCGCACGCCTTCGTCGTCC
GCCAGCCGGCCGCACCCGGCCTCGCGGAGAGCGAGATCATGATGTACGTCGC
CGAACGCGTCGCCCCCTACAAACGCGTCCGCCGGGTCACCTTCGTCGACGCC
GTCCCCCGCGCCGCCTCCGGCAAGATCCTCCGCCGACAGCTCAGGGAGCCGC
GATGA (SEQ ID NO:35)

MFRSEYADVPPVDLPIHDAVLGGAAAFGSTPALIDGTDGTTLTYEQVDRFHRRV
AAALAETGVRKGDVLALHSPNTVAFPLAFYAATRAGASVTTVHPLATAEEFAKQ
LKDSAARWIVTVSPLLSTARRAAELAGGVQEILVCDSAPGHRSLVDMLASTAPEP
SVAIDPAEDVAALPYSSGTTGTPKGVMLTHRQIATNLAQLEPSMPSAPGDRVLA
VLPFFHIYGLTALMNAPLRLGATVVVLPRFDLEQFLAAIQNHRITSLYVAPPIVLA
LAKHPLVADYDLSSLRYIVSAAAPLDARLAAACSQRLGLPPVGQAYGMTELSPG
THVVPLDAMADAPPGTVGRLIAGTEMRIVSLTDPGTDLPAGESGEILIRGPQIMK
GYLGRPDATAAMIDEEGWLHTGDVGHVDADGWLFVVDRVKELIKYKGFQVAP
AELEAHLLTHPGVADAAVVGAYDDDGNEVPHAFVVRQPAAPGLAESEIMMYV
AERVAPYKRVRRVTFVDAVPRAASGKILRRQLREPR (SEQ ID NO:36)

Figure 35

```
ATGGTGTCTGTGAGTGAGATCCGCAAAGTTCAAAGGGCAGAAGGCCCTGCAACTGTATTG
GCGATAGGCACAGCAAATCCACCAAATTGTATTGATCAGAGCACATATGCTGATTATTAT
TTTAGAGTAACTAACAGTGAACACATGACTGATCTCAAGAAGAAGTTTCAGCGCATTTGT
GAGAGAACACAAATCAAGAACAGACATATGTACTTAACAGAAGAGATACTGAAAGAGAATC
CTAACATGTGCGCATACAAAGCACCGTCGTTGGATGCAAGGGAAGACATGATGATCAGGGAG
GTACCAAGGGTTGGAAAAGAGGCTGCAACCAAGGCCATCAAGGAATGGGGTCAGCCAATGTC
TAAGATCACACATTTGATCTTCTGCACCACCAGCGGTGTTGCATTGCCTGGCGTTGATTACGA
ACTCATCGTACTCTTAGGACTCGACCCATCCGTCAAGAGGTACATGATGTACCACCAAGGCTG
CTTCGCCGGTGGCACTGTCCTTCGTTTGGCTAAGGACTTGGCTGAAAACAACAAGGATGCTCG
TGTGCTTATCGTTTGTTCTGAGAATACCGCAGTCACTTTCCGTGGTCCTAGTGAGACAGACATG
GATAGTCTTGTAGGGCAAGCCTTGTTTGCTGATGGAGCTGCTGCGATTATCATTGGTTCTGATC
CTGTGCCAGAGGTTGAAAAGCCTATCTTTGAAATTGTTTCGACTGATCAAAAACTTGTCCCTA
ACAGCCATGGAGCCATCGGTGGTCTCCTTCGTGAAGTTGGGCTTACATTCTATCTTAATAAGA
GTGTTCCTGATATTATTTCACAAAACATCAATGATGCGCTCAGTAAAGCTTTTGATCCATTGGG
TATATCTGATTATAACTCAATATTTTGGATTGCACACCCTGGTGGACGTGCAATTTTGGATCAG
GTTGAACAGAAAGTGAACTTGAAACCAGAGAAGATGAATGCCACTAGAGACGTGCTTAGCAA
TTACGGTAACATGTCAAGTGCGTGTGTGTTCTTCATCATGGATTTAATGAGGAAGAAGTCCCT
TGAAGAAGGACTTAAAACTACCGGTGAAGGACTTGATTGGGGCGTACTTTTTGGCTTTGGTCC
TGGTCTCACTATTGAAACTGTTGTTCTCCGCAGCATGGCCATATAA
```

MVSVSEIRKVQRAEGPATVLAIGTANPPNCIDQSTYADYYFRVTNSEHMTDLKKKFQRIC
ERTQIKNRHMYLTEEILKENPNMCAYKAPSLDAREDMMIREVPRVGKEAATKAIKEWGQP
MSKITHLIFCTTSGVALPGVDYELIVLLGLDPSVKRYMMYHQGCFAGGTVLRLAKDLAEN
NKDARVLIVCSENTAVTFRGPSETDMDSLVGQALFADGAAAIIIGSDPVPEVEKPIFEIV
STDQKLVPNSHGAIGGLLREVGLTFYLNKSVPDIISQNINDALSKAFDPLGISDYNSIFW
IAHPGGRAILDQVEQKVNLKPEKMNATRDVLSNYGNMSSACVFFIMDLMRKKSLEEGLKT
TGEGLDWGVLFGFGPGLTIETVVLRSMAI

Figure 36

ATGGCTCCAGGAACTTTGACTGAGCTAGCCGGAGAGTCTAAGCTCAACTCTAAATTCGTC
CGAGACGAAGACGAACGCCCTAAAGTCGCTTACAATGTGTTTAGCGACGAAATCCCGGTG
ATCTCTCTCGCCGGTATCGATGACGTCGATGGAAAAGAGGAGAGATCTGCCGTCAGATC
GTCGAGGCTTGTGAGAATTGGGGTATCTTCCAAGTGGTTGATCACGGCGTCGATACTAAC
TTGGTGGCGGATATGACTCGCCTCGCTCGTGACTTCTTTGCTTTACCTCCGGAAGACAAG
CTCCGTTTCGACATGTCCGGTGGTAAAAAAGGTGGATTCATCGTCTCTAGTCACCTCCAG
GGAGAGGCTGTGCAAGATTGGAGAGAGATTGTAACGTATTTCTCGTACCCGGTGAGAAAC
AGAGACTACTCACGGTGGCCAAATAAGCCTGAAGGATGGGTGAAAGTGACGGAGGAGTATAG
TGAGAGGCTTATGAGTTTGGCTTGTAAGCTTCTTGAGGTTTTGTCTGAAGCTATGGGT
CTTGAGAAAGAGTCTCTTACCAATGCATGCGTCGATATGGACCAAAAGATTGTTGTTAAT
TATTACCCAAAATGCCCTCAGCCTGATCTCACCCTCGGACTCAAGCGTCACACTGACCCT
GGAACCATTACCTTGCTGCTACAAGACCAAGTCGGTGGATTACAAGCCACACGTGACAAT
GGCAAGACCTGGATTACGGTTCAGCCTGTTGAAGGAGCGTTTGTCGTCAATCTCGGCGAC
CACGGTCATTTTTTGAGCAATGGGAGGTTCAAGAATGCTGATCATCAGGCCGTGGTGAAC
TCTAACTCGAGCAGATTATCCATAGCCACGTTCCAGAACCCCGCGCCGGATGCCACAGTG
TATCCACTGAAAGTAAGAGAAGGAGAGAAGGCAATATTGGAGGAGCCAATCACGTTTGCCGA
GATGTATAAGAGAAAGATGGGAAGAGATTTGGAGCTTGCTCGCCTCAAGAAGCTGGCTAAAG
AGGAGCGTGACCACAAAGAAGTTGCCAAGCCTGTCGACCAAATCTTCGCTTGA

MAPGTLTELAGESKLNSKFVRDEDERPKVAYNVFSDEIPVISLAGIDDVDGKRGEICRQI
VEACENWGIFQVVDHGVDTNLVADMTRLARDFFALPPEDKLRFDMSGGKKGGFIVSSHLQ
GEAVQDWREIVTYFSYPVRNRDYSRWPNKPEGWVKVTEEYSERLMSLACKLLEVLSEAMG
LEKESLTNACVDMDQKIVVNYYPKCPQPDLTLGLKRHTDPGTITLLLQDQVGGLQATRDN
GKTWITVQPVEGAFVVNLGDHGHFLSNGRFKNADHQAVVNSNSSRLSIATFQNPAPDATV
YPLKVREGEKAILEEPITFAEMYKRKMGRDLELARLKKLAKEERDHKEVAKPVDQIFA

Figure 37

ATGGAGGTCGAAAGAGTCCAAGACATTTCATCTTCTTCTCTACTAACAGAAGCAATCCCG
TTGGAGTTCATCAGATCAGAGAAAGAACAACCAGCGATCACAACATTCCGAGGTCCAACG
CCGGCGATTCCCGTCGTCGATCTAAGCGATCCCGACGAAGAAAGCGTGAGGCGTGCGGTG
GTGAAAGCGAGTGAAGAATGGGGGCTATTCCAAGTGGTTAACCACGGGATTCCGACGGAGCT
GATACGACGTTTACAAGACGTCGGAAGAAAATTCTTCGAGCTTCCTTCGTCGGAGAAAGAATC
CGTCGCTAAACCGGAAGATTCGAAAGACATTGAAGGATACGGAACAAAGCTTCAGAAAGATC
CAGAAGGTAAAAAAGCTTGGGTCGATCATCTCTTCCATCGAATCTGGCCACCGTCATGCGTCA
ATTACAGATTCTGGCCTAAGAATCCACCTGAATACAGGGAGGTGAATGAAGAGTATGCAGTG
CATGTGAAGAAGCTATCGGAGACGTTATTAGGGATTCTCTCGGATGGATTAGGGTTAAAGCGT
GATGCGTTGAAAGAAGGTCTCGGCGGAGAGATGGCGGAGTATATGATGAAGATTAACTATTA
TCCGCCGTGTCCTCGGCCGGATTTAGCTTTAGGTGTACCGGCTCATACAGATCTCAGTGGAAT
CACTCTTCTTGTTCCTAACGAAGTTCCTGGACTTCAAGTTTTCAAAGATGATCACTGGTTCGAT
GCAGAGTATATTCCCTCCGCCGTCATTGTTCACATCGGCGATCAGATTCTGAGGTTGAGTAAT
GGGAGGTATAAAAATGTGTTGCATAGGACGACGGTGGATAAAGAGAAGACGAGGATGTCGTG
GCCGGTTTTCTTGGAGCCTCCCCGTGAAAAGATTGTTGGACCTTTACCGGAACTAACCGGAGA
TGATAATCCTCCAAAGTTTAAACCGTTTGCTTTCAAGGATTACAGTTACCGCAAGCTCAATAA
ACTTCCTCTGGATTGA

MEVERVQDISSSSLLTEAIPLEFIRSEKEQPAITTFRGPTPAIPVVDLSDPDEESVRRAV
VKASEEWGLFQVVNHGIPTELIRRLQDVGRKFFELPSSEKESVAKPEDSKDIEGYGTKLQ
KDPEGKKAWVDHLFHRIWPPSCVNYRFWPKNPPEYREVNEEYAVHVKKLSETLLGILSDG
LGLKRDALKEGLGGEMAEYMMKINYYPPCPRPDLALGVPAHTDLSGITLLVPNEVPGLQV
FKDDHWFDAEYIPSAVIVHIGDQILRLSNGRYKNVLHRTTVDKEKTRMSWPVFLEPPREK
IVGPLPELTGDDNPPKFKPFAFKDYSYRKLNKLPLD

```
                          SEQUENCE LISTING

<160> NUMBER OF SEQ ID NOS: 47

<210> SEQ ID NO 1
<211> LENGTH: 1686
<212> TYPE: DNA
<213> ORGANISM: Arabidopsis thaliana

<400> SEQUENCE: 1
atggcgccac aagaacaagc agtttctcag gtgatggaga aacagagcaa caacaacaac      60
agtgacgtca ttttccgatc aaagttaccg gatatttaca tcccgaacca cctatctctc     120
cacgactaca tcttccaaaa catctccgaa ttcgccacta agccttgcct aatcaacgga     180
ccaaccggcc acgtgtacac ttactccgac gtccacgtca tctcccgcca aatcgccgcc     240
aattttcaca aactcggcgt taaccaaaac gacgtcgtca tgctcctcct cccaaactgt     300
cccgaattcg tcctctcttt cctcgccgcc tccttccgcg gcgcaaccgc caccgccgca     360
```

```
aacccttct   tcactccggc  ggagatagct  aaacaagcca  aagcctccaa  caccaaactc   420
ataatcaccg  aagctcgtta  cgtcgacaaa  atcaaaccac  ttcaaaacga  cgacggagta   480
gtcatcgtct  gcatcgacga  caacgaatcc  gtgccaatcc  ctgaaggctg  cctccgcttc   540
accgagttga  ctcagtcgac  aaccgaggca  tcagaagtca  tcgactcggt  ggagatttca   600
ccggacgacg  tggtggcact  accttactcc  tctggcacga  cgggattacc  aaaaggagtg   660
atgctgactc  acaagggact  agtcacgagc  gttgctcagc  aagtcgacgg  cgagaacccg   720
aatctttatt  tccacagcga  tgacgtcata  ctctgtgttt  tgcccatgtt  tcatatctac   780
gctttgaact  cgatcatgtt  gtgtggtctt  agagttggtg  cggcgattct  gataatgccg   840
aagtttgaga  tcaatctgct  attggagctg  atccagaggt  gtaaagtgac  ggtggctccg   900
atggttccgc  cgattgtgtt  ggccattgcg  aagtcttcgg  agacggagaa  gtatgatttg   960
agctcgataa  gagtggtgaa  atctggtgct  gctcctcttg  gtaaagaact  tgaagatgcc  1020
gttaatgcca  agtttcctaa  tgccaaactc  ggtcagggat  acggaatgac  ggaagcaggt  1080
ccagtgctag  caatgtcgtt  aggttttgca  aaggaaccct  ttccggttaa  gtcaggagct  1140
tgtggtactg  ttgtaagaaa  tgctgagatg  aaaatagttg  atccagacac  cggagattct  1200
ctttcgagga  atcaacccgg  tgagatttgt  attcgtggtc  accagatcat  gaaaggttac  1260
ctcaacaatc  cggcagctac  agcagagacc  attgataaag  acggttggct  tcatactgga  1320
gatattggat  tgatcgatga  cgatgacgag  cttttcatcg  ttgatcgatt  gaaagaactt  1380
atcaagtata  aaggttttca  ggtagctccg  gctgagctag  aggctttgct  catcggtcat  1440
cctgacatta  ctgatgttgc  tgttgtcgca  atgaaagaag  aagcagctgg  tgaagttcct  1500
gttgcatttg  tggtgaaatc  gaaggattcg  gagttatcag  aagatgatgt  gaagcaattc  1560
gtgtcgaaac  aggttgtgtt  ttacaagaga  atcaacaaag  tgttcttcac  tgaatccatt  1620
cctaaagctc  catcagggaa  gatattgagg  aaagatctga  gggcaaaact  agcaaatgga  1680
ttgtga                                                                  1686
```

<210> SEQ ID NO 2
<211> LENGTH: 561
<212> TYPE: PRT
<213> ORGANISM: Arabidopsis thaliana

<400> SEQUENCE: 2

```
Met Ala Pro Gln Glu Gln Ala Val Ser Gln Val Met Glu Lys Gln Ser
 1               5                  10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
           100                 105                 110

Arg Gly Ala Thr Ala Thr Ala Ala Asn Pro Phe Phe Thr Pro Ala Glu
       115                 120                 125
```

-continued

```
Ile Ala Lys Gln Ala Lys Ala Ser Asn Thr Lys Leu Ile Thr Glu
    130                 135                 140
Ala Arg Tyr Val Asp Lys Ile Lys Pro Leu Gln Asn Asp Asp Gly Val
145                 150                 155                 160
Val Ile Val Cys Ile Asp Asp Asn Glu Ser Val Pro Ile Pro Glu Gly
                165                 170                 175
Cys Leu Arg Phe Thr Glu Leu Thr Gln Ser Thr Thr Glu Ala Ser Glu
                180                 185                 190
Val Ile Asp Ser Val Glu Ile Ser Pro Asp Asp Val Val Ala Leu Pro
            195                 200                 205
Tyr Ser Ser Gly Thr Thr Gly Leu Pro Lys Gly Val Met Leu Thr His
            210                 215                 220
Lys Gly Leu Val Thr Ser Val Ala Gln Gln Val Asp Gly Glu Asn Pro
225                 230                 235                 240
Asn Leu Tyr Phe His Ser Asp Asp Val Ile Leu Cys Val Leu Pro Met
                245                 250                 255
Phe His Ile Tyr Ala Leu Asn Ser Ile Met Leu Cys Gly Leu Arg Val
                260                 265                 270
Gly Ala Ala Ile Leu Ile Met Pro Lys Phe Glu Ile Asn Leu Leu Leu
            275                 280                 285
Glu Leu Ile Gln Arg Cys Lys Val Thr Val Ala Pro Met Val Pro Pro
290                 295                 300
Ile Val Leu Ala Ile Ala Lys Ser Ser Glu Thr Glu Lys Tyr Asp Leu
305                 310                 315                 320
Ser Ser Ile Arg Val Val Lys Ser Gly Ala Ala Pro Leu Gly Lys Glu
                325                 330                 335
Leu Glu Asp Ala Val Asn Ala Lys Phe Pro Asn Ala Lys Leu Gly Gln
            340                 345                 350
Gly Tyr Gly Met Thr Glu Ala Gly Pro Val Leu Ala Met Ser Leu Gly
            355                 360                 365
Phe Ala Lys Glu Pro Phe Pro Val Lys Ser Gly Ala Cys Gly Thr Val
370                 375                 380
Val Arg Asn Ala Glu Met Lys Ile Val Asp Pro Asp Thr Gly Asp Ser
385                 390                 395                 400
Leu Ser Arg Asn Gln Pro Gly Glu Ile Cys Ile Arg Gly His Gln Ile
                405                 410                 415
Met Lys Gly Tyr Leu Asn Asn Pro Ala Ala Thr Ala Glu Thr Ile Asp
            420                 425                 430
Lys Asp Gly Trp Leu His Thr Gly Asp Ile Gly Leu Ile Asp Asp Asp
            435                 440                 445
Asp Glu Leu Phe Ile Val Asp Arg Leu Lys Glu Leu Ile Lys Tyr Lys
450                 455                 460
Gly Phe Gln Val Ala Pro Ala Glu Leu Glu Ala Leu Leu Ile Gly His
465                 470                 475                 480
Pro Asp Ile Thr Asp Val Ala Val Val Ala Met Lys Glu Glu Ala Ala
                485                 490                 495
Gly Glu Val Pro Val Ala Phe Val Val Lys Ser Lys Asp Ser Glu Leu
            500                 505                 510
Ser Glu Asp Asp Val Lys Gln Phe Val Ser Lys Gln Val Val Phe Tyr
            515                 520                 525
Lys Arg Ile Asn Lys Val Phe Phe Thr Glu Ser Ile Pro Lys Ala Pro
530                 535                 540
```

Ser Gly Lys Ile Leu Arg Lys Asp Leu Arg Ala Lys Leu Ala Asn Gly
545                 550                 555                 560

Leu

<210> SEQ ID NO 3
<211> LENGTH: 1188
<212> TYPE: DNA
<213> ORGANISM: Arabidopsis thaliana

<400> SEQUENCE: 3

```
atggtgatgg ctggtgcttc ttctttggat gagatcagac aggctcagag agctgatgga      60
cctgcaggca tcttggctat tggcactgct aaccctgaga accatgtgct tcaggcggag     120
tatcctgact actacttccg catcaccaac agtgaacaca tgaccgacct caaggagaag     180
ttcaagcgca tgtgcgacaa gtcgacaatt cggaaacgtc acatgcatct gacggaggaa     240
ttcctcaagg aaaacccaca catgtgtgct tacatggctc cttctctgga caccagacag     300
gacatcgtgg tggtcgaagt ccctaagcta ggcaaagaag cggcagtgaa ggccatcaag     360
gagtggggcc agcccaagtc aaagatcact catgtcgtct tctgcactac ctccggcgtc     420
gacatgcctg gtgctgacta ccagctcacc aagcttcttg gtctccgtcc ttccgtcaag     480
cgtctcatga tgtaccagca aggttgcttc gccggcggta ctgtcctccg tatcgctaag     540
gatctcgccg agaacaaccg tggagcacgt gtcctcgttg tctgctctga gatcacagcc     600
gttaccttcc gtggtcctc tgacacccac cttgactccc tcgtcggtca ggctcttttc     660
agtgatggcg ccgccgcact cattgtgggg tcggaccctg acacatctgt cggagagaaa     720
cccatctttg agatggtgtc tgccgctcag accatccttc agactctga tggtgccata     780
gacggacatt tgagggaagt tggtctcacc ttccatctcc tcaaggatgt tcccggcctc     840
atctccaaga acattgtgaa gagtctagac gaagcgttta aacctttggg gataagtgac     900
tggaactccc tcttctggat agcccaccct ggaggtccag cgatcctaga ccaggtggag     960
ataaagctag gactaaagga gagaagatg agggcgacac gtcacgtgtt gagcgagtat    1020
ggaaacatgt cgagcgcgtg cgttctcttc atactagacg agatgaggag gaagtcagct    1080
aaggatggtg tggccacgac aggagaaggg ttggagtggg gtgtcttgtt tggtttcgga    1140
ccaggtctca ctgttgagac agtcgtcttg cacagcgttc tctctaa                 1188
```

<210> SEQ ID NO 4
<211> LENGTH: 395
<212> TYPE: PRT
<213> ORGANISM: Arabidopsis thaliana

<400> SEQUENCE: 4

Met Val Met Ala Gly Ala Ser Ser Leu Asp Glu Ile Arg Gln Ala Gln
1               5                   10                  15

Arg Ala Asp Gly Pro Ala Gly Ile Leu Ala Ile Gly Thr Ala Asn Pro
                20                  25                  30

Glu Asn His Val Leu Gln Ala Glu Tyr Pro Asp Tyr Tyr Phe Arg Ile
            35                  40                  45

Thr Asn Ser Glu His Met Thr Asp Leu Lys Glu Lys Phe Lys Arg Met
        50                  55                  60

Cys Asp Lys Ser Thr Ile Arg Lys Arg His Met His Leu Thr Glu Glu
65                  70                  75                  80

Phe Leu Lys Glu Asn Pro His Met Cys Ala Tyr Met Ala Pro Ser Leu
                85                  90                  95

```
Asp Thr Arg Gln Asp Ile Val Val Glu Val Pro Lys Leu Gly Lys
                100                 105                 110
Glu Ala Ala Val Lys Ala Ile Lys Glu Trp Gly Gln Pro Lys Ser Lys
    115                 120                 125
Ile Thr His Val Val Phe Cys Thr Thr Ser Gly Val Asp Met Pro Gly
    130                 135                 140
Ala Asp Tyr Gln Leu Thr Lys Leu Leu Gly Leu Arg Pro Ser Val Lys
145                 150                 155                 160
Arg Leu Met Met Tyr Gln Gln Gly Cys Phe Ala Gly Gly Thr Val Leu
                165                 170                 175
Arg Ile Ala Lys Asp Leu Ala Glu Asn Asn Arg Gly Ala Arg Val Leu
            180                 185                 190
Val Val Cys Ser Glu Ile Thr Ala Val Thr Phe Arg Gly Pro Ser Asp
        195                 200                 205
Thr His Leu Asp Ser Leu Val Gly Gln Ala Leu Phe Ser Asp Gly Ala
    210                 215                 220
Ala Ala Leu Ile Val Gly Ser Asp Pro Asp Thr Ser Val Gly Glu Lys
225                 230                 235                 240
Pro Ile Phe Glu Met Val Ser Ala Ala Gln Thr Ile Leu Pro Asp Ser
                245                 250                 255
Asp Gly Ala Ile Asp Gly His Leu Arg Glu Val Gly Leu Thr Phe His
            260                 265                 270
Leu Leu Lys Asp Val Pro Gly Leu Ile Ser Lys Asn Ile Val Lys Ser
        275                 280                 285
Leu Asp Glu Ala Phe Lys Pro Leu Gly Ile Ser Asp Trp Asn Ser Leu
    290                 295                 300
Phe Trp Ile Ala His Pro Gly Gly Pro Ala Ile Leu Asp Gln Val Glu
305                 310                 315                 320
Ile Lys Leu Gly Leu Lys Glu Glu Lys Met Arg Ala Thr Arg His Val
                325                 330                 335
Leu Ser Glu Tyr Gly Asn Met Ser Ser Ala Cys Val Leu Phe Ile Leu
            340                 345                 350
Asp Glu Met Arg Arg Lys Ser Ala Lys Asp Gly Val Ala Thr Thr Gly
        355                 360                 365
Glu Gly Leu Glu Trp Gly Val Leu Phe Gly Phe Gly Pro Gly Leu Thr
    370                 375                 380
Val Glu Thr Val Val Leu His Ser Val Pro Leu
385                 390                 395

<210> SEQ ID NO 5
<211> LENGTH: 1170
<212> TYPE: DNA
<213> ORGANISM: Arachis hypogaea

<400> SEQUENCE: 5
atggtgtctg tgagtggaat tcgcaaggtt caaagagcag aaggtcctgc aaccgtatta      60
gcgattggca cagcaaatcc accaaactgt gttgatcaga gcacatacgc agattactat     120
tttagagtaa ccaatagcga gcacatgacc gacctcaaga agaaatttca gcgcatttgt     180
gagagaacac agatcaagaa cagacatatg tatctaacgg aagaaatact gaaggagaat     240
cctaacatgt gcgcatacaa agcaccgtcc ttggatgcaa gggaagacat gatgatcagg     300
gaggtaccaa gggttggaaa agaggctgca actaaggcaa tcaaggaatg ggtcagcca      360 atgtctaaga tcacacattt gatcttctgc accaccagcg gtgttgcgtt gcctggcgtt     420
```

-continued

```
gattacgaac tcatcgtact cttagggctc gacccaagcg tcaagaggta catgatgtac    480
caccaaggct gcttcgctgg cggcactgtc cttcgtttgg ctaaggactt ggctgaaaac    540
aacaaggatg ctcgtgtgct tattgtttgt tctgaaaata cttcagtcac ttttcgtggt    600
cctagtgaga cagacatgga tagtcttgta ggacaagcat tgtttgccga tggagctgct    660
gcaattatca ttggttctga tcctgttcca gaggttgaga atcctctctt tgagattgtt    720
tcaactgatc aacaacttgt ccctaacagc catggagcca tcggtggtct ccttcgtgaa    780
gttggactta cattctatct taacaagagt gttccggata ttatttcaca aacatcaat     840 gatgcactca gtaaagcttt tgatccacta ggtatatctg attataactc aatatttgg     900 attgcacatc ctggtggacg tgcaattttg gaccaagttg aagagaaggt gaacttgaag    960
ccagagaaga tgaaagccac cagagatgtg cttagcaatt atggtaacat gtcaagtgcg    1020
tgtgtgttct tcattatgga tttgatgaga aagaagtcac ttgaagcagg acttaaaacc    1080
accggagaag gacttgattg gggtgtactt tttggttttg gtcctggtct cactattgaa    1140
actgttgttc tccgcagcat ggccatataa                                     1170
```

<210> SEQ ID NO 6
<211> LENGTH: 389
<212> TYPE: PRT
<213> ORGANISM: Arachis hypogaea

<400> SEQUENCE: 6

```
Met Val Ser Val Ser Gly Ile Arg Lys Val Gln Arg Ala Glu Gly Pro
 1               5                  10                  15

Ala Thr Val Leu Ala Ile Gly Thr Ala Asn Pro Pro Asn Cys Val Asp
                20                  25                  30

Gln Ser Thr Tyr Ala Asp Tyr Tyr Phe Arg Val Thr Asn Ser Glu His
             35                  40                  45

Met Thr Asp Leu Lys Lys Lys Phe Gln Arg Ile Cys Glu Arg Thr Gln
         50                  55                  60

Ile Lys Asn Arg His Met Tyr Leu Thr Glu Glu Ile Leu Lys Glu Asn
 65                  70                  75                  80

Pro Asn Met Cys Ala Tyr Lys Ala Pro Ser Leu Asp Ala Arg Glu Asp
                 85                  90                  95

Met Met Ile Arg Glu Val Pro Arg Val Gly Lys Glu Ala Ala Thr Lys
            100                 105                 110

Ala Ile Lys Glu Trp Gly Gln Pro Met Ser Lys Ile Thr His Leu Ile
        115                 120                 125

Phe Cys Thr Thr Ser Gly Val Ala Leu Pro Gly Val Asp Tyr Glu Leu
    130                 135                 140

Ile Val Leu Leu Gly Leu Asp Pro Ser Val Lys Arg Tyr Met Met Tyr
145                 150                 155                 160

His Gln Gly Cys Phe Ala Gly Gly Thr Val Leu Arg Leu Ala Lys Asp
                165                 170                 175

Leu Ala Glu Asn Asn Lys Asp Ala Arg Val Leu Ile Val Cys Ser Glu
            180                 185                 190

Asn Thr Ser Val Thr Phe Arg Gly Pro Ser Glu Thr Asp Met Asp Ser
        195                 200                 205

Leu Val Gly Gln Ala Leu Phe Ala Asp Gly Ala Ala Ile Ile Ile
    210                 215                 220

Gly Ser Asp Pro Val Pro Glu Val Glu Asn Pro Leu Phe Glu Ile Val
225                 230                 235                 240
```

```
Ser Thr Asp Gln Gln Leu Val Pro Asn Ser His Gly Ala Ile Gly Gly
                245                 250                 255

Leu Leu Arg Glu Val Gly Leu Thr Phe Tyr Leu Asn Lys Ser Val Pro
            260                 265                 270

Asp Ile Ile Ser Gln Asn Ile Asn Asp Ala Leu Ser Lys Ala Phe Asp
        275                 280                 285

Pro Leu Gly Ile Ser Asp Tyr Asn Ser Ile Phe Trp Ile Ala His Pro
    290                 295                 300

Gly Gly Arg Ala Ile Leu Asp Gln Val Glu Glu Lys Val Asn Leu Lys
305                 310                 315                 320

Pro Glu Lys Met Lys Ala Thr Arg Asp Val Leu Ser Asn Tyr Gly Asn
                325                 330                 335

Met Ser Ser Ala Cys Val Phe Phe Ile Met Asp Leu Met Arg Lys Lys
            340                 345                 350

Ser Leu Glu Ala Gly Leu Lys Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

Arg Ser Met Ala Ile
385

<210> SEQ ID NO 7
<211> LENGTH: 1581
<212> TYPE: DNA
<213> ORGANISM: Rhodobacter sphaeroides

<400> SEQUENCE: 7
atgaagccaa tgctcgccat gagccccccg aagccggccg tcgagctgga tcgccacatc      60
gatctggacc aggcccatgc cgtggcgagc ggcggcgcgc ggattgtcct tgcccctccg     120
gcgcgcgacc ggtgccgtgc gtccgaagcg cggctcggcg ctgtcatccg cgaggcgcgc     180
catgtctacg gactgacaac cggcttcggt cccctttgcga accgcctgat ctcaggtgag     240
aatgtccgaa cgctgcaggc caatcttgtc catcatctgg ccagcggcgt gggaccggtg     300
cttgactgga cgacggcgcg cgccatggtt ctggcgcgtc tggtgtcgat cgctcaggga     360
gcctccggtg ccagcgaggg gaccatcgct gcctgatcg acctgctcaa ttccgagctc     420
gctccggccg ttccagccg cggcacggtg ggcgcgtcgg gtgacctgac accgcttgcg     480
catatggtgc tctgcctcca gggcggggga gacttcctgg accgggacgg gacgcggctt     540 gacgcgcag aagggctccg cgcggacgg ctgcaaccgc tcgatctctc ccatcgcgat     600 gcactgcgc tggtcaacgg gacctccgcc atgaccggga tcgcgctggt gaatgctcac     660
gcctgccgcc atctcggcaa ctgggcggtg gcgttgacgg cctgcttgc ggaatgtctg     720 agaggccgga ccgaggcatg ggccgcggca ctgtccgacc tgcggccgca tcccggacag     780
aaggacgccg cagcgaggct gcgcgcccgc gtggacggca gcgcgcggt ggtccggcac     840 gtcattgccg agcggaggct cgacgccggc gatatcggga cggagccgga ggcggggcag     900
gatgcctaca gctgcgctg cgctccgcag gttctcgggg cgggcttcga cacgctcgca     960
tggcatgacc gggtgctgac gatcgagctg aacgcggtga ccgacaatcc ggtgtttccg    1020
cccgatggca gcgtgcccgc cctgcacggg ggcaatttca tgggccagca tgtgcgctg    1080 acgtccgatg cgctcgccac ggccgtcacc gttctggcgg ccttgcggga cgccagatt    1140 gcacgtctga cagatgaaag gctgaaccgt gggctgcccc ccttcctcca ccggggcccc    1200
gccgggttga attccggctt catgggcgca caggtgacgg cgaccgcgct cctggccgag    1260
```

```
atgcgagcca cgggacctgc ctcgatccat tcgatctcca cgaacgccgc caatcaggat    1320
gtggtctcgc ttgggaccat cgccgcgcgc tctgccgcg agaagatcga ccgttgggcg    1380
gagatccttg cgatcctcgc tctctgtctt gcacaagctg cggagctgcg ctgcggcagc    1440
ggcctagacg gggtgtctcc cgcggggaag aagctggtgc aggccctgcg cgagcagttc    1500
ccgccgcttg agacggaccg gccccctggga caggaaattg ccgcgcttgc tacgcacctc    1560
ttgcagcaat ctcccgtctg a                                              1581
```

<210> SEQ ID NO 8
<211> LENGTH: 526
<212> TYPE: PRT
<213> ORGANISM: Rhodobacter sphaeroides

<400> SEQUENCE: 8

```
Met Lys Pro Met Leu Ala Met Ser Pro Pro Lys Pro Ala Val Glu Leu
 1               5                  10                  15

Asp Arg His Ile Asp Leu Asp Gln Ala His Ala Val Ala Ser Gly Gly
             20                  25                  30

Ala Arg Ile Val Leu Ala Pro Pro Ala Arg Asp Arg Cys Arg Ala Ser
         35                  40                  45

Glu Ala Arg Leu Gly Ala Val Ile Arg Glu Ala Arg His Val Tyr Gly
     50                  55                  60

Leu Thr Thr Gly Phe Gly Pro Leu Ala Asn Arg Leu Ile Ser Gly Glu
 65                  70                  75                  80

Asn Val Arg Thr Leu Gln Ala Asn Leu Val His His Leu Ala Ser Gly
                 85                  90                  95

Val Gly Pro Val Leu Asp Trp Thr Thr Ala Arg Ala Met Val Leu Ala
            100                 105                 110

Arg Leu Val Ser Ile Ala Gln Gly Ala Ser Gly Ala Ser Glu Gly Thr
        115                 120                 125

Ile Ala Arg Leu Ile Asp Leu Leu Asn Ser Glu Leu Ala Pro Ala Val
    130                 135                 140

Pro Ser Arg Gly Thr Val Gly Ala Ser Gly Asp Leu Thr Pro Leu Ala
145                 150                 155                 160

His Met Val Leu Cys Leu Gln Gly Arg Gly Asp Phe Leu Asp Arg Asp
                165                 170                 175

Gly Thr Arg Leu Asp Gly Ala Glu Gly Leu Arg Arg Gly Arg Leu Gln
            180                 185                 190

Pro Leu Asp Leu Ser His Arg Asp Ala Leu Ala Leu Val Asn Gly Thr
        195                 200                 205

Ser Ala Met Thr Gly Ile Ala Leu Val Asn Ala His Ala Cys Arg His
    210                 215                 220

Leu Gly Asn Trp Ala Val Ala Leu Thr Ala Leu Leu Ala Glu Cys Leu
225                 230                 235                 240

Arg Gly Arg Thr Glu Ala Trp Ala Ala Leu Ser Asp Leu Arg Pro
                245                 250                 255

His Pro Gly Gln Lys Asp Ala Ala Ala Arg Leu Arg Ala Arg Val Asp
            260                 265                 270

Gly Ser Ala Arg Val Val Arg His Val Ile Ala Glu Arg Arg Leu Asp
        275                 280                 285

Ala Gly Asp Ile Gly Thr Glu Pro Glu Ala Gly Gln Asp Ala Tyr Ser
    290                 295                 300
```

```
Leu Arg Cys Ala Pro Gln Val Leu Gly Ala Gly Phe Asp Thr Leu Ala
305                 310                 315                 320

Trp His Asp Arg Val Leu Thr Ile Glu Leu Asn Ala Val Thr Asp Asn
            325                 330                 335

Pro Val Phe Pro Pro Asp Gly Ser Val Pro Ala Leu His Gly Gly Asn
        340                 345                 350

Phe Met Gly Gln His Val Ala Leu Thr Ser Asp Ala Leu Ala Thr Ala
    355                 360                 365

Val Thr Val Leu Ala Gly Leu Ala Glu Arg Gln Ile Ala Arg Leu Thr
370                 375                 380

Asp Glu Arg Leu Asn Arg Gly Leu Pro Pro Phe Leu His Arg Gly Pro
385                 390                 395                 400

Ala Gly Leu Asn Ser Gly Phe Met Gly Ala Gln Val Thr Ala Thr Ala
            405                 410                 415

Leu Leu Ala Glu Met Arg Ala Thr Gly Pro Ala Ser Ile His Ser Ile
        420                 425                 430

Ser Thr Asn Ala Ala Asn Gln Asp Val Val Ser Leu Gly Thr Ile Ala
    435                 440                 445

Ala Arg Leu Cys Arg Glu Lys Ile Asp Arg Trp Ala Glu Ile Leu Ala
450                 455                 460

Ile Leu Ala Leu Cys Leu Ala Gln Ala Ala Glu Leu Arg Cys Gly Ser
465                 470                 475                 480

Gly Leu Asp Gly Val Ser Pro Ala Gly Lys Lys Leu Val Gln Ala Leu
            485                 490                 495

Arg Glu Gln Phe Pro Pro Leu Glu Thr Asp Arg Pro Leu Gly Gln Glu
        500                 505                 510

Ile Ala Ala Leu Ala Thr His Leu Leu Gln Gln Ser Pro Val
    515                 520                 525

<210> SEQ ID NO 9
<211> LENGTH: 2178
<212> TYPE: DNA
<213> ORGANISM: Arabidopsis thaliana

<400> SEQUENCE: 9
atggagatta cgggggcaca caagagcaac ggaggaggag tggacgctat gttatgcggc      60
ggagacatca agacaaagaa catggtgatc aacgcggagg atcctctcaa ctggggagct     120
gcagcggagc aaatgaaagg tagccatttg gatgaagtga agagaatggt tgctgagttt     180
aggaagccag ttgtgaatct tggtggtgag actctgacca ttggacaagt ggctgcgatc     240
tcaactattg gtaacagtgt gaaggtggag ctatcggaga cagctagagc cggtgtgaat     300
gctagtagtg attgggttat ggagagtatg aacaaaggca ctgatagtta tggtgttact     360
actggttttg gtgctacttc tcatcggaga accaaaaacg gtgtcgcact tcagaaggaa     420
cttattagat tccttaacgc cggaatattc ggaagcacga agaaacaagc cacacattg     480 ccacactccg ccacaagagc cgccatgctt gtacgaatca acactctcct ccaaggattt     540
tccggtatcc gatttgagat tctcgaagca attaccagtt cctcaacaa caacatcact     600 ccatctctcc ccctccgtgg tacaatcacc gcctccggag atctcgttcc tctctcctac     660
atcgccggac ttctcaccgg tcgtcccaat tccaaagcta ctggtcccaa cggtgaagct     720
ttaacagcag aggaagcttt caaattagca ggaatcagct ccggattctt tgatctccag     780
cctaaggaag gtctcgcgct agtcaatggc acggcggttg gatctggaat ggcgtcaatg     840
gtgttattcg aaacgaatgt ctctctctgtt ttggctgaga ttttgtcggc ggttttcgca     900
```

```
gaggtgatga gtggtaagcc tgagttcacc gatcatctca ctcacagact taaacatcat    960
cccggtcaaa tcgaagcggc ggcgataatg gagcatatcc tcgacggaag ctcgtacatg   1020
aaattagctc agaagcttca cgagatggat ccgttacaga aacctaaaca agatcgttac   1080
gctcttcgta cttctcctca atggttaggt cctcaaatcg aagtgatccg ttacgcaacg   1140
aaatcgatcg agcgtgagat taactccgtc aacgataatc cgttgatcga tgtttcgagg   1200
aacaaggcga ttcacggtgg taacttccaa ggaacaccaa tcggagtttc aatggataac   1260
acgagattgg cgatagcagc gattggtaaa ctcatgtttg ctcaattctc agagcttgtg   1320
aatgatttct acaacaatgg tttaccctcg aatctaaccg cttcgaggaa tccaagtttg   1380
gattatggat tcaagggagc tgagattgca atggcttctt attgttcaga gcttcaatac   1440
ttagctaatc ctgtgactag ccatgttcaa tcagcagagc aacataacca agatgtcaac   1500
tctttgggac taatctcgtc tcgcaaaact tctgaagctg ttgatattct caagcttatg   1560
tcaacaacgt tcctcgttgc gatttgtcaa gctgtggatt tgagacattt ggaggagaat   1620
ttgagacaga ctgtgaagaa cactgtctct caagtggcga agaaagttct tactactgga   1680
gtcaatggtg agcttcatcc ttctcgcttc tgcgaaaagg atttactcaa agttgtagac   1740
cgtgaacaag tctacacata cgcggatgat ccttgtagcg caacgtaccc gttgattcag   1800
aagctgagac aagttattgt tgaccatgct ttgatcaatg gtgagagtga aagaatgca    1860
gtgacttcaa tcttccataa gattggagct ttcgaggagg agcttaaggc agtgctaccg   1920
aaagaagtgg aagcagcaag agcagcctac gataacggaa catcggctat cccgaacagg   1980
atcaaggaat gtaggtcgta tccattgtat agattcgtga gggaagagct tggaacagag   2040
ctttttgaccg gagagaaagt gacgtcgcct ggagaagagt tcgacaaggt tttcacggcg   2100
atttgtgaag gtaaaatcat tgatccgatg atggaatgtc tcaacgagtg gaacggagct   2160
cccattccaa tatgttaa                                                  2178

<210> SEQ ID NO 10
<211> LENGTH: 725
<212> TYPE: PRT
<213> ORGANISM: Arabidopsis thaliana

<400> SEQUENCE: 10

Met Glu Ile Asn Gly Ala His Lys Ser Asn Gly Gly Val Asp Ala
 1               5                  10                  15

Met Leu Cys Gly Gly Asp Ile Lys Thr Lys Asn Met Val Ile Asn Ala
                20                  25                  30

Glu Asp Pro Leu Asn Trp Gly Ala Ala Ala Glu Gln Met Lys Gly Ser
            35                  40                  45

His Leu Asp Glu Val Lys Arg Met Val Ala Glu Phe Arg Lys Pro Val
        50                  55                  60

Val Asn Leu Gly Gly Glu Thr Leu Thr Ile Gly Gln Val Ala Ala Ile
 65                  70                  75                  80

Ser Thr Ile Gly Asn Ser Val Lys Val Glu Leu Ser Glu Thr Ala Arg
                85                  90                  95

Ala Gly Val Asn Ala Ser Ser Asp Trp Val Met Glu Ser Met Asn Lys
            100                 105                 110

Gly Thr Asp Ser Tyr Gly Val Thr Thr Gly Phe Gly Ala Thr Ser His
        115                 120                 125

Arg Arg Thr Lys Asn Gly Val Ala Leu Gln Lys Glu Leu Ile Arg Phe
    130                 135                 140
```

-continued

```
Leu Asn Ala Gly Ile Phe Gly Ser Thr Lys Glu Thr Ser His Thr Leu
145                 150                 155                 160

Pro His Ser Ala Thr Arg Ala Ala Met Leu Val Arg Ile Asn Thr Leu
                165                 170                 175

Leu Gln Gly Phe Ser Gly Ile Arg Phe Glu Ile Leu Glu Ala Ile Thr
            180                 185                 190

Ser Phe Leu Asn Asn Ile Thr Pro Ser Leu Pro Leu Arg Gly Thr
        195                 200                 205

Ile Thr Ala Ser Gly Asp Leu Val Pro Leu Ser Tyr Ile Ala Gly Leu
    210                 215                 220

Leu Thr Gly Arg Pro Asn Ser Lys Ala Thr Gly Pro Asn Gly Glu Ala
225                 230                 235                 240

Leu Thr Ala Glu Glu Ala Phe Lys Leu Ala Gly Ile Ser Ser Gly Phe
                245                 250                 255

Phe Asp Leu Gln Pro Lys Glu Gly Leu Ala Leu Val Asn Gly Thr Ala
            260                 265                 270

Val Gly Ser Gly Met Ala Ser Met Val Leu Phe Glu Thr Asn Val Leu
        275                 280                 285

Ser Val Leu Ala Glu Ile Leu Ser Ala Val Phe Ala Glu Val Met Ser
    290                 295                 300

Gly Lys Pro Glu Phe Thr Asp His Leu Thr His Arg Leu Lys His His
305                 310                 315                 320

Pro Gly Gln Ile Glu Ala Ala Ile Met Glu His Ile Leu Asp Gly
                325                 330                 335

Ser Ser Tyr Met Lys Leu Ala Gln Lys Leu His Glu Met Asp Pro Leu
            340                 345                 350

Gln Lys Pro Lys Gln Asp Arg Tyr Ala Leu Arg Thr Ser Pro Gln Trp
        355                 360                 365

Leu Gly Pro Gln Ile Glu Val Ile Arg Tyr Ala Thr Lys Ser Ile Glu
    370                 375                 380

Arg Glu Ile Asn Ser Val Asn Asp Asn Pro Leu Ile Asp Val Ser Arg
385                 390                 395                 400

Asn Lys Ala Ile His Gly Gly Asn Phe Gln Gly Thr Pro Ile Gly Val
                405                 410                 415

Ser Met Asp Asn Thr Arg Leu Ala Ile Ala Ala Ile Gly Lys Leu Met
            420                 425                 430

Phe Ala Gln Phe Ser Glu Leu Val Asn Asp Phe Tyr Asn Asn Gly Leu
        435                 440                 445

Pro Ser Asn Leu Thr Ala Ser Arg Asn Pro Ser Leu Asp Tyr Gly Phe
    450                 455                 460

Lys Gly Ala Glu Ile Ala Met Ala Ser Tyr Cys Ser Glu Leu Gln Tyr
465                 470                 475                 480

Leu Ala Asn Pro Val Thr Ser His Val Gln Ser Ala Glu Gln His Asn
                485                 490                 495

Gln Asp Val Asn Ser Leu Gly Leu Ile Ser Ser Arg Lys Thr Ser Glu
            500                 505                 510

Ala Val Asp Ile Leu Lys Leu Met Ser Thr Thr Phe Leu Val Ala Ile
        515                 520                 525

Cys Gln Ala Val Asp Leu Arg His Leu Glu Glu Asn Leu Arg Gln Thr
    530                 535                 540

Val Lys Asn Thr Val Ser Gln Val Ala Lys Lys Val Leu Thr Thr Gly
545                 550                 555                 560
```

```
Val Asn Gly Glu Leu His Pro Ser Arg Phe Cys Glu Lys Asp Leu Leu
            565                 570                 575

Lys Val Val Asp Arg Glu Gln Val Tyr Thr Tyr Ala Asp Asp Pro Cys
        580                 585                 590

Ser Ala Thr Tyr Pro Leu Ile Gln Lys Leu Arg Gln Val Ile Val Asp
            595                 600                 605

His Ala Leu Ile Asn Gly Glu Ser Glu Lys Asn Ala Val Thr Ser Ile
        610                 615                 620

Phe His Lys Ile Gly Ala Phe Glu Glu Leu Lys Ala Val Leu Pro
625                 630                 635                 640

Lys Glu Val Glu Ala Ala Arg Ala Ala Tyr Asp Asn Gly Thr Ser Ala
                645                 650                 655

Ile Pro Asn Arg Ile Lys Glu Cys Arg Ser Tyr Pro Leu Tyr Arg Phe
            660                 665                 670

Val Arg Glu Glu Leu Gly Thr Glu Leu Leu Thr Gly Glu Lys Val Thr
        675                 680                 685

Ser Pro Gly Glu Glu Phe Asp Lys Val Phe Thr Ala Ile Cys Glu Gly
    690                 695                 700

Lys Ile Ile Asp Pro Met Met Glu Cys Leu Asn Glu Trp Asn Gly Ala
705                 710                 715                 720

Pro Ile Pro Ile Cys
            725

<210> SEQ ID NO 11
<211> LENGTH: 1518
<212> TYPE: DNA
<213> ORGANISM: Arabidopsis thaliana

<400> SEQUENCE: 11
atggacctcc tcttgctgga gaagtctcta atcgccgtct tcgtggcggt gattctcgcc      60
acggtgattt caaagctccg cggcaagaaa ttgaagctac ctccaggtcc tataccaatt    120
ccgatcttcg gaaactggct tcaagtagga gatgatctca accaccgtaa tctcgtcgat    180
tacgctaaga aattcggcga tctcttcctc ctccgtatgg gtcagcgtaa cctagtcgtc    240
gtctcttcac cggatctaac caaggaagtg ctccacacac aaggcgttga gtttggatct    300
agaacgagaa acgtcgtgtt cgacattttc accgggaaag gtcaagatat ggtgttcact    360
gtttacggcg agcattggag gaagatgaga agaatcatga cggttccttt cttcaccaac    420
aaagttgttc aacagaatcg tgaaggttgg gagtttgaag cagctagtgt tgttgaagat    480
gttaagaaga atccagattc tgctacgaaa ggaatcgtgt tgaggaaacg tttgcaattg    540
atgatgtata caatatgtt ccgtatcatg ttcgatagaa gatttgagag tgaggatgat    600
cctctttttcc ttaggcttaa ggctttgaat ggtgagagaa gtcgattagc tcagagcttt    660
gagtataact atggagattt cattcctatc cttagaccat tcctcagagg ctatttgaag    720
atttgtcaag atgtgaaaga tcgaagaatc gctcttttca agaagtactt tgttgatgag    780
aggaagcaaa ttgcgagttc taagcctaca ggtagtgaag gattgaaatg tgccattgat    840
cacatccttg aagctgagca agggagaa atcaacgagg acaatgttct ttacatcgtc    900
gagaacatca atgtcgccgc gattgagaca acattgtggt ctatcgagtg ggaattgca    960
gagctagtga accatcctga atccagagt aagctaagga cgaactcga cacggttctt   1020
ggaccgggtg tgcaagtcac cgagcctgat cttcacaaac ttccatacct tcaagctgtg   1080
gttaaggaga ctcttcgtct gagaatggcg attcctctcc tcgtgcctca catgaacctc   1140
```

```
catgatgcga agctcgctgg ctacgatatc ccagcagaaa gcaaaatcct tgttaatgct   1200
tggtggctag caaacaaccc caacagctgg aagaagcctg aagagtttag accagagagg   1260
ttctttgaag aagaatcgca cgtggaagct aacggaaatg acttcaggta tgtgccgttt   1320
ggtgttggac gtagaagctg tcccgggatt atattggcat tacctatttt ggggatcacc   1380
attggtagga tggtccagaa cttcgagctt cttcctcctc caggacagtc taaagtggat   1440
actagtgaga aggtggaca attcagcttg cacatcctta accactccat aatcgttatg   1500
aaaccaagga actgttaa                                                 1518
```

```
<210> SEQ ID NO 12
<211> LENGTH: 505
<212> TYPE: PRT
<213> ORGANISM: Arabidopsis thaliana

<400> SEQUENCE: 12
```

Met Asp Leu Leu Leu Glu Lys Ser Leu Ile Ala Val Phe Val Ala
 1               5                  10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
        35                  40                  45

Val Gly Asp Asp Leu Asn His Arg Asn Leu Val Asp Tyr Ala Lys Lys
50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Arg Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
                245                 250                 255

Phe Val Asp Glu Arg Lys Gln Ile Ala Ser Ser Lys Pro Thr Gly Ser
            260                 265                 270

Glu Gly Leu Lys Cys Ala Ile Asp His Ile Leu Glu Ala Glu Gln Lys
        275                 280                 285

Gly Glu Ile Asn Glu Asp Asn Val Leu Tyr Ile Val Glu Asn Ile Asn
    290                 295                 300

```
Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
                325                 330                 335

Asp Thr Val Leu Gly Pro Gly Val Gln Val Thr Glu Pro Asp Leu His
            340                 345                 350

Lys Leu Pro Tyr Leu Gln Ala Val Lys Glu Thr Leu Arg Leu Arg
        355                 360                 365

Met Ala Ile Pro Leu Leu Val Pro His Met Asn Leu His Asp Ala Lys
    370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
                405                 410                 415

Arg Pro Glu Arg Phe Phe Glu Glu Ser His Val Glu Ala Asn Gly
            420                 425                 430

Asn Asp Phe Arg Tyr Val Pro Phe Gly Val Gly Arg Arg Ser Cys Pro
            435                 440                 445

Gly Ile Ile Leu Ala Leu Pro Ile Leu Gly Ile Thr Ile Gly Arg Met
450                 455                 460

Val Gln Asn Phe Glu Leu Leu Pro Pro Pro Gly Gln Ser Lys Val Asp
465                 470                 475                 480

Thr Ser Glu Lys Gly Gly Gln Phe Ser Leu His Ile Leu Asn His Ser
                485                 490                 495

Ile Ile Val Met Lys Pro Arg Asn Cys
            500                 505

<210> SEQ ID NO 13
<211> LENGTH: 2136
<212> TYPE: DNA
<213> ORGANISM: Arabidopsis thaliana

<400> SEQUENCE: 13
atgtcctctt cttcttcttc gtcaacctcc atgatcgatc tcatggcagc aatcatcaaa      60
ggagagcctg taattgtctc cgacccagct aatgcctccg cttacgagtc cgtagctgct     120
gaattatcct ctatgcttat agagaatcgt caattcgcca tgattgttac cacttccatt     180
gctgttctta ttggttgcat cgttatgctc gtttggagga gatccggttc tgggaattca     240
aaacgtgtcg agcctcttaa gcctttggtt attaagcctc gtgaggaaga gattgatgat     300
gggcgtaaga agttaccat cttttttcggt acacaaactg gtactgctga aggttttgca     360
aaggctttag agaagaagc taaagcaaga tatgaaaaga ccagattcaa atcgttgat     420 ttggatgatt acgcggctga tgatgatgag tatgaggaga aattgaagaa agaggatgtg     480
gctttcttct tcttagccac atatggagat ggtgagccta ccgacaatgc agcgagattc     540
tacaaatggt tcaccgaggg gaatgacaga ggagaatggc ttaagaactt gaagtatgga     600
gtgtttggat taggaaacag acaatatgag cattttaata aggttgccaa agttgtagat     660
gacattcttg tcgaacaagg tgcacagcgt cttgtacaag ttggtcttgg agatgatgac     720
cagtgtattg aagatgactt taccgcttgg cgagaagcat gtggcccga gcttgataca     780 atactgaggg aagaagggga tacagctgtt gccacaccat acactgcagc tgtgttagaa     840
tacagagttt ctattcacga ctctgaagat gccaaattca atgatataaa catggcaaat     900
gggaatggtt acactgtgtt tgatgctcaa catccttaca agcaaatgt cgctgttaaa     960
```

```
agggagcttc atactcccga gtctgatcgt tcttgtatcc atttggaatt tgacattgct   1020
ggaagtggac ttacgtatga aactggagat catgttggtg tactttgtga taacttaagt   1080
gaaactgtag atgaagctct tagattgctg gatatgtcac ctgatactta tttctcactt   1140
cacgctgaaa aagaagacgg cacaccaatc agcagctcac tgcctcctcc cttcccacct   1200
tgcaacttga aacagcgct tacacgatat gcatgtcttt tgagttctcc aaagaagtct   1260
gctttagttg cgttggctgc tcatgcatct gatcctaccg aagcagaacg attaaaacac   1320
cttgcttcac ctgctggaaa ggatgaatat tcaaagtggg tagtagagag tcaaagaagt   1380
ctacttgagg tgatggccga gtttccttca gccaagccac cacttggtgt cttcttcgct   1440
ggagttgctc aaggttgca gcctaggttc tattcgatat catcatcgcc aagattgct   1500 gaaactagaa ttcacgtcac atgtgcactg gtttatgaga aaatgccaac tggcaggatt   1560
cataagggag tgtgttccac ttggatgaag aatgctgtgc cttacgagaa gagtgaaaac   1620
tgttcctcgg cgccgatatt tgttaggcaa tccaacttca agcttccttc tgattctaag   1680
gtaccgatca tcatgatcgg tccagggact ggattagctc cattcagagg attccttcag   1740
gaaagactag cgttggtaga atctggtgtt gaacttgggc catcagtttt gttctttgga   1800
tgcagaaacc gtagaatgga tttcatctac gaggaagagc tccagcgatt tgttgagagt   1860
ggtgctctcg cagagctaag tgtcgccttc tctcgtgaag acccaccaa agaatacgta   1920 cagcacaaga tgatggacaa ggcttctgat atctggaata tgatctctca aggagcttat   1980
ttatatgttt tgtggtgacgc caaaggcatg gcaagagatg ttcacagatc tctccacaca   2040
atagctcaag aacaggggtc aatggattca actaaagcag agggcttcgt gaagaatctg   2100
caaacgagtg aagatatct tagagatgta tggtaa                              2136
```

<210> SEQ ID NO 14
<211> LENGTH: 711
<212> TYPE: PRT
<213> ORGANISM: Arabidopsis thaliana

<400> SEQUENCE: 14

```
Met Ser Ser Ser Ser Ser Ser Thr Ser Met Ile Asp Leu Met Ala
 1               5                  10                  15

Ala Ile Ile Lys Gly Glu Pro Val Ile Val Ser Asp Pro Ala Asn Ala
             20                  25                  30

Ser Ala Tyr Glu Ser Val Ala Ala Glu Leu Ser Ser Met Leu Ile Glu
         35                  40                  45

Asn Arg Gln Phe Ala Met Ile Val Thr Thr Ser Ile Ala Val Leu Ile
     50                  55                  60

Gly Cys Ile Val Met Leu Val Trp Arg Arg Ser Gly Ser Gly Asn Ser
 65                  70                  75                  80

Lys Arg Val Glu Pro Leu Lys Pro Leu Val Ile Lys Pro Arg Glu Glu
                 85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160
```

```
Ala Phe Phe Phe Leu Ala Thr Tyr Gly Asp Gly Glu Pro Thr Asp Asn
            165                 170                 175

Ala Ala Arg Phe Tyr Lys Trp Phe Thr Glu Gly Asn Asp Arg Gly Glu
        180                 185                 190

Trp Leu Lys Asn Leu Lys Tyr Gly Val Phe Gly Leu Gly Asn Arg Gln
    195                 200                 205

Tyr Glu His Phe Asn Lys Val Ala Lys Val Val Asp Asp Ile Leu Val
210                 215                 220

Glu Gln Gly Ala Gln Arg Leu Val Gln Val Gly Leu Gly Asp Asp Asp
225                 230                 235                 240

Gln Cys Ile Glu Asp Phe Thr Ala Trp Arg Glu Ala Leu Trp Pro
                245                 250                 255

Glu Leu Asp Thr Ile Leu Arg Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Asn Cys Ser Ser Ala
    530                 535                 540

Pro Ile Phe Val Arg Gln Ser Asn Phe Lys Leu Pro Ser Asp Ser Lys
545                 550                 555                 560

Val Pro Ile Ile Met Ile Gly Pro Gly Thr Gly Leu Ala Pro Phe Arg
                565                 570                 575
```

```
Gly Phe Leu Gln Glu Arg Leu Ala Leu Val Glu Ser Gly Val Glu Leu
            580                 585                 590

Gly Pro Ser Val Leu Phe Phe Gly Cys Arg Asn Arg Met Asp Phe
        595                 600                 605

Ile Tyr Glu Glu Leu Gln Arg Phe Val Glu Ser Gly Ala Leu Ala
    610                 615                 620

Glu Leu Ser Val Ala Phe Ser Arg Glu Gly Pro Thr Lys Glu Tyr Val
625                 630                 635                 640

Gln His Lys Met Met Asp Lys Ala Ser Asp Ile Trp Asn Met Ile Ser
                645                 650                 655

Gln Gly Ala Tyr Leu Tyr Val Cys Gly Asp Ala Lys Gly Met Ala Arg
            660                 665                 670

Asp Val His Arg Ser Leu His Thr Ile Ala Gln Glu Gln Gly Ser Met
        675                 680                 685

Asp Ser Thr Lys Ala Glu Gly Phe Val Lys Asn Leu Gln Thr Ser Gly
    690                 695                 700

Arg Tyr Leu Arg Asp Val Trp
705                 710

<210> SEQ ID NO 15
<211> LENGTH: 1169
<212> TYPE: DNA
<213> ORGANISM: Medicago truncatula

<400> SEQUENCE: 15
atggttagtg tgtctgaaat tcgcaatgct caaagggcag aaggccctgc aaccatttta      60
gccattggca ctgcaaaccc agccaattgt gttgaacaaa gcacatatcc tgatttctac     120
ttcaaaatca caaatagtga acacaagact gaactcaaag agaaattcca acgcatgtgt     180
gataaatcta tgatcaagag gagatatatg tacctaacag aggagatttt gaaagagaat     240
cctagtgttt gtgaatacat ggcaccttca ttggatgcta ggcaagacat ggtggtggta     300
gaggtaccta gactagggaa ggaggctgca gtgaaggcca taaagaatg gggtcaacca     360 aagtcaaaga ttactcactt gatcgtttgc accacaagtg gtgtagacat gcctggagct     420
gattaccaac tcacaaaact cttaggtctt cgcccatatg tgaaaaggta tatgatgtac     480
caacaaggtt gctttgcagg aggcacggtc cttcgtttgg ctaaagattt agctgaaaac     540
aacaaaggtg ctcgtgtgtt ggttgtctgt tctgaagtca ctgcagtcac atttcgcggc     600
cctagtgata ctcacttgga cagccttgtt ggacaagcac tatttggaga tggagctgct     660
gcactaattg ttggttcaga tccagtacca gaaattgaga accaatatt tgagatggtt     720 tggactgcac aaacaattgc tccagatagt gaaggagcca ttgatggtca ccttcgtgaa     780
gctggactaa catttcacct tcttaaagat gttcctggga ttgtttcaaa gaacatcaat     840
aaagcattgg ttgaggcttt tgaaccatta ggaattctg attacaattc aatcttttgg     900
attgcacacc ctggtggacc tgcaattcta gatcaagttg agcaaaagtt agccttaaag     960
cctgaaaaga tgaaagccac cagagaagtg cttagtgaat atggaaatat gtcaagtgcc    1020
tgtgttttgt ttatcttaga tgaaatgaga aagaagtcag ctcaagatgg attgaagacc    1080
acaggagaag gacttgaatt tggtgttttta tttggctttg accgggtctt taccattgaa    1140
actgttgttt tgcgaagtat cgctatatg                                       1169

<210> SEQ ID NO 16
<211> LENGTH: 389
<212> TYPE: PRT
```

<213> ORGANISM: Medicago truncatula

<400> SEQUENCE: 16

```
Met Val Ser Val Ser Glu Ile Arg Asn Ala Gln Arg Ala Glu Gly Pro
1               5                   10                  15

Ala Thr Ile Leu Ala Ile Gly Thr Ala Asn Pro Ala Asn Cys Val Glu
            20                  25                  30

Gln Ser Thr Tyr Pro Asp Phe Tyr Phe Lys Ile Thr Asn Ser Glu His
        35                  40                  45

Lys Thr Glu Leu Lys Glu Lys Phe Gln Arg Met Cys Asp Lys Ser Met
    50                  55                  60

Ile Lys Arg Arg Tyr Met Tyr Leu Thr Glu Glu Ile Leu Lys Glu Asn
65                  70                  75                  80

Pro Ser Val Cys Glu Tyr Met Ala Pro Ser Leu Asp Ala Arg Gln Asp
                85                  90                  95

Met Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
        115                 120                 125

Val Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ser Asp Pro Val Pro Glu Ile Glu Lys Pro Ile Phe Glu Met Val
225                 230                 235                 240

Trp Thr Ala Gln Thr Ile Ala Pro Asp Ser Glu Gly Ala Ile Asp Gly
                245                 250                 255

His Leu Arg Glu Ala Gly Leu Thr Phe His Leu Leu Lys Asp Val Pro
            260                 265                 270

Gly Ile Val Ser Lys Asn Ile Asn Lys Ala Leu Val Glu Ala Phe Glu
        275                 280                 285

Pro Leu Gly Ile Ser Asp Tyr Asn Ser Ile Phe Trp Ile Ala His Pro
    290                 295                 300

Gly Gly Pro Ala Ile Leu Asp Gln Val Glu Gln Lys Leu Ala Leu Lys
305                 310                 315                 320

Pro Glu Lys Met Lys Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Ala Gln Asp Gly Leu Lys Thr Thr Gly Glu Gly Leu Glu Phe Gly
        355                 360                 365

Val Leu Phe Gly Phe Gly Pro Gly Leu Thr Ile Glu Thr Val Val Leu
    370                 375                 380

Arg Ser Ile Ala Ile
385
```

<210> SEQ ID NO 17
<211> LENGTH: 1170
<212> TYPE: DNA
<213> ORGANISM: Medicago truncatula

<400> SEQUENCE: 17

```
atggtgagtg tatctgaaat tcgcaaggct caaagggcag aaggtcctgc aaccatattg      60
gccattggca ctgcaaatcc agcaaactgt gttgaacaaa gcacatatcc tgattttttac   120
tttaaaatca aaatagcga acacaaaact gagctcaaag aaaaatttca acgcatgtgt      180
gacaaatcca tgatcaaaag aagatacatg tatctaacag aggagatttt aaaagagaat    240
cctaatgttt gtgaatacat ggcaccttca ttggatgcta acaagacat ggtggtggta      300
gaagtaccta ctagggaa ggaggctgca gtgaaggcta taaaagaatg ggtcaacca         360
aagtcaaaga ttactcactt aatcgtttgc accacaagcg tgtagacat gcctggggcc       420
gattatcaac tcactaaact cttaggtctt cgtccatatg taaaagata catgatgtac       480
cagcaaggtt gttttgcagg tggcacggta cttcgtttgg ctaaggattt ggctgagaac     540
aacaaaggtg ctcgtgtgtt agttgtttgt tctgaagtca ctgcagtcac atttcgtggt    600
cccagtgata cacacttgga cagtcttgtt ggacaagcac atttggaga tggagcagct      660
gcacttattg ttgggtctga tccggtacca gaaattgaaa aacctatatt tgagatgatt     720
tggacagcac aaacaattgc tcctgatagt gaaggtgcca ttgatggtca tcttcgtgaa    780
gctgggttaa catttcacct tcttaaagat gttcctggga ttgtgtcaaa aaatataaat    840
aaagcattag ttgaggcttt ccaaccattg gaatctctg attacaactc aatcttttgg     900
attgcacacc ctggtggacc tgcaatttta gaccaagtag agcaaaagtt agccttaaag    960
cccgaaaaga tgagagccac acgggaggtg ctaagtgaat atggaaatat gtcaagtgca   1020
tgtgtattgt ttatcttgga tgaaatgaga aagaaatcaa ctcaaaatgg tttgaagaca   1080
accggagaag ggcatgaatg gggtgtgcta ttcggctttg gaccaggact taccattgag   1140
actgttgtct gcgcagtgt agctatataa                                       1170
```

<210> SEQ ID NO 18
<211> LENGTH: 389
<212> TYPE: PRT
<213> ORGANISM: Medicago truncatula

<400> SEQUENCE: 18

Met Val Ser Val Ser Glu Ile Arg Lys Ala Gln Arg Ala Glu Gly Pro
1               5                   10                  15

Ala Thr Ile Leu Ala Ile Gly Thr Ala Asn Pro Ala Asn Cys Val Glu
            20                  25                  30

Gln Ser Thr Tyr Pro Asp Phe Tyr Phe Lys Ile Thr Asn Ser Glu His
        35                  40                  45

Lys Thr Glu Leu Lys Glu Lys Phe Gln Arg Met Cys Asp Lys Ser Met
    50                  55                  60

Ile Lys Arg Arg Tyr Met Tyr Leu Thr Glu Glu Ile Leu Lys Glu Asn
65                  70                  75                  80

Pro Asn Val Cys Glu Tyr Met Ala Pro Ser Leu Asp Ala Arg Gln Asp
                85                  90                  95

Met Val Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
        115                 120                 125

-continued

Val Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
            165                 170                 175

Leu Ala Glu Asn Asn Lys Gly Ala Arg Val Leu Val Cys Ser Glu
        180                 185                 190

Val Thr Ala Val Thr Phe Arg Gly Pro Ser Asp Thr His Leu Asp Ser
    195                 200                 205

Leu Val Gly Gln Ala Leu Phe Gly Asp Gly Ala Ala Leu Ile Val
    210                 215                 220

Gly Ser Asp Pro Val Pro Glu Ile Glu Lys Pro Ile Phe Glu Met Ile
225                 230                 235                 240

Trp Thr Ala Gln Thr Ile Ala Pro Asp Ser Glu Gly Ala Ile Asp Gly
            245                 250                 255

His Leu Arg Glu Ala Gly Leu Thr Phe His Leu Leu Lys Asp Val Pro
        260                 265                 270

Gly Ile Val Ser Lys Asn Ile Asn Lys Ala Leu Val Glu Ala Phe Gln
    275                 280                 285

Pro Leu Gly Ile Ser Asp Tyr Asn Ser Ile Phe Trp Ile Ala His Pro
    290                 295                 300

Gly Gly Pro Ala Ile Leu Asp Gln Val Glu Gln Lys Leu Ala Leu Lys
305                 310                 315                 320

Pro Glu Lys Met Arg Ala Thr Arg Glu Val Leu Ser Glu Tyr Gly Asn
            325                 330                 335

Met Ser Ser Ala Cys Val Leu Phe Ile Leu Asp Glu Met Arg Lys Lys
        340                 345                 350

Ser Thr Gln Asn Gly Leu Lys Thr Thr Gly Glu Gly His Glu Trp Gly
    355                 360                 365

Val Leu Phe Gly Phe Gly Pro Gly Leu Thr Ile Glu Thr Val Val Leu
370                 375                 380

Arg Ser Val Ala Ile
385

<210> SEQ ID NO 19
<211> LENGTH: 1176
<212> TYPE: DNA
<213> ORGANISM: Medicago truncatula

<400> SEQUENCE: 19
atggtgactg tggaggagat tcgtaaggct caacgttcca atggccctgc cactatcttg      60
gcttttggca ctgccactcc ttctcactgt gtcactcaag ctgaatatcc tgattactac     120
tttcgtatca ccaacagtga gcacatgact gaccttaagg aaaaattcaa gcgcatgtgt     180
gaaaaatcga tgataaagaa acgttacatg cacataacag aagaatttct gaaagagaat     240
ccaaacatgt gtgcatacat ggcaccatca ctagacgcaa acaagattt agtggtagtg     300 gaagtaccaa agctaggtaa agatgctgca aaaaagcca tagctgaatg ggtcaaccca     360
aaatccaaaa tcacccacgt agtttctgc acaacttctg gtgtagacat gccgggtgcc     420
gattaccaac tcactaaact cttaggccta aaaccatctg tcaaacgtct catgatgtat     480
caacaaggtt gttcgcagg cggcacagtt ctccgcttag cgaaagatct tgctgagaat     540
aacaaaaatg caagagttct tgttgtttgt ctgaaatca ctgcagttac tttccgtggt     600

```
ccatcagata ctcatttaga ttcacttgta ggacaggcgc tcttcggtga tggagccgca    660
gcaatgatta ttggtgcgga tccagattta accgtggagc gtccgatttt tgagattgtc    720
tcggctgctc agactattct tcctgattct gatggcgcga ttgacggaca tctccgtgaa    780 gtttgggctca cttttcatct tctcaaagat gttcctggaa ttatctcaaa gaatattgaa    840
aagagtttgg ttgaggcttt tgcaccaatt ggaataagtg attggaattc gatcttttgg    900
gttgcacatc caggtggacc ggctatttta gaccaggttg aagaaaaact ccgtcttaag    960
gaggagaaac tccggtccac ccggcacgtg cttagtgaat atggaaatat gtcgagtgct   1020
tgtgttttgt ttattttgga tgaaatgaga aagaggtcta aggaggaagg aaagattaca   1080
accggtgaag ggttggaatg gggtgttttg tttgggtttg gaccgggttt aaccgttgag   1140
acagttgtgc ttcatagtgt tccggttcag ggttaa                            1176

<210> SEQ ID NO 20
<211> LENGTH: 391
<212> TYPE: PRT
<213> ORGANISM: Medicago truncatula

<400> SEQUENCE: 20

Met Val Thr Val Glu Glu Ile Arg Lys Ala Gln Arg Ser Asn Gly Pro
  1               5                  10                  15

Ala Thr Ile Leu Ala Phe Gly Thr Ala Thr Pro Ser His Cys Val Thr
                 20                  25                  30

Gln Ala Glu Tyr Pro Asp Tyr Tyr Phe Arg Ile Thr Asn Ser Glu His
             35                  40                  45

Met Thr Asp Leu Lys Glu Lys Phe Lys Arg Met Cys Glu Lys Ser Met
         50                  55                  60

Ile Lys Lys Arg Tyr Met His Ile Thr Glu Glu Phe Leu Lys Glu Asn
 65                  70                  75                  80

Pro Asn Met Cys Ala Tyr Met Ala Pro Ser Leu Asp Ala Arg Gln Asp
                 85                  90                  95

Leu Val Val Val Glu Val Pro Lys Leu Gly Lys Asp Ala Ala Lys Lys
            100                 105                 110

Ala Ile Ala Glu Trp Gly Gln Pro Lys Ser Lys Ile Thr His Val Val
        115                 120                 125

Phe Cys Thr Thr Ser Gly Val Asp Met Pro Gly Ala Asp Tyr Gln Leu
    130                 135                 140

Thr Lys Leu Leu Gly Leu Lys Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Asn Ala Arg Val Leu Val Val Cys Ser Glu
            180                 185                 190

Ile Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Met Ile Ile
    210                 215                 220

Gly Ala Asp Pro Asp Leu Thr Val Glu Arg Pro Ile Phe Glu Ile Val
225                 230                 235                 240

Ser Ala Ala Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
            260                 265                 270
```

Gly Ile Ile Ser Lys Asn Ile Glu Lys Ser Leu Val Glu Ala Phe Ala
            275                 280                 285

Pro Ile Gly Ile Ser Asp Trp Asn Ser Ile Phe Trp Val Ala His Pro
        290                 295                 300

Gly Gly Pro Ala Ile Leu Asp Gln Val Glu Glu Lys Leu Arg Leu Lys
305                 310                 315                 320

Glu Glu Lys Leu Arg Ser Thr Arg His Val Leu Ser Glu Tyr Gly Asn
                325                 330                 335

Met Ser Ser Ala Cys Val Leu Phe Ile Leu Asp Glu Met Arg Lys Arg
            340                 345                 350

Ser Lys Glu Glu Gly Lys Ile Thr Thr Gly Glu Gly Leu Glu Trp Gly
        355                 360                 365

Val Leu Phe Gly Phe Gly Pro Gly Leu Thr Val Glu Thr Val Val Leu
370                 375                 380

His Ser Val Pro Val Gln Gly
385                 390

<210> SEQ ID NO 21
<211> LENGTH: 1169
<212> TYPE: DNA
<213> ORGANISM: Medicago truncatula

<400> SEQUENCE: 21
atggtgagtg tatctgaaat tcgcaaggct cagagggcag aaggccctgc caccatcatg      60
gccattggca ctgcaaatcc agccaactgt gttgaacaaa gcacatatcc tgattttttac    120
ttcaaaatca aaacagtga gcacaaagtt gaacttaaag aaaaatttca acgcatgtgt      180
gataaatcca tgatcaagag gagatacatg tatcttaccg aagaaatttt gaagaaaat     240
ccaagtgtat gtgaatacat ggcaccgtca ttggatgcta ggcaggacat ggtggtggta    300
gaagtaccta gactaggaaa ggaggctgca gtgaaagcta taaagaatg gggccaacca     360
aaatcaaaga ttacacactt gatcttttgc accacaagtg gtgtagacat gcctggcgct    420
gattaccaac tcaccaaact cttaggtctt cgtccatatg tgaagaggta tatgatgtac    480
caacaaggat gttttgcagg tgggacggtg cttcgtttgg ccaaggactt ggctgagaac    540
aataaaggtg ctcgtgtgtt ggttgttttgt tctgaagtta ctgcagtgac attccgtggt    600
cctagtgata ctcatttgga cagtcttgtt ggacaagcac tatttggaga tggtgctgct    660
gcactcattg ttggttctga cccaatacca gaaattgaga aacctatatt tgagatggtt    720
tggactgcac aaacaattgc tccagacagt gagggagcca ttgatggtca ccttcgtgaa    780
gctggtctaa catttcacct tcttaaagat gttcctggga ttgtttcaaa gaacattgat    840
aaagcattgg tcgaggcttt ccaaccatta acatctctg attataattc aatcttctgg    900
attgctcacc aggtggacc cgcaattcta gaccaagttg aagaaaagtt aggcttaaaa    960
cctgaaaaaa tgaaggccac tagggaagta cttagtgaat atggtaacat gtcaagcgca   1020
tgtgtattgt tcatcttgga tgagatgaga aagaaatcgg ctcaagaggg acttaaaacc   1080
acaggtgaag gccttgactg gggtgtgttg tttggctttg gacctggact caccattgaa   1140
acagttgttc tccatagcgt ggctatata                                       1169

<210> SEQ ID NO 22
<211> LENGTH: 389
<212> TYPE: PRT
<213> ORGANISM: Medicago truncatula

```
<400> SEQUENCE: 22

Met Val Ser Val Ser Glu Ile Arg Lys Ala Gln Arg Ala Glu Gly Pro
1               5                   10                  15

Ala Thr Ile Met Ala Ile Gly Thr Ala Asn Pro Ala Asn Cys Val Glu
            20                  25                  30

Gln Ser Thr Tyr Pro Asp Phe Tyr Phe Lys Ile Thr Asn Ser Glu His
        35                  40                  45

Lys Val Glu Leu Lys Glu Lys Phe Gln Arg Met Cys Asp Lys Ser Met
    50                  55                  60

Ile Lys Arg Arg Tyr Met Tyr Leu Thr Glu Glu Ile Leu Lys Glu Asn
65                  70                  75                  80

Pro Ser Val Cys Glu Tyr Met Ala Pro Ser Leu Asp Ala Arg Gln Asp
                85                  90                  95

Met Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
            115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ser Asp Pro Ile Pro Glu Ile Glu Lys Pro Ile Phe Glu Met Val
225                 230                 235                 240

Trp Thr Ala Gln Thr Ile Ala Pro Asp Ser Glu Gly Ala Ile Asp Gly
                245                 250                 255

His Leu Arg Glu Ala Gly Leu Thr Phe His Leu Leu Lys Asp Val Pro
            260                 265                 270

Gly Ile Val Ser Lys Asn Ile Asp Lys Ala Leu Val Glu Ala Phe Gln
        275                 280                 285

Pro Leu Asn Ile Ser Asp Tyr Asn Ser Ile Phe Trp Ile Ala His Pro
    290                 295                 300

Gly Gly Pro Ala Ile Leu Asp Gln Val Glu Glu Lys Leu Gly Leu Lys
305                 310                 315                 320

Pro Glu Lys Met Lys Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Ala Gln Glu Gly Leu Lys Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

His Ser Val Ala Ile
385

<210> SEQ ID NO 23
```

<211> LENGTH: 1169
<212> TYPE: DNA
<213> ORGANISM: Medicago truncatula

<400> SEQUENCE: 23

```
atggtgacat ttgatgagat ccgccaggca cagagggctg atggccctgc caccgtgttg      60
gcaatcggca ctgcaactcc tcaaaactgc gtggaccaga gcatacccc tgactactat     120
ttccgcatca caaacagtga acataagact gagctcaaag aaaaatttca gcgcatgtgt    180
gataagtcaa tgatcaagaa gagatacatg tacttgacag aagagatcct gaaagagaat    240
ccaagtgtat gcgagtacat ggcaccttca ttggatgcaa gacaagacat ggtggttgtg    300
gaggtaccaa gactaggaaa agaggcagca acaaaggcca tcaaggaatg gggtcaacct    360
aagtccaaga ttacccacct catcttttgc accaccagtg gcgtggacat gcccggtgcc    420
gactatcagc tgacaaagct cttgggcctt cgtccatatg tgaagcgtta catgatgtac    480
caacaaggtt gttttgctgg tggcacggtg cttcgtttgg ctaaagactt ggctgaaaac    540
aacaaaggtg ctcgtgtgtt ggtagtttgt tcagagataa ctgcagttac tttccgtgga    600
cccagtgaca ctcatcttga tagccttgtg gggcaagcat tgtttggaga tggtgcagca    660
gctgtgatcg taggttcaga cccattacca caagttgaga acccttgtt tgaattggta    720
tggactgcac aaacgatcct tccagatagt gaaggagcaa ttgacggtca ccttcgtgaa    780
gtcgggctta cattccatct cctcaaggat gttcctggtc ttatctcaaa gaacattgag    840
aaagctcttg ctgaggcctt tcaacccttta ggtatctctg attacaattc catcttttgg    900
atcgcacacc ctggtggacc agcaattctg gaccaagtgg aagccaaatt aagcttaaag    960
ccagagaaaa tgcaagccac tcgacatgtg cttagcgagt atggtaacat gtcaagtgca   1020
tgtgtgttat tcatcttgga tgagatgagg aggaagtcaa agaagacgg acttgccaca   1080
acaggcgagg ggctggaatg gggtgtccta tttggtttcg ggcccggact cactgttgag   1140
actgtagtgc tccacagtgt tgccactta                                       1169
```

<210> SEQ ID NO 24
<211> LENGTH: 389
<212> TYPE: PRT
<213> ORGANISM: Medicago truncatula

<400> SEQUENCE: 24

```
Met Val Thr Phe Asp Glu Ile Arg Gln Ala Gln Arg Ala Asp Gly Pro
  1               5                  10                  15
Ala Thr Val Leu Ala Ile Gly Thr Ala Thr Pro Gln Asn Cys Val Asp
             20                  25                  30
Gln Ser Thr Tyr Pro Asp Tyr Tyr Phe Arg Ile Thr Asn Ser Glu His
         35                  40                  45
Lys Thr Glu Leu Lys Glu Lys Phe Gln Arg Met Cys Asp Lys Ser Met
     50                  55                  60
Ile Lys Lys Arg Tyr Met Tyr Leu Thr Glu Glu Ile Leu Lys Glu Asn
 65                  70                  75                  80
Pro Ser Val Cys Glu Tyr Met Ala Pro Ser Leu Asp Ala Arg Gln Asp
                 85                  90                  95
Met Val Val Val Glu Val Pro Arg Leu Gly Lys Glu Ala Ala Thr Lys
            100                 105                 110
Ala Ile Lys Glu Trp Gly Gln Pro Lys Ser Lys Ile Thr His Leu Ile
        115                 120                 125
```

```
Phe Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Val Ile Val
210                 215                 220

Gly Ser Asp Pro Leu Pro Gln Val Glu Lys Pro Leu Phe Glu Leu Val
225                 230                 235                 240

Trp Thr Ala Gln Thr Ile Leu Pro Asp Ser Glu Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ala Leu Ala Glu Ala Phe Gln
        275                 280                 285

Pro Leu Gly Ile Ser Asp Tyr Asn Ser Ile Phe Trp Ile Ala His Pro
290                 295                 300

Gly Gly Pro Ala Ile Leu Asp Gln Val Glu Ala Lys Leu Ser Leu Lys
305                 310                 315                 320

Pro Glu Lys Met Gln Ala Thr Arg His Val Leu Ser Glu Tyr Gly Asn
                325                 330                 335

Met Ser Ser Ala Cys Val Leu Phe Ile Leu Asp Glu Met Arg Arg Lys
            340                 345                 350

Ser Lys Glu Asp Gly Leu Ala Thr Thr Gly Glu Gly Leu Glu Trp Gly
        355                 360                 365

Val Leu Phe Gly Phe Gly Pro Gly Leu Thr Val Glu Thr Val Val Leu
370                 375                 380

His Ser Val Ala Thr
385

<210> SEQ ID NO 25
<211> LENGTH: 1176
<212> TYPE: DNA
<213> ORGANISM: Rheum tataricum

<400> SEQUENCE: 25
atggcaccgg aggagtccag gcatgctgaa actgcagtta acagagccgc caccgtcctg      60
gccatcggca ctgccaaccc gccaaactgc tactatcaag cggactttcc tgacttctac     120
ttccgtgcca ccaacagcga ccacctcacg cacctcaagc aaaaatttaa gcgcatttgt     180
gagaaatcga tgattgaaaa acgttatctc catttgacgg aagaaattct caaggagaat     240
ccaaatattg cttccttcga ggcgccatca ttggatgtaa acataacat tcaagtgaaa     300 gaagtggtgc tgctcggaaa agaggcagct ttgaaggcca tcaatgagtg gggccaaccc     360
aagtcaaaga tcacgcgcct cattgtgtgt gtattgccg cgttgacat gcccggcgca     420 gactatcaac tcactaaact ccttggctta caactttctg ttaagcgatt tatgttttac     480
cacctaggat gctatgccgg tggcaccgtc cttcgccttg cgaaggacat agcagaaaac     540
aacaaggaag ctcgtgttct catcgttcgc tctgagatga cgccaatctg tttccgtggg     600
```

```
ccatccgaaa cccacataga ctccatggta gggcaagcaa tatttggtga cggtgctgcg   660
gctgttatag ttggtgcaaa tcccgaccta tccatcgaaa ggccgatttt cgagttgatt   720
tctacatccc aaactatcat acctgaatcc gatggtgcga ttgagggaca tttgcttgaa   780
gttggactca gtttccaact ctaccagact gttccctcat taatctctaa ttgtatcgaa   840
acttgtcttt caaaggcttt cacacctctt aacattagtg attggaactc actattctgg   900
attgcacacc ctggtggccg tgctatcctt gacgatatcg aggctactgt tggtctcaag   960
aaggagaaac ttaaggcaac aagacaagtt ttgaacgact atgggaacat gtcaagtgct  1020
tgcgtatttt tcatcatgga tgagatgagg aagaagtcgc tcgcaaacgg tcaagtaacc  1080
actggagaag gactcaagtg gggtgttctt tttgggttcg ggccaggtgt tactgtggaa  1140
actgtggttc taagcagtgt gccgctaatt acctga                             1176
```

<210> SEQ ID NO 26
<211> LENGTH: 391
<212> TYPE: PRT
<213> ORGANISM: Rheum tataricum

<400> SEQUENCE: 26

```
Met Ala Pro Glu Glu Ser Arg His Ala Glu Thr Ala Val Asn Arg Ala
  1               5                  10                  15

Ala Thr Val Leu Ala Ile Gly Thr Ala Asn Pro Pro Asn Cys Tyr Tyr
             20                  25                  30

Gln Ala Asp Phe Pro Asp Phe Tyr Phe Arg Ala Thr Asn Ser Asp His
         35                  40                  45

Leu Thr His Leu Lys Gln Lys Phe Lys Arg Ile Cys Glu Lys Ser Met
     50                  55                  60

Ile Glu Lys Arg Tyr Leu His Leu Thr Glu Glu Ile Leu Lys Glu Asn
 65                  70                  75                  80

Pro Asn Ile Ala Ser Phe Glu Ala Pro Ser Leu Asp Val Arg His Asn
                 85                  90                  95

Ile Gln Val Lys Glu Val Val Leu Leu Gly Lys Glu Ala Ala Leu Lys
            100                 105                 110

Ala Ile Asn Glu Trp Gly Gln Pro Lys Ser Lys Ile Thr Arg Leu Ile
        115                 120                 125

Val Cys Cys Ile Ala Gly Val Asp Met Pro Gly Ala Asp Tyr Gln Leu
    130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                165                 170                 175

Ile Ala Glu Asn Asn Lys Glu Ala Arg Val Leu Ile Val Arg Ser Glu
            180                 185                 190

Met Thr Pro Ile Cys Phe Arg Gly Pro Ser Glu Thr His Ile Asp Ser
        195                 200                 205

Met Val Gly Gln Ala Ile Phe Gly Asp Gly Ala Ala Ala Val Ile Val
    210                 215                 220

Gly Ala Asn Pro Asp Leu Ser Ile Glu Arg Pro Ile Phe Glu Leu Ile
225                 230                 235                 240

Ser Thr Ser Gln Thr Ile Ile Pro Glu Ser Asp Gly Ala Ile Glu Gly
                245                 250                 255

His Leu Leu Glu Val Gly Leu Ser Phe Gln Leu Tyr Gln Thr Val Pro
            260                 265                 270
```

Ser Leu Ile Ser Asn Cys Ile Glu Thr Cys Leu Ser Lys Ala Phe Thr
            275                 280                 285

Pro Leu Asn Ile Ser Asp Trp Asn Ser Leu Phe Trp Ile Ala His Pro
        290                 295                 300

Gly Gly Arg Ala Ile Leu Asp Asp Ile Glu Ala Thr Val Gly Leu Lys
305                 310                 315                 320

Lys Glu Lys Leu Lys Ala Thr Arg Gln Val Leu Asn Asp Tyr Gly Asn
                325                 330                 335

Met Ser Ser Ala Cys Val Phe Phe Ile Met Asp Glu Met Arg Lys Lys
            340                 345                 350

Ser Leu Ala Asn Gly Gln Val Thr Thr Gly Glu Gly Leu Lys Trp Gly
        355                 360                 365

Val Leu Phe Gly Phe Gly Pro Gly Val Thr Val Glu Thr Val Val Leu
    370                 375                 380

Ser Ser Val Pro Leu Ile Thr
385                 390

<210> SEQ ID NO 27
<211> LENGTH: 1212
<212> TYPE: DNA
<213> ORGANISM: Psilotum nudum

<400> SEQUENCE: 27

```
atgaccaccg gtgaggccag ccttatgaag aatggtccag catcccgcgc gcgcagagag      60
gagagagcag atggtccggc tactgagcta gccattggca ccgccaatcc gtccaatgtg     120
ttcgatcagg aaacgtatcc tgacttttac ttcgacgtta ccaacaacac tgataagcct     180
gagttgaagg ccaaattcca gcgcatgtgt aacagtctgg aatccaaaaa ggtacatgtg     240
cttcacggag gagacgttga aggccaacct agtatggtgt ttattggcag aattcttctt     300
gacgtgagac aaggacgtcg tagcagagca agtgctaagt tggcaaaaga ggcatccctg     360
aaggctttga gagagtgggg tcagcccaat tccaagatca cccatttggt cttctgcacc     420
accgctccag ttaccctgcc tggagtagat gctgccctga tacagagttt aggcctgaat     480
ccttcggtca gcgggttcct gctttacatg cagggctgct tcgcaggtgg tacggtgctc     540
agacatgcca aggaccttgc agagaacaac agaggcgccc gagtcttagt ggtgtgcagc     600
gagacgaccg cagtcacatt ccgcgggccg catgaaaatc atcttgacaa tctagtagga     660
caagccttgt ttgcggatgg ggcatcggcc ctgatagtag gctcggatcc aatttcagat     720
cttgagaagc cgtggtttga gataaggtgg gcaggatcgt acttgattcc ggaaagcggc     780
caagctattg cagggcagct caaggaagtg gggcttgaat tcatctgac agagatgtc     840
tctgggttgg tctcgaagaa cattgtaacg attctaaacg aggccttcga gggaacagga     900
ataaccgact ggaatgatat atttatcatt ccacatcccg gaggcccagc cattctcgac     960
gtaatacagg acagactgaa gctgcaacct gagaagctac aagcgagccg ccatgtgctg    1020
gccgaattcg gcaacatgtc cagcgctact gttcatttta gtttggacca gatgagaagg    1080
tcttctgtag agaaggggtg ttccaccacc ggtgagggct acgaattggg aattctactt    1140
gggttaggac cgggaatgac agtggaatct atcctcttga agagtgtacc cacatggaca    1200
gtagcttcat ag                                                        1212
```

<210> SEQ ID NO 28
<211> LENGTH: 403
<212> TYPE: PRT
<213> ORGANISM: Psilotum nudum

<400> SEQUENCE: 28

```
Met Thr Thr Gly Glu Ala Ser Leu Met Lys Asn Gly Pro Ala Ser Arg
1               5                   10                  15

Ala Arg Arg Glu Glu Arg Ala Asp Gly Pro Ala Thr Glu Leu Ala Ile
            20                  25                  30

Gly Thr Ala Asn Pro Ser Asn Val Phe Asp Gln Glu Thr Tyr Pro Asp
        35                  40                  45

Phe Tyr Phe Asp Val Thr Asn Asn Thr Asp Lys Pro Glu Leu Lys Ala
    50                  55                  60

Lys Phe Gln Arg Met Cys Asn Ser Leu Glu Ser Lys Lys Val His Val
65                  70                  75                  80

Leu His Gly Gly Asp Val Glu Gly Gln Pro Ser Met Val Phe Ile Gly
                85                  90                  95

Arg Ile Leu Leu Asp Val Arg Gln Gly Arg Arg Ser Arg Ala Ser Ala
            100                 105                 110

Lys Leu Ala Lys Glu Ala Ser Leu Lys Ala Leu Arg Glu Trp Gly Gln
            115                 120                 125

Pro Asn Ser Lys Ile Thr His Leu Val Phe Cys Thr Thr Ala Pro Val
    130                 135                 140

Thr Leu Pro Gly Val Asp Ala Ala Leu Ile Gln Ser Leu Gly Leu Asn
145                 150                 155                 160

Pro Ser Val Lys Arg Val Leu Leu Tyr Met Gln Gly Cys Phe Ala Gly
                165                 170                 175

Gly Thr Val Leu Arg His Ala Lys Asp Leu Ala Glu Asn Asn Arg Gly
            180                 185                 190

Ala Arg Val Leu Val Val Cys Ser Glu Thr Thr Ala Val Thr Phe Arg
            195                 200                 205

Gly Pro His Glu Asn His Leu Asp Asn Leu Val Gly Gln Ala Leu Phe
        210                 215                 220

Ala Asp Gly Ala Ser Ala Leu Ile Val Gly Ser Asp Pro Ile Ser Asp
225                 230                 235                 240

Leu Glu Lys Pro Trp Phe Glu Ile Arg Trp Ala Gly Ser Tyr Leu Ile
                245                 250                 255

Pro Glu Ser Gly Gln Ala Ile Ala Gly Gln Leu Lys Glu Val Gly Leu
            260                 265                 270

Glu Phe His Leu Thr Arg Asp Val Ser Gly Leu Val Ser Lys Asn Ile
            275                 280                 285

Val Thr Ile Leu Asn Glu Ala Phe Glu Gly Thr Gly Ile Thr Asp Trp
290                 295                 300

Asn Asp Ile Phe Ile Ile Pro His Pro Gly Gly Pro Ala Ile Leu Asp
305                 310                 315                 320

Val Ile Gln Asp Arg Leu Lys Leu Gln Pro Glu Lys Leu Gln Ala Ser
                325                 330                 335

Arg His Val Leu Ala Glu Phe Gly Asn Met Ser Ser Ala Thr Val His
            340                 345                 350

Phe Ser Leu Asp Gln Met Arg Ser Ser Val Glu Lys Gly Cys Ser
            355                 360                 365

Thr Thr Gly Glu Gly Tyr Glu Leu Gly Ile Leu Leu Gly Leu Gly Pro
    370                 375                 380

Gly Met Thr Val Glu Ser Ile Leu Leu Lys Ser Val Pro Thr Trp Thr
385                 390                 395                 400

Val Ala Ser
```

<210> SEQ ID NO 29
<211> LENGTH: 1179
<212> TYPE: DNA
<213> ORGANISM: Vitis vinifera

<400> SEQUENCE: 29

```
atggcttcag ttgaggaatt tagaaacgct caacgtgcca agggtccggc cactatccta      60
gccattggca cagctactcc tgaccactgt gtctaccagt ctgattatgc tgattactat     120
ttcagggtca ctaagagcga gcacatgact gagttgaaga agaagttcaa tcgcatatgt     180
gacaaatcaa tgatcaagaa gcgttacatt cacttgaccg aagaaatgct tgaggagcac     240
ccaaacattg gtgcttatat ggctccatct cttaacatac gccaagagat tatcactgct     300
gaggtaccta gacttggtag ggatgcagca ttgaaggctc ttaaagagtg gggccaacca     360
aagtccaaga tcacccatct tgtatttttgt acaacctccg gtgtagaaat gcccggtgcg     420
gattacaaac tcgctaatct cttaggtctt gaaacatcgg ttagaagggt gatgttgtac     480
catcaagggt gctatgcagg tggaactgtc cttcgaactg ctaaggatct tgcagaaaat     540
aatgcaggag cacgagttct tgtggtgtgc tctgagatca ctgttgttac attccgtggc     600
ccttccgaag atgctttgga ctctttagtt ggccaagccc ttttggtga tgggtcttca     660
gctgtgattg ttggatcaga tccagatgtc tcgattgaac gaccactctt ccaacttgtt     720
tcagcagccc aaacatttat tcctaattca gcaggagcca ttgccggaaa cttacgtgag     780
gtggggctca cctttcattt gtggcccaat gtgcctactt tgatttctga aacatagag     840
aaatgcttga cccaggcttt tgacccactt ggtattagcg attggaactc gttatttttgg     900
attgctcacc aggtggccc tgcaattctc gatgcagttg aagcaaaact caatttagag     960
aaaaagaaac tcgaagcaac taggcatgtg ttaagtgagt acggtaacat gtcaagtgca    1020
tgtgtgttgt ttattctgga tgagatgaga aagaaatcct tgaaggggga aaaggctacc    1080
acaggtgaag gattggattg gggagtatta tttggttttg gccgggcttt gaccatcgaa    1140
actgttgtgc tgcatagcgt tcctacagtt acaaattaa                           1179
```

<210> SEQ ID NO 30
<211> LENGTH: 392
<212> TYPE: PRT
<213> ORGANISM: Vitis vinifera

<400> SEQUENCE: 30

```
Met Ala Ser Val Glu Glu Phe Arg Asn Ala Gln Arg Ala Lys Gly Pro
  1               5                  10                  15

Ala Thr Ile Leu Ala Ile Gly Thr Ala Thr Pro Asp His Cys Val Tyr
             20                  25                  30

Gln Ser Asp Tyr Ala Asp Tyr Tyr Phe Arg Val Thr Lys Ser Glu His
         35                  40                  45

Met Thr Glu Leu Lys Lys Lys Phe Asn Arg Ile Cys Asp Lys Ser Met
     50                  55                  60

Ile Lys Lys Arg Tyr Ile His Leu Thr Glu Glu Met Leu Glu Glu His
 65                  70                  75                  80

Pro Asn Ile Gly Ala Tyr Met Ala Pro Ser Leu Asn Ile Arg Gln Glu
                 85                  90                  95

Ile Ile Thr Ala Glu Val Pro Arg Leu Gly Arg Asp Ala Ala Leu Lys
            100                 105                 110
```

```
Ala Leu Lys Glu Trp Gly Gln Pro Lys Ser Lys Ile Thr His Leu Val
        115                 120                 125
Phe Cys Thr Thr Ser Gly Val Glu Met Pro Gly Ala Asp Tyr Lys Leu
        130                 135                 140
Ala Asn Leu Leu Gly Leu Glu Thr Ser Val Arg Arg Val Met Leu Tyr
145                 150                 155                 160
His Gln Gly Cys Tyr Ala Gly Gly Thr Val Leu Arg Thr Ala Lys Asp
                165                 170                 175
Leu Ala Glu Asn Asn Ala Gly Ala Arg Val Leu Val Val Cys Ser Glu
            180                 185                 190
Ile Thr Val Val Thr Phe Arg Gly Pro Ser Glu Asp Ala Leu Asp Ser
        195                 200                 205
Leu Val Gly Gln Ala Leu Phe Gly Asp Gly Ser Ser Ala Val Ile Val
    210                 215                 220
Gly Ser Asp Pro Asp Val Ser Ile Glu Arg Pro Leu Phe Gln Leu Val
225                 230                 235                 240
Ser Ala Ala Gln Thr Phe Ile Pro Asn Ser Ala Gly Ala Ile Ala Gly
                245                 250                 255
Asn Leu Arg Glu Val Gly Leu Thr Phe His Leu Trp Pro Asn Val Pro
            260                 265                 270
Thr Leu Ile Ser Glu Asn Ile Glu Lys Cys Leu Thr Gln Ala Phe Asp
        275                 280                 285
Pro Leu Gly Ile Ser Asp Trp Asn Ser Leu Phe Trp Ile Ala His Pro
    290                 295                 300
Gly Gly Pro Ala Ile Leu Asp Ala Val Glu Ala Lys Leu Asn Leu Glu
305                 310                 315                 320
Lys Lys Lys Leu Glu Ala Thr Arg His Val Leu Ser Glu Tyr Gly Asn
                325                 330                 335
Met Ser Ser Ala Cys Val Leu Phe Ile Leu Asp Glu Met Arg Lys Lys
            340                 345                 350
Ser Leu Lys Gly Glu Lys Ala Thr Thr Gly Glu Gly Leu Asp Trp Gly
        355                 360                 365
Val Leu Phe Gly Phe Gly Pro Gly Leu Thr Ile Glu Thr Val Val Leu
    370                 375                 380
His Ser Val Pro Thr Val Thr Asn
385                 390

<210> SEQ ID NO 31
<211> LENGTH: 1767
<212> TYPE: DNA
<213> ORGANISM: Pseudomonas putida

<400> SEQUENCE: 31
atgcaacctg tcgagccact ggcgccgctg ccggcgcgcc tgctcgagcg cctggtgcat      60
tgggcccagg tgcgcccgga caccactttc atcgcggcac gccaggcaga cggtgcctgg     120
cgttcgatca gctacgtgca gatgctcgcc gatgtgcgca ccatcgccgc caacttgcta     180
ggactgggcc tcagtgccga gcgccgctg gcgctgcttt ccggcaacga catcgaacac     240
ctgcaaatcg ccctcggcgc catgtatgcc ggtattgcct attgcccggt gtcgccggcc     300
tacgcgctgt gtcgcaagac cttcgccaag ttgcgccatg tctgcgaggt gctcacccc      360
ggagtggtct tcgtcagcga cagccagccg ttccagcgcg ccttcgaggc ggtgctggac     420
gattcggtcg gcgtgatcag cgtcgtggc caggtcgcag gtcgccccca tataagcttc     480
gacagcctgt gcaaccgggt gacctggcg gcggccgatg cggctttcgc cgccaccggg     540
```

-continued

```
ccggacacca tcgccaaatt cctcttcacc tcgggctcga ccaagctgcc caaggcggtg    600
atcaccaccc agcgcatgct gtgcgccaat cagcagatgc ttctgcagac ttttccgacg    660
ttcgccgagg agccgccggt gctggtggac tggctgccgt ggaaccacac gttcggcggt    720
agccacaacc tcggcatcgt gctttacaac gggggcagtt tctacctgga cgccggcaag    780
ccgaccccgc aaggcttcgc cgagaccttg cgcaatctgc gcgagatttc ccccacggcc    840
tacctcaccg tacccaaggg ctgggaggaa ctggtcaagg cactggagca ggaccccgcg    900
ctacgcgagg tgttctttgc ccgcatcaag ctgttcttct tgccgccgc aggcctgtcg     960
caaagcgtct gggaccggct ggaccgcatt gccgagcaac actgtggcga acgcatccgc   1020
atgatggccg gccttggcat gaccgaagcc tcgccatcgt gcaccttcac caccgggcct   1080
tgtcgatgg ccggctatgt cgggctgccg gcacctggct gcgaagtgaa gctggtgccg    1140
gtgggcgaca gctcgaggc gcgcttccgt ggcccgcata tcatgccggg ctactggcgc    1200
tcgccgcagc agaccgccga gcgttcgac gaggagggct tctactgttc gggcgacgcg    1260
ttgaagctgg ccgatgccag gcagcccgag cttggcctga tgttcgatgg ccgtatcgct   1320
gaggacttca aactttcgtc cggggtattc gtcagtgtcg ggccgctgcg caaccgcgca   1380
gtgctggagg gctcgcctta cgtacaggac atcgtggtca ccgcgccgga ccgtgaatgc   1440
ctgggcctgc tggtgttccc cgcgtctgcc gagtgtcggc cctggccgg gctggcagag   1500
gatgccagcg atgcgcgggt gctggccaac gacaccgtgc gcagttggtt cgctgactgg   1560
ctggagcgct tgaaccgcga tgcccaaggc aacgccagcc gtatcgaatg gctgtcgctg   1620
ctggccgagc cgccgtcgat cgacgccggt gaaatcaccg acaagggctc gatcaatcag   1680
cgcgccgtgc tgcagcggcg cgccgctcag gtcgaggcgc tgtaccgtgg cgaagacccc   1740
gacgcattgc acgccaaggt gcggcct                                      1767
```

<210> SEQ ID NO 32
<211> LENGTH: 589
<212> TYPE: PRT
<213> ORGANISM: Pseudomonas putida

<400> SEQUENCE: 32

```
Met Gln Pro Val Glu Pro Leu Ala Pro Leu Ala Arg Leu Leu Glu
 1               5                  10                  15

Arg Leu Val His Trp Ala Gln Val Arg Pro Asp Thr Thr Phe Ile Ala
                20                  25                  30

Ala Arg Gln Ala Asp Gly Ala Trp Arg Ser Ile Ser Tyr Val Gln Met
            35                  40                  45

Leu Ala Asp Val Arg Thr Ile Ala Ala Asn Leu Gly Leu Gly Leu
        50                  55                  60

Ser Ala Glu Arg Pro Leu Ala Leu Leu Ser Gly Asn Asp Ile Glu His
65                  70                  75                  80

Leu Gln Ile Ala Leu Gly Ala Met Tyr Ala Gly Ile Ala Tyr Cys Pro
                85                  90                  95

Val Ser Pro Ala Tyr Ala Leu Leu Ser Gln Asp Phe Ala Lys Leu Arg
            100                 105                 110

His Val Cys Glu Val Leu Thr Pro Gly Val Val Phe Val Ser Asp Ser
        115                 120                 125

Gln Pro Phe Gln Arg Ala Phe Glu Ala Val Leu Asp Asp Ser Val Gly
    130                 135                 140
```

-continued

```
Val Ile Ser Val Arg Gly Gln Val Ala Gly Arg Pro His Ile Ser Phe
145                 150                 155                 160

Asp Ser Leu Leu Gln Pro Gly Asp Leu Ala Ala Asp Ala Ala Phe
            165                 170                 175

Ala Ala Thr Gly Pro Asp Thr Ile Ala Lys Phe Leu Phe Thr Ser Gly
            180                 185                 190

Ser Thr Lys Leu Pro Lys Ala Val Ile Thr Thr Gln Arg Met Leu Cys
            195                 200                 205

Ala Asn Gln Gln Met Leu Leu Gln Thr Phe Pro Thr Phe Ala Glu Glu
            210                 215                 220

Pro Pro Val Leu Val Asp Trp Leu Pro Trp Asn His Thr Phe Gly Gly
225                 230                 235                 240

Ser His Asn Leu Gly Ile Val Leu Tyr Asn Gly Gly Ser Phe Tyr Leu
            245                 250                 255

Asp Ala Gly Lys Pro Thr Pro Gln Gly Phe Ala Glu Thr Leu Arg Asn
            260                 265                 270

Leu Arg Glu Ile Ser Pro Thr Ala Tyr Leu Thr Val Pro Lys Gly Trp
            275                 280                 285

Glu Glu Leu Val Lys Ala Leu Glu Gln Asp Pro Ala Leu Arg Glu Val
            290                 295                 300

Phe Phe Ala Arg Ile Lys Leu Phe Phe Phe Ala Ala Gly Leu Ser
305                 310                 315                 320

Gln Ser Val Trp Asp Arg Leu Asp Arg Ile Ala Glu Gln His Cys Gly
                325                 330                 335

Glu Arg Ile Arg Met Met Ala Gly Leu Gly Met Thr Glu Ala Ser Pro
                340                 345                 350

Ser Cys Thr Phe Thr Thr Gly Pro Leu Ser Met Ala Gly Tyr Val Gly
            355                 360                 365

Leu Pro Ala Pro Gly Cys Glu Val Lys Leu Val Pro Val Gly Asp Lys
370                 375                 380

Leu Glu Ala Arg Phe Arg Gly Pro His Ile Met Pro Gly Tyr Trp Arg
385                 390                 395                 400

Ser Pro Gln Gln Thr Ala Glu Ala Phe Asp Glu Glu Gly Phe Tyr Cys
                405                 410                 415

Ser Gly Asp Ala Leu Lys Leu Ala Asp Ala Arg Gln Pro Glu Leu Gly
            420                 425                 430

Leu Met Phe Asp Gly Arg Ile Ala Glu Asp Phe Lys Leu Ser Ser Gly
            435                 440                 445

Val Phe Val Ser Val Gly Pro Leu Arg Asn Arg Ala Val Leu Glu Gly
            450                 455                 460

Ser Pro Tyr Val Gln Asp Ile Val Thr Ala Pro Arg Glu Cys
465                 470                 475                 480

Leu Gly Leu Leu Val Phe Pro Arg Leu Pro Glu Cys Arg Arg Leu Ala
                485                 490                 495

Gly Leu Ala Glu Asp Ala Ser Asp Ala Arg Val Leu Ala Asn Asp Thr
            500                 505                 510

Val Arg Ser Trp Phe Ala Asp Trp Leu Glu Arg Leu Asn Arg Asp Ala
            515                 520                 525

Gln Gly Asn Ala Ser Arg Ile Glu Trp Leu Ser Leu Leu Ala Glu Pro
            530                 535                 540

Pro Ser Ile Asp Ala Gly Glu Ile Thr Asp Lys Gly Ser Ile Asn Gln
545                 550                 555                 560
```

Arg Ala Val Leu Gln Arg Arg Ala Ala Gln Val Glu Ala Leu Tyr Arg
            565                 570                 575

Gly Glu Asp Pro Asp Ala Leu His Ala Lys Val Arg Pro
            580                 585

<210> SEQ ID NO 33
<211> LENGTH: 1236
<212> TYPE: DNA
<213> ORGANISM: Rhodobacter sphaeroides

<400> SEQUENCE: 33

| | | | | | |
|---|---|---|---|---|---|
| atgacagccg | aggggcctct | ggcaccggaa | gatcgggtgc | tcgaccggga | ggcgatcggg | 60 |
| cgcctctgcg | tctccctgat | cgcggccgag | cagcaggacc | tgctgcggga | agggcgcgtc | 120 |
| ggtcatcatc | agatgatcgg | cgcgcgcctc | ctgacggcag | gcatccgtc | gcccgacgac | 180 |
| ctgctgatcg | acgaagacac | gctggggctc | gacagtctgc | tcatgctctc | gctcgtcacc | 240 |
| cgcgtggcgg | gcttcttcca | tctgtcggat | tcgaacaccg | aggattatct | tctcgtgcga | 300 |
| cgccgtctgg | agagtgggt | ggatctgatc | gatcatcacc | acaccctgat | ggggccgaag | 360 |
| gcgcgcttca | ccttcgcgac | ctcgggaagc | accgcaggac | cgaagcccgt | gacccacagc | 420 |
| gccgcggcac | tgctctcgga | agggcaggcc | atcgcgaaga | tcctcacgga | gcggcctccc | 480 |
| gaggtgcgcc | gcgtcctctc | ctgcgttccg | gcccaccaca | tctacggctt | cctctggtcc | 540 |
| tgcctgtttc | cctcccgccg | cggtctcgag | gcgaagcaac | tggcgaacct | gtccgcttcc | 600 |
| ggcatcatgc | ggcacgcgcg | ctccggcgat | ctggtggtgg | gcacgccctt | catctgggag | 660 |
| cagttcgcgg | atctcgacta | ccggctgccc | ggcgacgtgg | tcggggtgac | gtccggcgca | 720 |
| ccctcgacgg | ccgagacatg | gcgctgcgcc | tctgcgctcg | gcccggcacg | gatgctggac | 780 |
| atctatggct | cgaccgaaac | cggggggcatc | ggctggcgcg | agcgccggga | cgacccttc | 840 |
| cgaaccctgc | ccgatctcgc | ctgctttcat | gacacgttga | gcaggctggg | ccggcggctg | 900 |
| gacctgcagg | acgagatcgc | ctgggacaag | gacggcggct | tcacgattct | cggccgcaag | 960 |
| gacgagatcc | tgcaggtcgc | gggatcgaac | gtctctcctg | ccgcggtccg | agatatcctg | 1020 |
| ctccggaacc | cgcgtgtccg | ggatgcggcg | gtgcggctcg | acggacgcag | gctgaaggcc | 1080 |
| gtgatctctg | tggcggaggg | cgctgacgag | gcagagatcg | agatcgaact | gcgcgcgact | 1140 |
| gcggcgcggc | atcttccggc | acctgccagg | ccggaccggt | tccttttcgc | gacggaactc | 1200 |
| ccgcgcacgg | gtgcagggaa | attggcggac | tggtag | | | 1236 |

<210> SEQ ID NO 34
<211> LENGTH: 411
<212> TYPE: PRT
<213> ORGANISM: Rhodobacter sphaeroides

<400> SEQUENCE: 34

Met Thr Ala Glu Gly Pro Leu Ala Pro Glu Asp Arg Val Leu Asp Arg
 1               5                  10                  15

Glu Ala Ile Gly Arg Leu Cys Val Ser Leu Ile Ala Ala Glu Gln Gln
            20                  25                  30

Asp Leu Leu Arg Glu Gly Arg Val Gly His His Gln Met Ile Gly Ala
        35                  40                  45

Arg Leu Leu Thr Ala Gly His Pro Ser Pro Asp Asp Leu Leu Ile Asp
    50                  55                  60

Glu Asp Thr Leu Gly Leu Asp Ser Leu Leu Met Leu Ser Leu Val Thr
65                  70                  75                  80

```
Arg Val Ala Gly Phe Phe His Leu Ser Asp Ser Asn Thr Glu Asp Tyr
                85                  90                  95

Leu Leu Val Arg Arg Leu Gly Glu Trp Val Asp Leu Ile Asp His
            100                 105                 110

His His Thr Leu Met Gly Pro Lys Ala Arg Phe Thr Phe Ala Thr Ser
        115                 120                 125

Gly Ser Thr Ala Gly Pro Lys Pro Val Thr His Ser Ala Ala Ala Leu
    130                 135                 140

Leu Ser Glu Gly Gln Ala Ile Ala Lys Ile Leu Thr Glu Arg Pro Pro
145                 150                 155                 160

Glu Val Arg Arg Val Leu Ser Cys Val Pro Ala His His Ile Tyr Gly
                165                 170                 175

Phe Leu Trp Ser Cys Leu Phe Pro Ser Arg Arg Gly Leu Glu Ala Lys
            180                 185                 190

Gln Leu Ala Asn Leu Ser Ala Ser Gly Ile Met Arg His Ala Arg Ser
        195                 200                 205

Gly Asp Leu Val Val Gly Thr Pro Phe Ile Trp Glu Gln Phe Ala Asp
    210                 215                 220

Leu Asp Tyr Arg Leu Pro Gly Asp Val Val Gly Val Thr Ser Gly Ala
225                 230                 235                 240

Pro Ser Thr Ala Glu Thr Trp Arg Cys Ala Ser Ala Leu Gly Pro Ala
                245                 250                 255

Arg Met Leu Asp Ile Tyr Gly Ser Thr Glu Thr Gly Gly Ile Gly Trp
            260                 265                 270

Arg Glu Arg Arg Asp Asp Pro Phe Arg Thr Leu Pro Asp Leu Ala Cys
        275                 280                 285

Phe His Asp Thr Leu Ser Arg Leu Gly Arg Arg Leu Asp Leu Gln Asp
    290                 295                 300

Glu Ile Ala Trp Asp Lys Asp Gly Gly Phe Thr Ile Leu Gly Arg Lys
305                 310                 315                 320

Asp Glu Ile Leu Gln Val Ala Gly Ser Asn Val Ser Pro Ala Ala Val
                325                 330                 335

Arg Asp Ile Leu Arg Asn Pro Arg Val Arg Asp Ala Ala Val Arg
            340                 345                 350

Leu Asp Gly Arg Arg Leu Lys Ala Val Ile Ser Val Ala Glu Gly Ala
        355                 360                 365

Asp Glu Ala Glu Ile Glu Ile Glu Leu Arg Ala Thr Ala Ala Arg His
    370                 375                 380

Leu Pro Ala Pro Ala Arg Pro Asp Arg Phe Leu Phe Ala Thr Glu Leu
385                 390                 395                 400

Pro Arg Thr Gly Ala Gly Lys Leu Ala Asp Trp
                405                 410
```

<210> SEQ ID NO 35
<211> LENGTH: 1569
<212> TYPE: DNA
<213> ORGANISM: Streptomyces coelicolor

<400> SEQUENCE: 35

| | | | | | |
|---|---|---|---|---|---|
| gtgttccgca | gcgagtacgc | agacgtcccg | cccgtcgacc | tgcccatcca | cgacgccgtg | 60 |
| ctcggcgggg | ccgccgcctt | cgggagcacc | cggcgctga | tcgacggcac | cgacggcacc | 120 |
| accctcacct | acgagcaggt | ggaccggttc | caccggcgcg | tcgccgccgc | cctcgccgag | 180 |
| accggcgtgc | gcaagggcga | cgtcctcgcc | ctgcacagcc | ccaacaccgt | cgccttcccc | 240 |

```
ctggccttct acgccgccac ccgcgcgggc gcctccgtca ccacggtgca tccgctcgcg      300
acggcggagg agttcgccaa gcagctgaag gacagcgcgg cccgctggat cgtcaccgtc      360
tcaccgctcc tgtccaccgc ccgccgggcc gccgaactcg cgggcggcgt ccaggagatc      420
ctggtctgcg acagcgcgcc cggtcaccgc tccctcgtcg acatgctggc ctcgaccgcg      480
cccgaaccgt ccgtcgccat cgacccggcc gaggacgtcg ccgccctgcc gtactcctcg      540
ggcaccaccg gcacccccaa gggcgtcatg ctcacacacc ggcagatcgc caccaacctc      600
gcccagctcg aaccgtcgat gccgtccgcg cccggcgacc gcgtcctcgc cgtgctgccg      660
ttcttccaca tctacggcct gaccgccctg atgaacgccc cgctccggct cggcgccacc      720
gtcgtggtcc tgccccgctt cgacctggag cagttcctcg ccgccatcca gaaccaccgc      780
atcaccagcc tgtacgtcgc cccgccgatc gtcctggccc tcgccaaaca cccccggtc      840
gccgactacg acctctcctc gctgaggtac atcgtcagcg ccgccgcccc gctcgacgcg      900
cgtctcgccg ccgcctgctc gcagcggctc ggcctgccgc ccgtcggcca ggcctacggc      960
atgaccgaac tgtccccggg cacccacgtc gtcccccTGg acgcgatggc cgacgcgccg    1020
cccggcaccg tcggcaggct catcgcgggc accgagatgc gcatcgtctc cctcaccgac    1080
ccgggcacgg acctccccgc cggagagtcc ggggagatcc tcatccgcgg cccccagatc    1140
atgaagggct acctgggccg ccccgacgcc ccgccgccca tgatcgacga ggagggctgg    1200
ctgcacaccg gggacgtcgg acacgtcgac gccgacggct ggctgttcgt cgtcgaccgc    1260
gtcaaggaac tgatcaagta caagggcttc caggtggccc ccgccgaact ggaggcccac    1320
ctgctcaccc accccggcgt cgccgacgcg gccgtcgtcg gcgcctacga cgacgacggc    1380
aacgaggtac cgcacgcctt cgtcgtccgc cagccggccg cacccggcct cgcggagagc    1440
gagatcatga tgtacgtcgc cgaacgcgtc gccccctaca aacgcgtccg ccgggtcacc    1500
ttcgtcgacg ccgtcccccg cgccgcctcc ggcaagatcc tccgccgaca gctcagggag    1560
ccgcgatga                                                             1569
```

<210> SEQ ID NO 36
<211> LENGTH: 522
<212> TYPE: PRT
<213> ORGANISM: Streptomyces coelicolor

<400> SEQUENCE: 36

```
Met Phe Arg Ser Glu Tyr Ala Asp Val Pro Pro Val Asp Leu Pro Ile
 1               5                  10                  15

His Asp Ala Val Leu Gly Gly Ala Ala Ala Phe Gly Ser Thr Pro Ala
                20                  25                  30

Leu Ile Asp Gly Thr Asp Gly Thr Thr Leu Thr Tyr Glu Gln Val Asp
            35                  40                  45

Arg Phe His Arg Arg Val Ala Ala Ala Leu Ala Glu Thr Gly Val Arg
        50                  55                  60

Lys Gly Asp Val Leu Ala Leu His Ser Pro Asn Thr Val Ala Phe Pro
 65                  70                  75                  80

Leu Ala Phe Tyr Ala Ala Thr Arg Ala Gly Ala Ser Val Thr Thr Val
                85                  90                  95

His Pro Leu Ala Thr Ala Glu Glu Phe Ala Lys Gln Leu Lys Asp Ser
               100                 105                 110

Ala Ala Arg Trp Ile Val Thr Val Ser Pro Leu Leu Ser Thr Ala Arg
           115                 120                 125
```

```
Arg Ala Ala Glu Leu Ala Gly Gly Val Gln Glu Ile Leu Val Cys Asp
    130                 135                 140

Ser Ala Pro Gly His Arg Ser Leu Val Asp Met Leu Ala Ser Thr Ala
145                 150                 155                 160

Pro Glu Pro Ser Val Ala Ile Asp Pro Ala Glu Asp Val Ala Ala Leu
                165                 170                 175

Pro Tyr Ser Ser Gly Thr Thr Gly Thr Pro Lys Gly Val Met Leu Thr
                180                 185                 190

His Arg Gln Ile Ala Thr Asn Leu Ala Gln Leu Glu Pro Ser Met Pro
            195                 200                 205

Ser Ala Pro Gly Asp Arg Val Leu Ala Val Leu Pro Phe Phe His Ile
    210                 215                 220

Tyr Gly Leu Thr Ala Leu Met Asn Ala Pro Leu Arg Leu Gly Ala Thr
225                 230                 235                 240

Val Val Val Leu Pro Arg Phe Asp Leu Glu Gln Phe Leu Ala Ala Ile
                245                 250                 255

Gln Asn His Arg Ile Thr Ser Leu Tyr Val Ala Pro Pro Ile Val Leu
                260                 265                 270

Ala Leu Ala Lys His Pro Leu Val Ala Asp Tyr Asp Leu Ser Ser Leu
            275                 280                 285

Arg Tyr Ile Val Ser Ala Ala Pro Leu Asp Ala Arg Leu Ala Ala
    290                 295                 300

Ala Cys Ser Gln Arg Leu Gly Leu Pro Pro Val Gly Gln Ala Tyr Gly
305                 310                 315                 320

Met Thr Glu Leu Ser Pro Gly Thr His Val Val Pro Leu Asp Ala Met
                325                 330                 335

Ala Asp Ala Pro Pro Gly Thr Val Gly Arg Leu Ile Ala Gly Thr Glu
                340                 345                 350

Met Arg Ile Val Ser Leu Thr Asp Pro Gly Thr Asp Leu Pro Ala Gly
            355                 360                 365

Glu Ser Gly Glu Ile Leu Ile Arg Gly Pro Gln Ile Met Lys Gly Tyr
    370                 375                 380

Leu Gly Arg Pro Asp Ala Thr Ala Ala Met Ile Asp Glu Glu Gly Trp
385                 390                 395                 400

Leu His Thr Gly Asp Val Gly His Val Asp Ala Asp Gly Trp Leu Phe
                405                 410                 415

Val Val Asp Arg Val Lys Glu Leu Ile Lys Tyr Lys Gly Phe Gln Val
                420                 425                 430

Ala Pro Ala Glu Leu Glu Ala His Leu Leu Thr His Pro Gly Val Ala
            435                 440                 445

Asp Ala Ala Val Val Gly Ala Tyr Asp Asp Gly Asn Glu Val Pro
    450                 455                 460

His Ala Phe Val Val Arg Gln Pro Ala Ala Pro Gly Leu Ala Glu Ser
465                 470                 475                 480

Glu Ile Met Met Tyr Val Ala Glu Arg Val Ala Pro Tyr Lys Arg Val
                485                 490                 495

Arg Arg Val Thr Phe Val Asp Ala Val Pro Arg Ala Ala Ser Gly Lys
                500                 505                 510

Ile Leu Arg Arg Gln Leu Arg Glu Pro Arg
            515                 520

<210> SEQ ID NO 37
<211> LENGTH: 28
<212> TYPE: DNA
```

```
<213> ORGANISM: Artificial Sequence
<220> FEATURE:
<223> OTHER INFORMATION: oligonucleotide

<400> SEQUENCE: 37
ggcgcgcctt aaacaaaatt atttctag                                          28

<210> SEQ ID NO 38
<211> LENGTH: 24
<212> TYPE: DNA
<213> ORGANISM: Artificial Sequence
<220> FEATURE:
<223> OTHER INFORMATION: oligonucleotide

<400> SEQUENCE: 38
taattaaggt ctccagcttg gctg                                              24

<210> SEQ ID NO 39
<211> LENGTH: 44
<212> TYPE: DNA
<213> ORGANISM: Artificial Sequence
<220> FEATURE:
<223> OTHER INFORMATION: oligonucleotide

<400> SEQUENCE: 39
ggtaccctcg aggtttaaac aagcttcgct tctctgagta ggac                        44

<210> SEQ ID NO 40
<211> LENGTH: 42
<212> TYPE: DNA
<213> ORGANISM: Artificial Sequence
<220> FEATURE:
<223> OTHER INFORMATION: oligonucleotide

<400> SEQUENCE: 40
ccatgggcgg ccgcgaattc gtcgacctct gaatggcggg ag                          42

<210> SEQ ID NO 41
<211> LENGTH: 17
<212> TYPE: DNA
<213> ORGANISM: Artificial Sequence
<220> FEATURE:
<223> OTHER INFORMATION: oligonucleotide

<400> SEQUENCE: 41
aggaggatta caaaatg                                                      17

<210> SEQ ID NO 42
<211> LENGTH: 1170
<212> TYPE: DNA
<213> ORGANISM: Arachis hypogaea

<400> SEQUENCE: 42
atggtgtctg tgagtgagat ccgcaaagtt caaagggcag aaggccctgc aactgtattg       60
gcgataggca cagcaaatcc accaaattgt attgatcaga gcacatatgc tgattattat      120
tttagagtaa ctaacagtga acacatgact gatctcaaga agaagtttca gcgcatttgt      180
gagagaacac aaatcaagaa cagacatatg tacttaacag aagagatact gaaagagaat      240
cctaacatgt gcgcatacaa agcaccgtcg ttggatgcaa gggaagacat gatgatcagg      300
gaggtaccaa gggttggaaa agaggctgca accaaggcca tcaaggaatg ggtcagcca       360 atgtctaaga tcacacattt gatcttctgc accaccagcg tgttgcatt gcctggcgtt       420 gattacgaac tcatcgtact cttaggactc gacccatccg tcaagaggta catgatgtac      480
```

```
caccaaggct gcttcgccgg tggcactgtc cttcgtttgg ctaaggactt ggctgaaaac    540
aacaaggatg ctcgtgtgct tatcgtttgt tctgagaata ccgcagtcac tttccgtggt    600
cctagtgaga cagacatgga tagtcttgta gggcaagcct tgtttgctga tggagctgct    660
gcgattatca ttggttctga tcctgtgcca gaggttgaaa agcctatctt tgaaattgtt    720
tcgactgatc aaaaacttgt ccctaacagc catggagcca tcgtggtct ccttcgtgaa     780 gttgggctta cattctatct aataagagt gttcctgata ttatttcaca aaacatcaat     840
gatgcgctca gtaaagcttt tgatccattg ggtatatctg attataactc aatattttgg   900
attgcacacc ctggtggacg tgcaattttg gatcaggttg aacagaaagt gaacttgaaa    960
ccagagaaga tgaatgccac tagagacgtg cttagcaatt acggtaacat gtcaagtgcg   1020
tgtgtgttct tcatcatgga tttaatgagg aagaagtccc ttgaagaagg acttaaaact   1080
accggtgaag gacttgattg gggcgtactt tttggctttg gtcctggtct cactattgaa   1140
actgttgttc tccgcagcat ggccatataa                                    1170
```

<210> SEQ ID NO 43
<211> LENGTH: 389
<212> TYPE: PRT
<213> ORGANISM: Arachis hypogaea

<400> SEQUENCE: 43

```
Met Val Ser Val Ser Glu Ile Arg Lys Val Gln Arg Ala Glu Gly Pro
 1               5                  10                  15

Ala Thr Val Leu Ala Ile Gly Thr Ala Asn Pro Pro Asn Cys Ile Asp
                20                  25                  30

Gln Ser Thr Tyr Ala Asp Tyr Tyr Phe Arg Val Thr Asn Ser Glu His
        35                  40                  45

Met Thr Asp Leu Lys Lys Lys Phe Gln Arg Ile Cys Glu Arg Thr Gln
    50                  55                  60

Ile Lys Asn Arg His Met Tyr Leu Thr Glu Glu Ile Leu Lys Glu Asn
65                  70                  75                  80

Pro Asn Met Cys Ala Tyr Lys Ala Pro Ser Leu Asp Ala Arg Glu Asp
                85                  90                  95

Met Met Ile Arg Glu Val Pro Arg Val Gly Lys Glu Ala Ala Thr Lys
            100                 105                 110

Ala Ile Lys Glu Trp Gly Gln Pro Met Ser Lys Ile Thr His Leu Ile
        115                 120                 125

Phe Cys Thr Thr Ser Gly Val Ala Leu Pro Gly Val Asp Tyr Glu Leu
    130                 135                 140

Ile Val Leu Leu Gly Leu Asp Pro Ser Val Lys Arg Tyr Met Met Tyr
145                 150                 155                 160

His Gln Gly Cys Phe Ala Gly Gly Thr Val Leu Arg Leu Ala Lys Asp
                165                 170                 175

Leu Ala Glu Asn Asn Lys Asp Ala Arg Val Leu Ile Val Cys Ser Glu
            180                 185                 190

Asn Thr Ala Val Thr Phe Arg Gly Pro Ser Glu Thr Asp Met Asp Ser
        195                 200                 205

Leu Val Gly Gln Ala Leu Phe Ala Asp Gly Ala Ala Ile Ile Ile
    210                 215                 220

Gly Ser Asp Pro Val Pro Glu Val Glu Lys Pro Ile Phe Glu Ile Val
225                 230                 235                 240
```

```
Ser Thr Asp Gln Lys Leu Val Pro Asn Ser His Gly Ala Ile Gly Gly
                245                 250                 255
Leu Leu Arg Glu Val Gly Leu Thr Phe Tyr Leu Asn Lys Ser Val Pro
            260                 265                 270
Asp Ile Ile Ser Gln Asn Ile Asn Asp Ala Leu Ser Lys Ala Phe Asp
        275                 280                 285
Pro Leu Gly Ile Ser Asp Tyr Asn Ser Ile Phe Trp Ile Ala His Pro
    290                 295                 300
Gly Gly Arg Ala Ile Leu Asp Gln Val Glu Gln Lys Val Asn Leu Lys
305                 310                 315                 320
Pro Glu Lys Met Asn Ala Thr Arg Asp Val Leu Ser Asn Tyr Gly Asn
                325                 330                 335
Met Ser Ser Ala Cys Val Phe Phe Ile Met Asp Leu Met Arg Lys Lys
            340                 345                 350
Ser Leu Glu Glu Gly Leu Lys Thr Thr Gly Glu Gly Leu Asp Trp Gly
        355                 360                 365
Val Leu Phe Gly Phe Gly Pro Gly Leu Thr Ile Glu Thr Val Val Leu
    370                 375                 380
Arg Ser Met Ala Ile
385

<210> SEQ ID NO 44
<211> LENGTH: 1077
<212> TYPE: DNA
<213> ORGANISM: Arabidopsis thaliana

<400> SEQUENCE: 44
atggctccag gaactttgac tgagctagcc ggagagtcta agctcaactc taaattcgtc      60
cgagacgaag acgaacgccc taaagtcgct tacaatgtgt ttagcgacga atcccggtg     120
atctctctcg ccggtatcga tgacgtcgat ggaaaaagag agagatctg ccgtcagatc      180
gtcgaggctt gtgagaattg ggtatcttc caagtggttg atcacggcgt cgatactaac      240
ttggtggcgg atatgactcg cctcgctcgt gacttctttg ctttacctcc ggaagacaag      300
ctccgtttcg acatgtccgg tggtaaaaaa ggtggattca tcgtctctag tcacctccag      360
ggagaggctg tgcaagattg gagagagatt gtaacgtatt tctcgtaccc ggtgagaaac      420
agagactact cacggtggcc aaataagcct gaaggatggg tgaaagtgac ggaggagtat      480
agtgagaggc ttatgagttt ggcttgtaag cttcttgagg ttttgtctga agctatgggt      540
cttgagaaag agtctcttac caatgcatgc gtcgatatgg accaaaagat tgttgttaat      600
tattacccaa aatgccctca gcctgatctc accctcggac tcaagcgtca cactgaccct      660
ggaaccatta ccttgctgct acaagaccaa gtcggtggat acaagccac acgtgacaat      720
ggcaagacct ggattacggt tcagcctgtt gaaggagcgt tgtcgtcaa tctcggcgac      780
cacggtcatt ttttgagcaa tgggaggttc aagaatgctg atcatcaggc cgtggtgaac      840
tctaactcga gcagattatc catagccacg ttccagaacc ccgcgccgga tgccacagtg      900
tatccactga agtaagaga aggagagaag gcaatattgg aggagccaat cacgtttgcc      960
gagatgtata agagaaagat gggaagagat ttggagcttg ctcgcctcaa gaagctggct     1020
aaagaggagc gtgaccacaa agaagttgcc aagcctgtcg accaaatctt cgcttga       1077

<210> SEQ ID NO 45
<211> LENGTH: 358
<212> TYPE: PRT
<213> ORGANISM: Arabidopsis thaliana
```

```
<400> SEQUENCE: 45

Met Ala Pro Gly Thr Leu Thr Glu Leu Ala Gly Glu Ser Lys Leu Asn
1               5                   10                  15

Ser Lys Phe Val Arg Asp Glu Asp Arg Pro Lys Val Ala Tyr Asn
            20                  25                  30

Val Phe Ser Asp Glu Ile Pro Val Ile Ser Leu Ala Gly Ile Asp Asp
        35                  40                  45

Val Asp Gly Lys Arg Gly Glu Ile Cys Arg Gln Ile Val Glu Ala Cys
    50                  55                  60

Glu Asn Trp Gly Ile Phe Gln Val Val Asp His Gly Val Asp Thr Asn
65              70                  75                  80

Leu Val Ala Asp Met Thr Arg Leu Ala Arg Asp Phe Phe Ala Leu Pro
                85                  90                  95

Pro Glu Asp Lys Leu Arg Phe Asp Met Ser Gly Gly Lys Lys Gly Gly
            100                 105                 110

Phe Ile Val Ser Ser His Leu Gln Gly Glu Ala Val Gln Asp Trp Arg
        115                 120                 125

Glu Ile Val Thr Tyr Phe Ser Tyr Pro Val Arg Asn Arg Asp Tyr Ser
    130                 135                 140

Arg Trp Pro Asn Lys Pro Glu Gly Trp Val Lys Val Thr Glu Glu Tyr
145             150                 155                 160

Ser Glu Arg Leu Met Ser Leu Ala Cys Lys Leu Leu Glu Val Leu Ser
                165                 170                 175

Glu Ala Met Gly Leu Glu Lys Glu Ser Leu Thr Asn Ala Cys Val Asp
            180                 185                 190

Met Asp Gln Lys Ile Val Val Asn Tyr Tyr Pro Lys Cys Pro Gln Pro
        195                 200                 205

Asp Leu Thr Leu Gly Leu Lys Arg His Thr Asp Pro Gly Thr Ile Thr
    210                 215                 220

Leu Leu Leu Gln Asp Gln Val Gly Gly Leu Gln Ala Thr Arg Asp Asn
225             230                 235                 240

Gly Lys Thr Trp Ile Thr Val Gln Pro Val Glu Gly Ala Phe Val Val
                245                 250                 255

Asn Leu Gly Asp His Gly His Phe Leu Ser Asn Gly Arg Phe Lys Asn
            260                 265                 270

Ala Asp His Gln Ala Val Val Asn Ser Asn Ser Ser Arg Leu Ser Ile
        275                 280                 285

Ala Thr Phe Gln Asn Pro Ala Pro Asp Ala Thr Val Tyr Pro Leu Lys
    290                 295                 300

Val Arg Glu Gly Glu Lys Ala Ile Leu Glu Glu Pro Ile Thr Phe Ala
305             310                 315                 320

Glu Met Tyr Lys Arg Lys Met Gly Arg Asp Leu Glu Leu Ala Arg Leu
                325                 330                 335

Lys Lys Leu Ala Lys Glu Glu Arg Asp His Lys Glu Val Ala Lys Pro
            340                 345                 350

Val Asp Gln Ile Phe Ala
        355

<210> SEQ ID NO 46
<211> LENGTH: 1011
<212> TYPE: DNA
<213> ORGANISM: Arabidopsis thaliana

<400> SEQUENCE: 46
```

-continued

```
atggaggtcg aaagagtcca agacatttca tcttcttctc tactaacaga agcaatcccg    60
ttggagttca tcagatcaga gaaagaacaa ccagcgatca caacattccg aggtccaacg   120
ccggcgattc ccgtcgtcga tctaagcgat cccgacgaag aaagcgtgag cgtgcggtg    180
gtgaaagcga gtgaagaatg ggggctattc aagtggtta accacgggat tccgacggag    240
ctgatacgac gtttacaaga cgtcggaaga aaattcttcg agcttccttc gtcggagaaa   300
gaatccgtcg ctaaaccgga agattcgaaa gacattgaag gatacggaac aaagcttcag   360
aaagatccag aaggtaaaaa agcttgggtc gatcatctct ccatcgaat ctggccaccg    420
tcatgcgtca attacagatt ctggcctaag aatccacctg aatacaggga ggtgaatgaa   480
gagtatgcag tgcatgtgaa gaagctatcg gagacgttat tagggattct ctcggatgga   540
ttagggttaa agcgtgatgc gttgaaagaa ggtctcggcg gagagatggc ggagtatatg   600
atgaagatta actattatcc gccgtgtcct cggccggatt tagctttagg tgtaccggct   660
catacagatc tcagtggaat cactcttctt gttcctaacg aagttcctgg acttcaagtt   720
ttcaaagatg atcactggtt cgatgcagag tatattccct ccgccgtcat tgttcacatc   780
ggcgatcaga ttctgaggtt gagtaatggg aggtataaaa atgtgttgca taggacgacg   840
gtggataaag agaagacgag gatgtcgtgg ccggttttct tggagcctcc ccgtgaaaag   900
attgttggac ctttaccgga actaaccgga gatgataatc ctccaaagtt taaaccgttt   960
gctttcaagg attacagtta ccgcaagctc aataaacttc ctctggattg a           1011
```

<210> SEQ ID NO 47
<211> LENGTH: 336
<212> TYPE: PRT
<213> ORGANISM: Arabidopsis thaliana

<400> SEQUENCE: 47

```
Met Glu Val Glu Arg Val Gln Asp Ile Ser Ser Ser Leu Leu Thr
  1               5                  10                  15

Glu Ala Ile Pro Leu Glu Phe Ile Arg Ser Glu Lys Glu Gln Pro Ala
             20                  25                  30

Ile Thr Thr Phe Arg Gly Pro Thr Pro Ala Ile Pro Val Val Asp Leu
         35                  40                  45

Ser Asp Pro Asp Glu Glu Ser Val Arg Arg Ala Val Val Lys Ala Ser
     50                  55                  60

Glu Glu Trp Gly Leu Phe Gln Val Val Asn His Gly Ile Pro Thr Glu
 65                  70                  75                  80

Leu Ile Arg Arg Leu Gln Asp Val Gly Arg Lys Phe Phe Glu Leu Pro
                 85                  90                  95

Ser Ser Glu Lys Glu Ser Val Ala Lys Pro Glu Asp Ser Lys Asp Ile
            100                 105                 110

Glu Gly Tyr Gly Thr Lys Leu Gln Lys Asp Pro Glu Gly Lys Lys Ala
        115                 120                 125

Trp Val Asp His Leu Phe His Arg Ile Trp Pro Pro Ser Cys Val Asn
    130                 135                 140

Tyr Arg Phe Trp Pro Lys Asn Pro Pro Glu Tyr Arg Glu Val Asn Glu
145                 150                 155                 160

Glu Tyr Ala Val His Val Lys Lys Leu Ser Glu Thr Leu Leu Gly Ile
                165                 170                 175

Leu Ser Asp Gly Leu Gly Leu Lys Arg Asp Ala Leu Lys Glu Gly Leu
            180                 185                 190
```

-continued

```
Gly Gly Glu Met Ala Glu Tyr Met Met Lys Ile Asn Tyr Tyr Pro Pro
        195             200              205

Cys Pro Arg Pro Asp Leu Ala Leu Gly Val Pro Ala His Thr Asp Leu
    210             215              220

Ser Gly Ile Thr Leu Leu Val Pro Asn Glu Val Pro Gly Leu Gln Val
225             230              235              240

Phe Lys Asp Asp His Trp Phe Asp Ala Glu Tyr Ile Pro Ser Ala Val
            245              250              255

Ile Val His Ile Gly Asp Gln Ile Leu Arg Leu Ser Asn Gly Arg Tyr
            260              265              270

Lys Asn Val Leu His Arg Thr Thr Val Asp Lys Glu Lys Thr Arg Met
        275              280              285

Ser Trp Pro Val Phe Leu Glu Pro Pro Arg Glu Lys Ile Val Gly Pro
    290              295              300

Leu Pro Glu Leu Thr Gly Asp Asp Asn Pro Pro Lys Phe Lys Pro Phe
305             310              315              320

Ala Phe Lys Asp Tyr Ser Tyr Arg Lys Leu Asn Lys Leu Pro Leu Asp
                325             330              335
```

MICROORGANISMS FOR THE RECOMBINANT PRODUCTION OF RESVERATROL AND OTHER FLAVONOIDS

CROSS-RELATED APPLICATIONS

This application claims the benefit of U.S. Provisional Application Ser. No. 60/549,077, filed Mar. 1, 2004.

BACKGROUND

1. Technical Field

The invention relates to methods and materials involved in producing flavonoids and other organic compounds.

2. Background Information

Flavonoids are ubiquitous plant natural products that play a variety of roles in plants, including UV protection, defense against pathogens, and coloration. The uncovering of an increasing number of health benefits associated with flavonoids present in fruits, vegetables, red wine, and green tea resulted in an explosion of research on the medicinal properties of flavonoids during the last few years. Medicinal activities shown for flavonoid compounds range from scavenging of harmful oxygen species, enzyme inhibition, anti-inflammatory and estrogenic activities to cytotoxic antitumor activities.

The recognition of flavonoids as health-promoting nutraceuticals also spurred research on elucidating the complex metabolic networks of flavonoid biosynthesis with the idea of enhancing and altering flavonoid composition in dietary plants. Flavonoids are synthesized from an activated phenylpropanoid starter unit and three malonyl-CoA extender units. Phenylpropanoids are phenolic acids, such as 4-coumaric, caffeic, and ferulic acid, which are used in the formation of lignin, coumarins, and other plant natural products in addition to flavonoids.

SUMMARY

The invention relates to methods and materials involved in producing flavonoids and other organic compounds. A flavonoid compound can be naringenin, eriodictyol, homoeriodictyol, a chalcone, a stilbene, a flavonol, a flavone, an isoflavonoid, a condensed tannin, an isoflavene (e.g., phenoxodiol), a pterocarpan, an anthocyanin pigment, a pyrone, daidzein, genistein, or phloretin. For example, the invention provides nucleic acid molecules, polypeptides, host cells, and methods that can be used to produce flavonoids and other organic compounds. The nucleic acid molecules described herein can be used to engineer host cells having the ability to produce one or more flavonoids or other organic compounds. The polypeptides described herein can be used in cell-free systems to make one or more flavonoids or other organic compounds. The host cells described herein can be used in culture systems to produce large quantities of, for example, flavonoids such as naringenin.

As described herein, exogenously supplied phenylpropionic acids can be readily taken up by cells (e.g., bacterial cells) and converted into other compounds by those cells. Thus, phenylpropionic acids, which can be abundantly available from agricultural waste products, can be used as inexpensive precursors for the production of higher valued flavonoid compounds, for example. In addition, in vivo feeding of exogenous precursor compounds can be used to determine catalytic functions (e.g., activity levels, substrate specificity, etc.) of enzymes such as CoA-ligases and type III polyketide synthases as well as isoenzymes and engineered variants of known enzymes.

In general, the invention features a microorganism having phenol-type CoA-ligase activity and chalcone synthase or stilbene synthase activity, where the microorganism produces a flavonoid compound. The microorganism can contain an exogenous nucleic acid molecule that encodes a polypeptide having the phenol-type CoA-ligase activity. The phenol-type CoA-ligase activity can be coumaroyl-CoA-ligase activity. The microorganism can contain an exogenous nucleic acid molecule that encodes a polypeptide containing the sequence set forth in SEQ ID NO:2. The microorganism can have the chalcone synthase activity. The microorganism can contain an exogenous nucleic acid molecule that encodes a polypeptide having the chalcone synthase activity. The microorganism can contain an exogenous nucleic acid molecule that encodes a polypeptide containing the sequence set forth in SEQ ID NO:4. The microorganism can have the stilbene synthase activity. The microorganism can contain an exogenous nucleic acid molecule that encodes a polypeptide having the stilbene synthase activity. The microorganism can contain an exogenous nucleic acid molecule that encodes a polypeptide containing the sequence set forth in SEQ ID NO:6. The flavonoid compound can be naringenin, eriodictyol, homoeriodictyol, pinocembrin, or phloretin. The microorganism can be a bacterium. The microorganism can be *Escherichia coli, Pseudomonas* species, *Streptomyces* species, or *Bacillus subtilis*. The microorganism can have tyrosine ammonia lyase activity. The microorganism can contain an exogenous nucleic acid molecule that encodes a polypeptide having tyrosine ammonia lyase activity. The microorganism can contain an exogenous nucleic acid molecule that encodes a polypeptide containing the sequence set forth in SEQ ID NO:8. The microorganism can have phenylalanine ammonia lyase activity. The microorganism can contain an exogenous nucleic acid molecule that encodes a polypeptide having phenylalanine ammonia lyase activity. The microorganism can contain an exogenous nucleic acid molecule that encodes a polypeptide containing the sequence set forth in SEQ ID NO:10. The microorganism can have cinnamate hydroxylase activity. The microorganism can contain an exogenous nucleic acid molecule that encodes a polypeptide having cinnamate hydroxylase activity. The microorganism can contain an exogenous nucleic acid molecule that encodes a polypeptide containing the sequence set forth in SEQ ID NO:12. The microorganism can have cytochrome P450 reductase activity. The microorganism can contain an exogenous nucleic acid molecule that encodes a polypeptide having cytochrome P450 reductase activity. The microorganism can contain an exogenous nucleic acid molecule that encodes a polypeptide containing the sequence set forth in SEQ ID NO:14. A culture of the microorganism can produce at least about 10 mg of the flavonoid compound per liter of culture media.

In another aspect, the invention features a method for making a flavonoid compound. The method includes culturing microorganisms under conditions wherein the microorganisms produce the flavonoid compound. The microorganisms have phenol-type CoA-ligase activity and chalcone synthase or stilbene synthase activity such that the flavonoid compound is produced. The microorganisms can contain an exogenous nucleic acid molecule that encodes a polypeptide having the phenol-type CoA-ligase activity. The phenol-type CoA-ligase activity can be coumaroyl-CoA-ligase activity. The microorganisms can contain an exogenous nucleic acid molecule that encodes a polypeptide containing the sequence set forth in SEQ ID NO:2. The microorganisms can have the chalcone synthase activity. The microorganisms can contain an exogenous nucleic acid molecule that encodes a polypeptide having the chalcone synthase activity. The microorganisms can contain an exogenous nucleic acid molecule that encodes a polypeptide containing the sequence set forth in SEQ ID NO:4. The microorganisms can have the stilbene synthase activity. The microorganisms can contain an exogenous nucleic acid molecule that encodes a polypeptide having the stilbene synthase activity. The microorganisms can contain an exogenous nucleic acid molecule that encodes a polypeptide containing the sequence set forth in SEQ ID NO:6. The flavonoid compound can be naringenin, eriodictyol, homoeriodictyol, pinocembrin, or phloretin. The microorganisms can be bacteria. The microorganisms can be *Escherichia coli, Pseudomonas* species, *Streptomyces* species, or *Bacillus subtilis*. The microorganisms can have tyrosine ammonia lyase activity. The microorganisms can contain an exogenous nucleic acid molecule that encodes a polypeptide having tyrosine ammonia lyase activity. The microorganisms can contain an exogenous nucleic acid molecule that encodes a polypeptide containing the sequence set forth in SEQ ID NO:8. The microorganisms can have phenylalanine ammonia lyase activity. The microorganisms can contain an exogenous nucleic acid molecule that encodes a polypeptide having phenylalanine ammonia lyase activity. The microorganisms can contain an exogenous nucleic acid molecule that encodes a polypeptide containing the sequence set forth in SEQ ID NO:10. The microorganisms can have cinnamate hydroxylase activity. The microorganisms can contain an exogenous nucleic acid molecule that encodes a polypeptide having cinnamate hydroxylase activity. The microorganisms can contain an exogenous nucleic acid molecule that encodes a polypeptide containing the sequence set forth in SEQ ID NO:12. The microorganisms can have cytochrome P450 reductase activity. The microorganisms can contain an exogenous nucleic acid molecule that encodes a polypeptide having cytochrome P450 reductase activity. The microorganisms can contain an exogenous nucleic acid molecule that encodes a polypeptide containing the sequence set forth in SEQ ID NO:14. The method can include culturing the microorganisms in the presence of an aromatic acid. The aromatic acid can be 4-coumaric acid, caffeic acid, ferulic acid, phenylpropionic acid, hydroxyphenyl propionic acid, 3-(4-hydroxyphenyl)propionic acid, sinapic acid, or muconic acid. The microorganisms can produce at least about 10 mg of the flavonoid compound per liter. The microorganisms can produce at least about 15 mg of the flavonoid compound per liter. The microorganisms can produce at least about 20 mg of the flavonoid compound per liter.

In another embodiment, the invention features a method for making a chalcone compound. The method includes culturing microorganisms under conditions wherein the microorganisms produce the chalcone compound. The microorganisms have phenol-type CoA-ligase activity and chalcone synthase or stilbene synthase activity such that the chalcone compound is produced. The microorganisms can contain an exogenous nucleic acid molecule that encodes a polypeptide having the phenol-type CoA-ligase activity. The phenol-type CoA-ligase activity can be coumaroyl-CoA-ligase activity. The microorganisms can contain an exogenous nucleic acid molecule that encodes a polypeptide containing the sequence set forth in SEQ ID NO:2. The microorganisms can have the chalcone synthase activity. The microorganisms can contain an exogenous nucleic acid molecule that encodes a polypeptide having the chalcone synthase activity. The microorganisms can contain an exogenous nucleic acid molecule that encodes a polypeptide containing the sequence set forth in SEQ ID NO:4. The microorganisms can have the stilbene synthase activity. The microorganisms can contain an exogenous nucleic acid molecule that encodes a polypeptide having the stilbene synthase activity. The microorganisms can contain an exogenous nucleic acid molecule that encodes a polypeptide containing the sequence set forth in SEQ ID NO:6. The chalcone compound can be phloretin. The microorganisms can be bacteria. The microorganisms can be *Escherichia coli, Pseudomonas* species, *Streptomyces* species, or *Bacillus subtilis*. The method can include culturing the microorganisms in the presence of an aromatic acid. The aromatic acid can be 4-coumaric acid, caffeic acid, ferulic acid, phenylpropionic acid, hydroxyphenyl propionic acid, 3-(4-hydroxyphenyl)propionic acid, sinapic acid, or muconic acid. The microorganisms can produce at least about 10 mg of the chalcone compound per liter.

In another embodiment, the invention features an isolated nucleic acid containing the sequence set forth in SEQ ID NO:42, wherein the nucleic acid encodes a polypeptide having stilbene synthase activity.

In another embodiment, the invention features an isolated nucleic acid encoding a polypeptide containing the sequence set forth in SEQ ID NO:43.

In another embodiment, the invention features a composition containing a compound selected from the group consisting of piceatannol, isorhapontigenin, dihydrokaempferol and dihydroquercetin. Greater than 10 percent (e.g., greater than about 20, 30, 40, 50, 60, 70, 80, 90, 95, or 99 percent) of the composition can be the compound.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is a listing of a nucleic acid sequence that encodes a polypeptide having coumaroyl-CoA-ligase activity (SEQ ID NO:1). This nucleic acid sequence encodes an *A. thaliana* 4-coumaroyl:CoA ligase polypeptide (GenBank Accession Number U18675).

FIG. 4 is a listing of an amino acid sequence of a polypeptide having coumaroyl-CoA-ligase activity (SEQ ID NO:2). The nucleic acid set forth in SEQ ID NO:1 encodes this amino acid sequence.

FIG. 5 is a listing of a nucleic acid sequence that encodes a polypeptide having chalcone synthase activity (SEQ ID NO:3). This nucleic acid sequence encodes an *A. thaliana* chalcone synthase polypeptide (GenBank Accession Number AF112086).

FIG. 6 is a listing of an amino acid sequence of a polypeptide having chalcone synthase activity (SEQ ID NO:4). The nucleic acid set forth in SEQ ID NO:3 encodes this amino acid sequence.

FIG. 7 is a listing of a nucleic acid sequence that encodes a polypeptide having stilbene synthase activity (SEQ ID NO:5). This nucleic acid sequence encodes an *Arachis hypogaea* stilbene synthase polypeptide (GenBank Accession Number AB027606).

FIG. 8 is a listing of an amino acid sequence of a polypeptide having stilbene synthase activity (SEQ ID NO:6). The nucleic acid set forth in SEQ ID NO:5 encodes this amino acid sequence.

FIG. 9 is a listing of a nucleic acid sequence that encodes a polypeptide having tyrosine ammonia lyase activity (SEQ ID NO:7). The start codon was changed from GTG to ATG for translation in *E. coli*. The GenBank sequence (Accession Number ZP_00005404) lists the start codon as GTG for this *Rhodobacter sphaeroides* tyrosine ammonia lyase polypeptide.

FIG. 10 is a listing of an amino acid sequence of a polypeptide having tyrosine ammonia lyase activity (SEQ ID NO:8). The nucleic acid set forth in SEQ ID NO:7 encodes this amino acid sequence.

FIG. 11 is a listing of a nucleic acid sequence that encodes a polypeptide having phenylalanine ammonia lyase activity (SEQ ID NO:9). This nucleic acid sequence encodes an *A. thaliana* phenylalanine ammonia lyase polypeptide (GenBank Accession Number AY303128).

FIG. 12 is a listing of an amino acid sequence of a polypeptide having phenylalanine ammonia lyase activity (SEQ ID NO:10). The nucleic acid set forth in SEQ ID NO:9 encodes this amino acid sequence.

FIG. 13 is a listing of a nucleic acid sequence that encodes a polypeptide having cinnamate hydroxylase activity (SEQ ID NO:11). This nucleic acid sequence encodes an *A. thaliana* cinnamate-4-hydroxylase polypeptide (GenBank Accession Number U71080).

FIG. 14 is a listing of an amino acid sequence of a polypeptide having cinnamate hydroxylase lyase activity (SEQ ID NO:12). The nucleic acid set forth in SEQ ID NO:11 encodes this amino acid sequence.

FIG. 15 is a listing of a nucleic acid sequence that encodes a polypeptide having NADPH-cytochrome p450 reductase activity (SEQ ID NO:13). This nucleic acid sequence encodes an *A. thaliana* NADPH-ferrihemoprotein reductase polypeptide (GenBank Accession Number NM_119167).

FIG. 16 is a listing of an amino acid sequence of a polypeptide having NADPH-cytochrome p450 reductase activity (SEQ ID NO:14). The nucleic acid set forth in SEQ ID NO:13 encodes this amino acid sequence.

FIG. 20 contains graphs plotting growth and naringenin production of recombinant *E. coli* expressing *Rba. sphaeroides* TAL together with *Arabidopsis* 4CL and CHS in TB (A) and modified M9 (B) medium. Filled squares represent growth; circles and triangles represent naringenin production in the culture supernatant and cell pellet, respectively. Data points represent the mean of three independent cultures.

FIG. 22 is a listing of (1) a nucleic acid sequence that encodes a *Medicago truncatula* polypeptide having chalcone synthase activity (SEQ ID NO:15) and (2) an amino acid sequence of a *Medicago truncatula* polypeptide having chalcone synthase activity (SEQ ID NO:16). The CHS1 polypeptide designation used herein refers to the *Medicago truncatula* polypeptide having the amino acid sequence set forth in SEQ ID NO:16.

FIG. 23 is a listing of (1) a nucleic acid sequence that encodes a *Medicago truncatula* polypeptide having chalcone synthase activity (SEQ ID NO:17) and (2) an amino acid sequence of a *Medicago truncatula* polypeptide having chalcone synthase activity (SEQ ID NO:18). The CHS2 polypeptide designation used herein refers to the *Medicago truncatula* polypeptide having the amino acid sequence set forth in SEQ ID NO:18.

FIG. 24 is a listing of (1) a nucleic acid sequence that encodes a *Medicago truncatula* polypeptide having chalcone synthase activity (SEQ ID NO:19) and (2) an amino acid sequence of a *Medicago truncatula* polypeptide having chalcone synthase activity (SEQ ID NO:20). The CHS3 polypeptide designation used herein refers to the *Medicago truncatula* polypeptide having the amino acid sequence set forth in SEQ ID NO:20.

FIG. 25 is a listing of (1) a nucleic acid sequence that encodes a *Medicago truncatula* polypeptide having chalcone synthase activity (SEQ ID NO:21) and (2) an amino acid sequence of a *Medicago truncatula* polypeptide having chalcone synthase activity (SEQ ID NO:22). The CHS4 polypeptide designation used herein refers to the *Medicago truncatula* polypeptide having the amino acid sequence set forth in SEQ ID NO:22.

FIG. 26 is a listing of (1) a nucleic acid sequence that encodes a *Medicago truncatula* polypeptide having chalcone synthase activity (SEQ ID NO:23) and (2) an amino acid sequence of a *Medicago truncatula* polypeptide having chalcone synthase activity (SEQ ID NO:24). The CHS5 polypeptide designation used herein refers to the *Medicago truncatula* polypeptide having the amino acid sequence set forth in SEQ ID NO:24.

FIG. 29 is a listing of (1) a nucleic acid sequence that encodes a *Rheum tataricum* polypeptide having stilbene synthase activity (SEQ ID NO:25) and (2) an amino acid sequence of a *Rheum tataricum* polypeptide having stilbene synthase activity (SEQ ID NO:26).

FIG. 30 is a listing of (1) a nucleic acid sequence that encodes a *Psilotum nudum* polypeptide having stilbene synthase activity (SEQ ID NO:27) and (2) an amino acid sequence of a *Psilotum nudum* polypeptide having stilbene synthase activity (SEQ ID NO:28).

FIG. 31 is a listing of (1) a nucleic acid sequence that encodes a *Vitis vinifera* polypeptide having stilbene synthase activity (SEQ ID NO:29) and (2) an amino acid sequence of a *Vitis vinifera* polypeptide having stilbene synthase activity (SEQ ID NO:30).

FIG. 32 is a listing of (1) a nucleic acid sequence that encodes a *Pseudomonas putida* KT2440 polypeptide having feruloyl-CoA synthase activity (SEQ ID NO:31) and (2) an amino acid sequence of a *Pseudomonas putida* KT2440 polypeptide having feruloyl-CoA synthase activity (SEQ ID NO:32).

FIG. 33 is a listing of (1) a nucleic acid sequence that encodes a *Rhodobacter sphaeroides* polypeptide having p-coumaroyl-CoA ligase activity (SEQ ID NO:33) and (2) an amino acid sequence of a *Rhodobacter sphaeroides* polypeptide having p-coumaroyl-CoA ligase activity (SEQ ID NO:34).

FIG. 34 is a listing of (1) a nucleic acid sequence that encodes a *Streptomyces coelicolor* polypeptide having cinnamate-CoA ligase activity (SEQ ID NO:35) and (2) an amino acid sequence of a *Streptomyces coelicolor* polypeptide having cinnamate-CoA ligase activity (SEQ ID NO:36).

FIG. 35 is a listing of (1) a nucleic acid sequence that encodes an *Arachis hypogaea* polypeptide having stilbene synthase activity (SEQ ID NO:42) and (2) an amino acid sequence of an *Arachis hypogaea* polypeptide having stilbene synthase activity (SEQ ID NO:43).

FIG. 36 is a listing of (1) a nucleic acid sequence that encodes an *A. thaliana* polypeptide having flavanone-3β-hydroxylase activity (SEQ ID NO:44) and (2) an amino acid sequence of an *A. thaliana* polypeptide having flavanone-3β-hydroxylase activity (SEQ ID NO:45).

FIG. 37 is a listing of (1) a nucleic acid sequence that encodes an *A. thaliana* polypeptide having flavonol synthase activity (SEQ ID NO:46) and (2) an amino acid sequence of an *A. thaliana* polypeptide having flavonol synthase activity (SEQ ID NO:47).

DETAILED DESCRIPTION

The invention provides methods and materials related to producing flavonoids (e.g., naringenin, eriodictyol, homoeriodictyol, chalcones, stilbenes, flavonols, flavones, isoflavonoids, condensed tannins, pterocarpans, anthocyanin pigments, pyrones, daidzein, genistein, or phloretin) and/or other organic compounds. For example, the invention provides isolated nucleic acids, polypeptides, host cells, and methods and materials for producing flavonoids such as naringenin or phloretin.

Flavonoids can be synthesized from an activated phenylpropanoid starter unit and three malonyl-CoA extender units. Phenylpropanoids are phenolic acids such as 4-coumaric, caffeic, and ferulic acid (FIG. 1), which are used to form lignin, coumarins, and other plant natural products in addition to flavonoids (Winkel-Shirley, *Plant Physiol*, 126, 485-493 (2001); Weisshaar and Jenkins, *Curr. Opin. Plant Biol.*, 1, 251-257 (1998)); and Paiva, *J. Plant Growth Regul.*, 19, 131-143 (2000)).

A first step in phenylpropanoid biosynthesis can be deamination of L-phenylalanine by a polypeptide having phenylalanine ammonia lyase (PAL) activity to produce trans-cinnamic acid. trans-cinnamic acid can be hydroxylated in the para position of the benzyl ring by a polypeptide having cinnamate hydroxylase lyase (C4H) activity to make 4-coumaric acid, which then can be activated by a polypeptide having coumaroyl-CoA-ligase (4CL) activity to make 4-coumaroyl-CoA. Naringenin chalcone can be synthesized from a single activated 4-coumaroyl-CoA starter unit by sequential addition of three acetate extender units, derived from malonyl-CoA, via a polypeptide having type III polyketide synthase activity such as a polypeptide having chalcone synthase (CHS) activity (Austin and Noel, *Nat. Prod. Rep.*, 20, 79-110 (2003)). Naringenin chalcone then can be converted spontaneously in vitro to the three ringed flavanone structure naringenin, or enzymatically in vivo by a polypeptide having chalcone isomerase (CHI) activity (Mol et al., *Phytochemistry*, 24, 2267-2269 (1985)).

1. Metabolic Pathways

Figure 1:
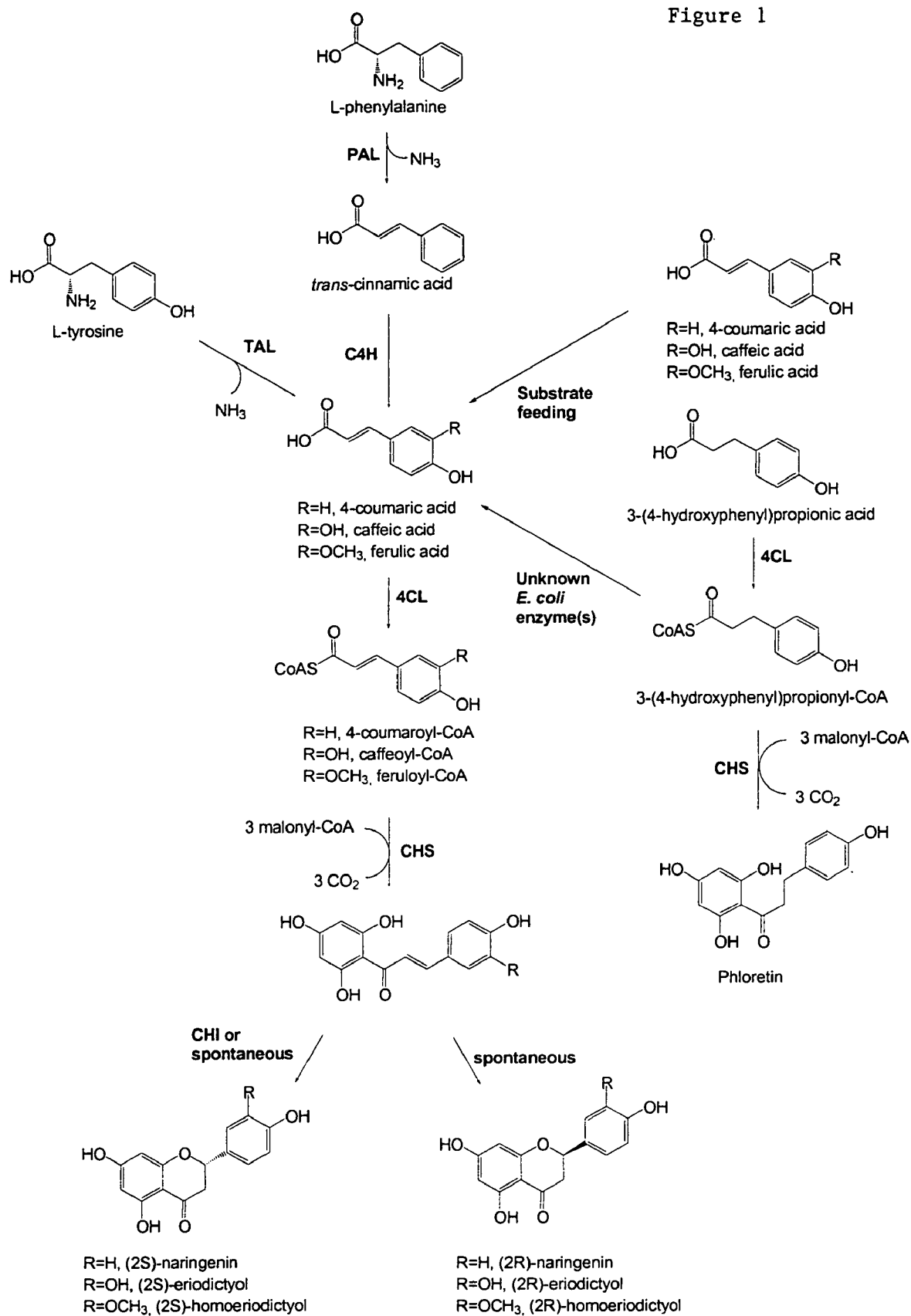
FIG. 1 is a diagram of a pathway for making flavonoids such as naringenin, eriodictyol, and homoeriodictyol.

The invention provides several metabolic pathways that can be used to produce organic compounds (FIGS. 1, 2, 27, and 28). As depicted in FIG. 1, phenylalanine can be converted into trans-cinnamic acid by a polypeptide having PAL activity (e.g., EC 4.3.1.-); the resulting trans-cinnamic acid can be converted into 4-coumaric acid by a polypeptide having C4H activity (e.g., EC 1.14.13.-); the resulting 4-coumaric acid (or added compounds such as 4-coumaric acid, caffeic acid, or ferulic acid) can be converted into 4-coumaroyl-CoA (or other compounds such as caffeoyl-CoA or feruloyl-CoA) by a polypeptide having 4CL activity (e.g., EC 6.2.1.-); and the resulting CoA product (e.g., 4-coumaroyl-CoA, caffeoyl-CoA, or feruloyl-CoA) can be converted into naringenin chalcone (or another product such as eriodictyol chalcone or homoeriodictyol chalcone) by a polypeptide having CHS activity (e.g., EC 2.3.1.- or EC 2.3.1.74). The final form of products such as naringenin (or eriodictyol or homoeriodictyol) can be formed from naringenin chalcone (or eriodictyol chalcone or homoeriodictyol chalcone) spontaneously or by a polypeptide having CHI activity (e.g., EC 5.5.1.6).

In some embodiments, tyrosine can be converted into 4-coumaric acid by a polypeptide having tyrosine ammonia lyase activity (TAL activity; e.g., EC 4.3.1.-). In other embodiments, 4-coumaroyl-CoA (or other compounds such as caffeoyl-CoA or feruloyl-CoA) can be converted into resveratrol (or other compounds such as piceatannol) by a polypeptide having stilbene synthase activity (STS activity; e.g., EC 2.3.1.-, EC 2.3.1.95, or EC 2.3.1.146). In some embodiments, a polypeptide having NADPH-cytochrome p450 reductase activity (e.g., EC 1.6.2.-) can be used. Such polypeptides can be co-expressed with other polypeptides such as polypeptides having C4H activity such that C4H activity is observed.

Polypeptides having PAL activity as well as nucleic acid encoding such polypeptides can be obtained from various species including, without limitation, *Arabidopsis thaliana*, *Medicago truncatula*, and *Arachis hypogaea*. For example, nucleic acid that encodes a polypeptide having PAL activity can be obtained from *Arabidopsis thaliana* and can have a nucleic acid sequence as set forth in SEQ ID NO:9 (FIG. 11), which can encode the amino acid sequence set forth in SEQ ID NO:10 (FIG. 12). In addition, polypeptides having PAL activity as well as nucleic acid encoding such polypeptides can be obtained as described herein.

Polypeptides having C4H activity as well as nucleic acid encoding such polypeptides can be obtained from various species including, without limitation, *Arabidopsis thaliana*, *Medicago truncatula*, and *Arachis hypogaea*. For example, nucleic acid encoding a polypeptide having C4H activity can be obtained from *Arabidopsis thaliana* and can have a nucleic acid sequence as set forth in SEQ ID NO:11 (FIG. 13), which can encode the amino acid sequence set forth in SEQ ID NO:12 (FIG. 14). In addition, polypeptides having C4H activity as well as nucleic acid encoding such polypeptides can be obtained as described herein.

Polypeptides having 4CL activity as well as nucleic acid encoding such polypeptides can be obtained from various species including, without limitation, *Arabidopsis thaliana*, *Medicago truncatula*, and *Arachis hypogaea*. For example, nucleic acid that encodes a polypeptide having 4CL activity can be obtained from *Arabidopsis thaliana* and can have a nucleic acid sequence as set forth in SEQ ID NO:11 (FIG. 3), which can encode the amino acid sequence set forth in SEQ ID NO:2 (FIG. 4). In addition, polypeptides having 4CL activity as well as nucleic acid encoding such polypeptides can be obtained as described herein.

Polypeptides having other types of CoA ligase activity can be used to produce flavonoids or other organic compounds. For example, polypeptides having cinnamate-CoA ligase activity (which can be obtained from *Streptomyces coelicolor* or *S. avermitilis*), polypeptides having feruloyl-CoA ligase activity (which can be obtained from *Pseudomonas* and other genera of lignin degraders), and polypeptides having p-coumaroyl-CoA ligase activity (which can be obtained from *Rhodobacter* and other photoactive yellow protein forming genera) can be used (FIGS. 32-34).

Polypeptides having CHS activity as well as nucleic acid encoding such polypeptides can be obtained from various species including, without limitation, *Arabidopsis thaliana*, *Medicago truncatula*, and *Arachis hypogaea*. For example, nucleic acid that encodes a polypeptide having CHS activity can be obtained from *Arabidopsis thaliana* and can have a sequence as set forth in SEQ ID NO:3 (FIG. 5), which can encode the amino acid sequence set forth in SEQ ID NO:4 (FIG. 6). In addition, polypeptides having CHS activity as well as nucleic acid encoding such polypeptides can be obtained as described herein.

In some embodiments, polypeptides having CHS activity as well as nucleic acid encoding such polypeptides can be obtained from *Medicago truncatula* and can have the amino acid and nucleic acid sequences, respectively, set forth in FIGS. 22, 23, 24, 25, or 26. Other polypeptides having CHS activity (and nucleic acid encoding such polypeptides) that can be used as described herein include, without limitation, those homologous to the polypeptides (and nucleic acids) set forth in FIGS. 6 and 22-26. for example, the CHS1 polypeptide of FIG. 22 is homologous to a polypeptide obtained from *Medicago sativa* (GenBank Accession Number L02904); the CHS2 polypeptide of FIG. 23 is homologous to a polypeptide obtained from *Medicago sativa* (GenBank Accession Number L02902); the CHS3 polypeptide of FIG. 24 is homologous to a polypeptide obtained from *Vitis vinifera* (GenBank Accession Number BAA31259); the CHS4 polypeptide of FIG. 25 is homologous to a polypeptide obtained from *Medicago sativa* (GenBank Accession Number L02905); and the CHS5 polypeptide of FIG. 26 is homologous to a polypeptide obtained from *Pisum sativum* (GenBank Accession Number X80007).

Polypeptides having CHI activity as well as nucleic acid encoding such polypeptides can be obtained from various species including, without limitation, *Arabidopsis thaliana*, *Medicago truncatula*, and *Arachis hypogaea*. For example, nucleic acid that encodes a polypeptide having CHI activity can be obtained from *Arabidopsis thaliana* and can have a sequence as set forth in GenBank accession number M86358, or can be obtained from *Medicago truncatula* and can have a sequence as set forth in GenBank accession number TC85633. In addition, polypeptides having CHI activity as well as nucleic acid encoding such polypeptides can be obtained as described herein.

Polypeptides having TAL activity as well as nucleic acid encoding such polypeptides can be obtained from various species including, without limitation, *Rhodobacter sphaeroides*, *Rhodobacter capsulatus*, and *Halorhodospiro halophila*. For example, nucleic acid that encodes a polypeptide having TAL activity can be obtained from *Rhodobacter sphaeroides* and can have a nucleic acid sequence as set forth in SEQ ID NO:7 (FIG. 9), which can encode the amino acid sequence set forth in SEQ ID NO:8 (FIG. 10). In addition, polypeptides having TAL activity as well as nucleic acid encoding such polypeptides can be obtained as described herein.

Polypeptides having STS activity as well as nucleic acid encoding such polypeptides can be obtained from various species including, without limitation, *Arachis hypogaea*, *Vitis vinifera*, *Rheum tataricum*, *Psilotum nudum*, and *Pinus sylvestris*. For example, nucleic acid that encodes a polypeptide having STS activity can be obtained from *Arachis hypogaea* and can have a nucleic acid sequence as set forth in SEQ ID NO:5 (FIG. 7), which can encode the amino acid sequence set forth in SEQ ID NO:6 (FIG. 8). In addition, polypeptides having STS activity as well as nucleic acid encoding such polypeptides can be obtained as described herein.

Figure 27:
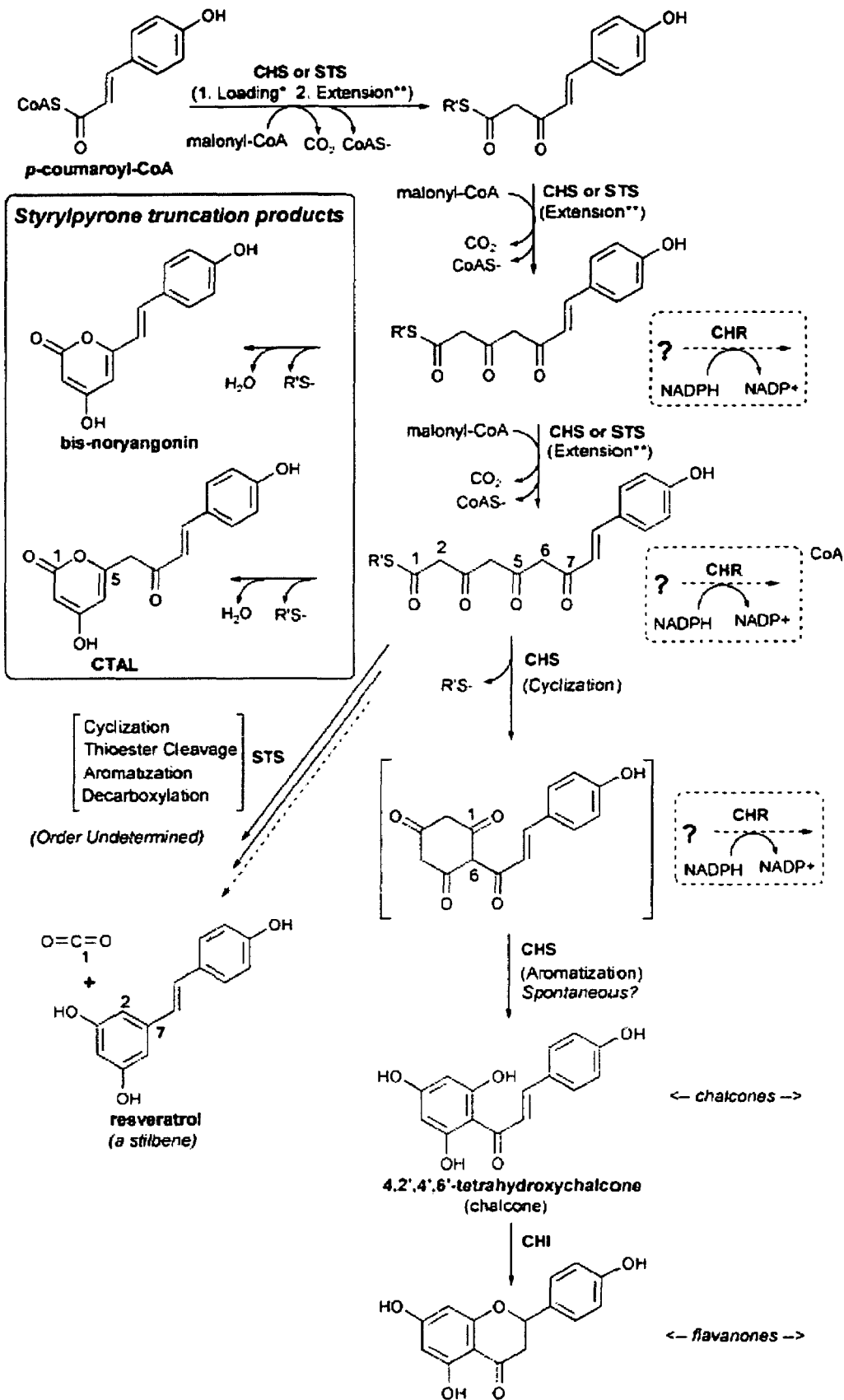
FIG. 27 is a diagram of pathways for making flavonoids such as stilbenes, chalcones, and pyrones.

Polypeptides having STS activity can catalyze the same reaction catalyzed by polypeptides having CHS activity. For example, polypeptides having STS activity can form a linear tetraketide that is cyclized in the active site of the enzyme to the final product. The reactions of STS and CHS polypeptides are identical up to the cyclization reaction, in which case an STS polypeptide can perform an aldol condensation and a CHS polypeptide can perform a Claisen condensation. The final products reflect this difference in cyclization: stilbenes produced by polypeptides having STS activity can have two rings, whereas chalcones produced by polypeptides having CHS activity can have three rings. As shown in FIG. 27, polypeptides having STS or CHS activity can be used to produce organic compounds such as stilbenes, chalcones, and/or pyrones.

Polypeptides having NADPH-cytochrome p450 reductase activity as well as nucleic acid encoding such polypeptides can be obtained from various species including, without limitation, *Arabidopsis thaliana*, *Medicago truncatula*, and *Arachis hypogaea*. For example, nucleic acid that encodes a polypeptide having NADPH-cytochrome p450 reductase activity can be obtained from *Arabidopsis thaliana* and can have a sequence as set forth in SEQ ID NO:13 (FIG. 15), which can encode the amino acid sequence set forth in SEQ ID NO:14 (FIG. 16). In addition, polypeptides having NADPH-cytochrome p450 reductase activity as well as nucleic acid encoding such polypeptides can be obtained as described herein.

The term "polypeptide having enzymatic activity" as used herein refers to any polypeptide that catalyzes a chemical reaction of other substances without itself being destroyed or altered upon completion of the reaction. Typically, a polypeptide having enzymatic activity catalyzes the formation of one or more products from one or more substrates. Such polypeptides can have any type of enzymatic activity including, without limitation, the enzymatic activity or enzymatic activities associated with enzymes such as ligases (e.g., CoA-ligases, coumaroyl-CoA-ligases, benzoyl-CoA-ligases, and fernloyl-CoA-ligases), synthases (e.g., chalcone synthases, and stilbene synthases), lyases (e.g., tyrosine ammonia lyases, histidine ammonia lyases, and phenylalanine ammonia lyases), hydroxylases (e.g., cinnamate hydroxylase, flavanone 3 hydroxylase, and flavonoid 3' 5' hydroxylase), and reductases (e.g., NADPH-cytochrome p450 reductases).

Figure 2:
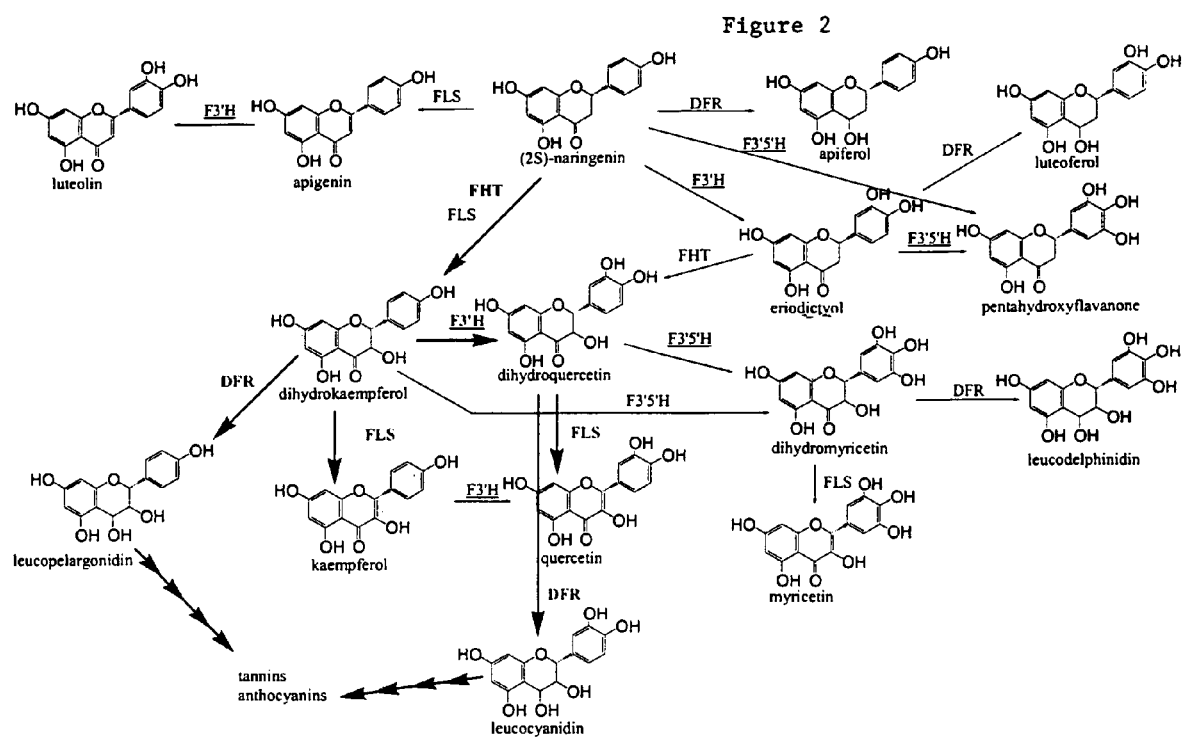
FIG. 2 is a diagram of a pathway for making various flavonoid compounds from naringenin.

As depicted in FIG. 2, naringenin can be converted into various products by polypeptides having the indicated activities. Polypeptides having a particular activity as well as nucleic acid encoding such polypeptides can be obtained as described herein. For example, polypeptides having the indicated enzymatic activity can be obtained from the indicated species and can have a sequence as set forth in the indicated GenBank accession number (Table 1).

hydrogenate acids. In another example, dihydrokaempferol can be dehydrated to form apigenin. Any method can be used to perform a dehydration reaction. For example, dihydrokaempferol can be heated in the presence of a catalyst (e.g., a metal or mineral acid catalyst) to form apigenin.

2. Nucleic Acids

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic

TABLE 1

List of enzymatic activities.

| Abbreviation | Enzymatic activity | Source | Accession number |
|---|---|---|---|
| F3'H | Flavonoid 3'-hydroxylase | *Arabidopsis thaliana* | AH009204 |
| F3'5'H | Flavonoid 3'5'-hydroxylase | *Arabidopsis thaliana* | AAM13084 |
| | | | AAL16143 |
| FLS | Flavonol synthase | *Arabidopsis thaliana* | Q96330 |
| FHT | Flavanone 3β hydroxylase | *Arabidopsis thaliana* | U33932 |
| DFR | Dihydroflavonol-4-reductase | *Arabidopsis thaliana* | NM_123645 |
| LDOX | Leucocyanidin dioxygenase (anthocyanidin synthase ANS) | *Arabidopsis thaliana* | Q96323 |
| BAN | Leucoanthocyanidin reductase | *Arabidopsis thaliana* | Q9SEV0 |
| LAR/IFR homologs | putative IFR-like proteins | *Arabidopsis thaliana* | NP_565107 NP_195634 |
| LAR/IFR homologs | putative IFR-like protein | *Medicago truncatula* | TC77184 TC86142 |
| CHR | Chalcone reductase | *Medicago truncatula* | X82366 |
| IFS | Isoflavone synthase | *Medicago truncatula* | AY167424 |
| IFR | Isoflavone reductase | *Medicago truncatula* | AF277052 |
| VR | Vestitone reductase | *Medicago truncatula* | TC77308 |
| 3-O-UGT homolog | Putative UDP-glucose: flavonoid 3-O-glycosyltransferase | *Arabidopsis thaliana* | T51560 [1] |
| 5-O-UGT homolog | putative UDP-glucose: flavonoid 5-O-glycosyltransferase | *Arabidopsis thaliana* | AAM91686 [2] |
| ATR2 | NADPH-cytochrome P450 reductase | *Arabidopsis thaliana* | X66017 |

[1] most homologous to anthocyanidin/flavonoid 3-O-GT from *Perilla frutescens* (GenBank accession number BAA19659; 46% identity, 62% similarity) and *Vitis vinifera* (GenBank accession number AAB81682; 55% identity, 69% similarity).
[2] most homologous to anthocyanin 5-O-GT from *Perilla frutescens* (GenBank accession number AB013596; 47% identity, 62% similarity).

Each step provided in the pathways depicted in FIGS. 1, 2, 27, and 28 can be performed within a cell or outside a cell (e.g., in a container or column). For example, a microorganism provided herein can be used to perform the steps provided in FIG. 1, or an extract containing polypeptides having the provided enzymatic activities can be used to perform the steps provided in FIG. 1. In addition, chemical treatments can be used to perform the conversions provided in FIGS. 1, 2, 27, and 28. For example, naringenin can be converted into apigenin by reduction.

The organic compounds produced from any of the steps provided in FIGS. 1 and 2 can be chemically converted into other organic compounds. For example, apigenin can be hydrogenated to form naringenin. Hydrogenating an organic acid can be performed using any method such as those used to acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally-occurring can be exogenous to a particular cell. For example, an entire chromosome isolated from a cell of person X is an exogenous nucleic acid with respect to a cell of person Y once that chromosome is introduced into Y's cell.

The invention provides isolated nucleic acids that encode at least two (e.g., at least two, three, four, five, six, seven, eight, nine, ten, or more) of the polypeptides described herein. For example, the invention provides an isolated nucleic acid containing a nucleic acid sequence that encodes the amino acid sequence set forth in SEQ ID NO:2 and a nucleic acid sequence that encodes the amino acid sequence set forth in SEQ ID NO:4. In some embodiments, a nucleic acid can contain nucleic acid sequences that encode between two and ten polypeptides (e.g., between two and five polypeptides, between two and four polypeptides, between three and six polypeptides, or between three and five polypeptides). Each polypeptide can have an activity described herein. For example, each polypeptide can have a ligase (e.g., CoA-ligase, coumaroyl-CoA-ligase, benzoyl-CoA-ligase, and fernloyl-CoA-ligase), synthase (e.g., chalcone synthase and stilbene synthase), lyase (e.g., tyrosine ammonia lyase, histidine ammonia lyase, and phenylalanine ammonia lyase), hydroxylase (e.g., cinnamate hydroxylas, flavanone 3 hydroxylase, and flavonoid 3' 5' hydroxylase), or reductase (e.g., NADPH-cytochrome p450 reductase) activity. In one embodiment, a nucleic acid can contain nucleic acid sequences that encode a polypeptide having 4CL activity and a polypeptide having CHS activity. In another embodiment, a nucleic acid can contain nucleic acid sequences that encode a polypeptide having PAL activity and a polypeptide having C4H activity.

The nucleic acids provided herein can be in the form of an expression vector such that the encoded polypeptide sequences are expressed. For example, nucleic acid sequences having the sequences set forth in SEQ ID NOs:1 and 3 can be inserted into an expression vector such that the polypeptides encoded by sequences set forth in SEQ ID NOs:1 and 3 are expressed when the expression vector is introduced into a cell (e.g., a bacterial, fungal, plant, protozoan, animal, or mammalian cell).

The isolated nucleic acids provided herein can be obtained using any method including, without limitation, common molecular cloning and chemical nucleic acid synthesis techniques. For example, PCR can be used to obtain an isolated nucleic acid containing a nucleic acid sequence sharing similarity to the sequences set forth in SEQ ID NO:1, 3, 5, 7, 9, 11, or 13. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Isolated nucleic acids provided herein also can be obtained by mutagenesis. For example, an isolated nucleic acid containing a sequence set forth in SEQ ID NO:1, 3, 5, 7, 9, 11, or 13 can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain isolated nucleic acids. For example, any nucleic acid sequence having some homology to a sequence set forth in SEQ ID NO:1, 3, 5, 7, 9, 11, or 13, or any amino acid sequence having some homology to a sequence set forth in SEQ ID NO:2, 4, 6, 8, 10, 12, or 14 can be used as a query to search GenBank®.

Further, nucleic acid hybridization techniques can be used to obtain an isolated nucleic acid provided herein. Briefly, any nucleic acid having some homology to a sequence set forth in SEQ ID NO:1, 3, 5, 7, 9, 11, or 13 can be used as a probe to identify a similar nucleic acid by hybridization under conditions of moderate to high stringency. Once identified, the nucleic acid then can be purified, sequenced, and analyzed to determine whether it encodes a polypeptide having an activity described herein.

For the purpose of this invention, moderately stringent hybridization conditions mean the hybridization is performed at about 42° C. in a hybridization solution containing 25 mM KPO$_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about 5×10$^7$ cpm/1 g), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM KPO$_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 65° C. with a wash solution containing 0.2×SSC and 0.1% sodium dodecyl sulfate.

Hybridization can be done by Southern or Northern analysis to identify a DNA or RNA sequence, respectively, that hybridizes to a probe. The probe can be labeled with a biotin, digoxygenin, an enzyme, or a radioisotope such as $^{32}$P The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence set forth in SEQ ID NO:1, 3, 5, 7, 9, 11, or 13 can be used to identify an identical or similar nucleic acid. In addition, probes longer or shorter than 20 nucleotides can be used.

3. Polypeptides

The invention also provides substantially pure polypeptides. The term "substantially pure" as used herein with reference to a polypeptide means the polypeptide is substantially free of other polypeptides, lipids, carbohydrates, and nucleic acid with which it is associated in nature. A substantially pure polypeptide can be at least about 60, 65, 70, 75, 80, 85, 90, 95, or 99 percent pure. Typically, a substantially pure polypeptide will yield a single major band on a polyacrylamide gel.

In one embodiment, the invention provides a substantially pure polypeptide having an amino acid sequence encoded by a nucleic acid provided herein. Such polypeptides include, without limitation, substantially pure polypeptides having one or more of the following activities: a ligase (e.g., CoA-ligase, coumaroyl-CoA-ligase, benzoyl-CoA-ligase, and fernloyl-CoA-ligase), synthase (e.g., chalcone synthase and stilbene synthase), lyase (e.g., tyrosine ammonia lyase, histidine ammonia lyase, and phenylalanine ammonia lyase), hydroxylase (e.g., cinnamate hydroxylas, flavanone 3 hydroxylase, and flavonoid 3' 5' hydroxylase), or reductase (e.g., NADPH-cytochrome p450 reductase) activity.

In another embodiment, the invention provides a composition that contains two or more (e.g., three, four, five, six, seven, eight, nine, ten, or more) substantially pure polypeptide preparations. For example, a composition can contain a substantially pure polypeptide preparation with the polypeptide having the sequence set forth in SEQ ID NO:2 and a substantially pure polypeptide preparation with the polypeptide having the sequence set forth in SEQ ID NO:4. Such compositions can be in the form of a container. For example, two or more substantially pure polypeptide preparations can be located within a column. In some embodiments, the polypeptides can be immobilized on a substrate such as a resin.

Any method can be used to obtain a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, tissue from wild-type or transgenic animals can be used as a source material. In addition, tissue culture cells engineered to over-express a particular polypeptide of interest can be used to obtain a substantially pure polypeptide. Further, a polypeptide within the scope of the invention can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes such as alkaline phosphatase that can aid in the detection of the polypeptide.

4. Genetically Modified Cells

The invention provides genetically modified cells (e.g., cells containing an exogenous nucleic acid molecule). Such cells can be used to produce flavonoids (e.g., naringenin, eriodictyol, and homoeriodictyol) and other organic compounds. In addition, such cells can be from any species including those listed within the taxonomy web pages at the National Center for Biotechnology Information (e.g., at "www" dot "ncbi" dot "nlm" dot "nih" dot "gov"). The cells can be eukaryotic or prokaryotic. For example, genetically modified cells can be mammalian cells (e.g., human, murine, and bovine cells), plant cells (e.g., corn, wheat, rice, and soybean cells), fungal cells (e.g., *Aspergillus* and *Rhizopus* cells), or bacterial cells (e.g., *Escherichia, Bacillus, Streptomyces,* and *Pseudomonas* cells). A cell can be a microorganism. The term "microorganism" as used herein refers to any microscopic organism including, without limitation, bacteria, algae, fungi, and protozoa. Thus, *Escherichia, Bacillus, Streptomyces,* and *Pseudomonas* cells are considered microorganisms and can be used as described herein.

Typically, a cell of the invention is genetically modified such that a particular organic compound is produced. Such cells can contain one or more exogenous nucleic acid molecules that encode polypeptides having enzymatic activity. For example, a microorganism can contain exogenous nucleic acid that encodes a polypeptide having 4CL and CHS activity. In this case, 4-coumaric acid can be converted into 4-coumaroyl-CoA which can be converted into naringenin. It is noted that a cell can be given an exogenous nucleic acid molecule that encodes a polypeptide having an enzymatic activity that catalyzes the production of a compound not normally produced by that cell. Alternatively, a cell can be given an exogenous nucleic acid molecule that encodes a polypeptide having an enzymatic activity that catalyzes the production of a compound that is normally produced by that cell. In this case, the genetically modified cell can produce more of the compound, or can produce the compound more efficiently, than a similar cell not having the genetic modification.

A polypeptide having a particular enzymatic activity can be a polypeptide that is either naturally-occurring or non-naturally-occurring. A naturally-occurring polypeptide is any polypeptide having an amino acid sequence as found in nature, including wild-type and polymorphic polypeptides. Such naturally-occurring polypeptides can be obtained from any species including, without limitation, animal (e.g., mammalian), plant, fungal, and bacterial species. A non-naturally-occurring polypeptide is any polypeptide having an amino acid sequence that is not found in nature. Thus, a non-naturally-occurring polypeptide can be a mutated version of a naturally-occurring polypeptide, or an engineered polypeptide. For example, a non-naturally-occurring polypeptide having CHS activity can be a mutated version of a naturally-occurring polypeptide having CHS activity that retains at least some CHS activity. A polypeptide can be mutated by, for example, sequence additions, deletions, substitutions, or combinations thereof.

The invention provides genetically modified cells that can be used to perform one or more steps of a metabolic pathway described herein. For example, an individual microorganism can contain exogenous nucleic acid such that each of the polypeptides necessary to perform the steps depicted in FIGS. 1, 2, 27, or 28 are expressed. It is important to note that such cells can contain any number of exogenous nucleic acid molecules. For example, a particular cell can contain three exogenous nucleic acid molecules with each one encoding one of the three polypeptides necessary to convert tyrosine into naringenin as depicted in FIG. 1, or a particular cell can endogenously produce polypeptides necessary to convert 4-coumaroyl-CoA into naringenin while containing exogenous nucleic acids that encode polypeptides necessary to convert tyrosine into 4-coumaroyl-CoA.

In addition, a single exogenous nucleic acid molecule can encode one or more than one polypeptide. For example, a single exogenous nucleic acid molecule can contain sequences that encode three different polypeptides. Further, the cells described herein can contain a single copy, or multiple copies (e.g., about 5, 10, 20, 35, 50, 75, 100 or 150 copies), of a particular exogenous nucleic acid molecule. Again, the cells described herein can contain more than one particular exogenous nucleic acid molecule. For example, a particular cell can contain about 50 copies of exogenous nucleic acid molecule X as well as about 75 copies of exogenous nucleic acid molecule Y.

In one embodiment, the invention provides a cell containing an exogenous nucleic acid molecule that encodes a polypeptide having enzymatic activity that leads to the formation of naringenin. It is noted that the produced naringenin can be secreted from the cell, eliminating the need to disrupt cell membranes to retrieve the organic compound. Typically, the cell of the invention produces naringenin with the concentration being at least about 1 mg per L (e.g., at least about 2.5 mg/L, 5 mg/L, 10 mg/L, 20 mg/L, 25 mg/L, 50 mg/L, 75 mg/L, 80 mg/L, 90 mg/L, 100 mg/L, or 120 mg/L). When determining the yield of an organic compound such as naringenin for a particular cell, any method can be used. See, e.g., *Applied Environmental Microbiology* 59(12):4261-4265 (1993).

A nucleic acid molecule encoding a polypeptide having enzymatic activity can be identified and obtained using any method such as those described herein. For example, nucleic acid molecules that encode a polypeptide having enzymatic activity can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known enzymatic polypeptides. Sequence alignment software such as MEGALIGN® (DNASTAR, Madison, Wis., 1997) can be used to compare various sequences. In addition, nucleic acid molecules encoding known enzymatic polypeptides can be mutated using common molecular cloning techniques (e.g., site-directed mutageneses). Possible mutations include, without limitation, deletions, insertions, and base substitutions, as well as combinations of deletions, insertions, and base substitutions. Further, nucleic acid and amino acid databases (e.g., Gen-Bank®) can be used to identify a nucleic acid sequence that encodes a polypeptide having enzymatic activity. Briefly, any amino acid sequence having some homology to a polypeptide having enzymatic activity, or any nucleic acid sequence having some homology to a sequence encoding a polypeptide having enzymatic activity can be used as a query to search GenBank®. The identified polypeptides then can be analyzed to determine whether or not they exhibit enzymatic activity.

In addition, nucleic acid hybridization techniques can be used to identify and obtain a nucleic acid molecule that encodes a polypeptide having enzymatic activity. Briefly, any nucleic acid molecule that encodes a known enzymatic polypeptide, or fragment thereof, can be used as a probe to identify a similar nucleic acid molecules by hybridization under conditions of moderate to high stringency. Such similar nucleic acid molecules then can be isolated, sequenced, and analyzed to determine whether the encoded polypeptide has enzymatic activity.

Expression cloning techniques also can be used to identify and obtain a nucleic acid molecule that encodes a polypeptide having enzymatic activity. For example, a substrate known to interact with a particular enzymatic polypeptide can be used to screen a phage display library containing that enzymatic polypeptide. Phage display libraries can be generated as described elsewhere (Burritt et al., *Anal. Biochem.* 238:1-13 (1990)), or can be obtained from commercial suppliers such as Novagen (Madison, Wis.).

Further, polypeptide sequencing techniques can be used to identify and obtain a nucleic acid molecule that encodes a polypeptide having enzymatic activity. For example, a purified polypeptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid encoding the polypeptide by PCR. Once obtained, the nucleic acid can be sequenced, cloned into an appropriate expression vector, and introduced into a microorganism.

Any method can be used to introduce an exogenous nucleic acid molecule into a cell. In fact, many methods for introducing nucleic acid into microorganisms such as bacteria and yeast are well known to those skilled in the art. For example, heat shock, lipofection, electroporation, conjugation, fusion of protoplasts, and biolistic delivery are common methods for introducing nucleic acid into bacteria and yeast cells. See, e.g., Ito et al., *J. Bacteriol.* 153:163-168 (1983); Durrens et al., *Curr. Genet.* 18:7-12 (1990); and Becker and Guarente, *Methods in Enzymology* 194:182-187 (1991).

An exogenous nucleic acid molecule contained within a particular cell can be maintained within that cell in any form. For example, exogenous nucleic acid molecules can be integrated into the genome of the cell or maintained in an episomal state. In other words, a cell of the invention can be a stable or transient transformant. Again, a microorganism described herein can contain a single copy, or multiple copies (e.g., about 5, 10, 20, 35, 50, 75, 100 or 150 copies), of a particular exogenous nucleic acid molecule as described herein.

Methods for expressing an amino acid sequence from an exogenous nucleic acid molecule are well known to those skilled in the art. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Any type of promoter can be used to express an amino acid sequence from an exogenous nucleic acid molecule. Examples of promoters include, without limitation, constitutive promoters, tissue-specific promoters, and promoters responsive or unresponsive to a particular stimulus (e.g., light, oxygen, chemical concentration, and the like). Moreover, methods for expressing a polypeptide from an exogenous nucleic acid molecule in cells such as bacterial cells and yeast cells are well known to those skilled in the art. For example, nucleic acid constructs that are capable of expressing exogenous polypeptides within E. coli are well known. See, e.g., Sambrook et al., Molecular cloning: a laboratory manual, Cold Spring Harbour Laboratory Press, New York, USA, second edition (1989).

As described herein, a cell can contain an exogenous nucleic acid molecule that encodes a polypeptide having enzymatic activity that leads to the formation of flavonoids (e.g., naringenin, eriodictyol, and homoeriodictyol) and other organic compounds. Methods of identifying cells that contain exogenous nucleic acid are well known to those skilled in the art. Such methods include, without limitation, PCR and nucleic acid hybridization techniques such as Northern and Southern analysis. In some cases, immunohisto-chemistry and biochemical techniques can be used to determine if a cell contains a particular nucleic acid by detecting the expression of the encoded enzymatic polypeptide encoded by that particular nucleic acid molecule. For example, an antibody having specificity for an encoded enzyme can be used to determine whether or not a particular cell contains that encoded enzyme. Further, biochemical techniques can be used to determine if a cell contains a particular nucleic acid molecule encoding an enzymatic polypeptide by detecting an organic product produced as a result of the expression of the enzymatic polypeptide. For example, detection of naringenin after introduction of exogenous nucleic acid that encodes a polypeptide having CHS activity into a cell that does not normally express such a polypeptide can indicate that that cell not only contains the introduced exogenous nucleic acid molecule but also expresses the encoded enzymatic polypeptide from that introduced exogenous nucleic acid molecule. Methods for detecting specific enzymatic activities or the presence of particular organic products are well known to those skilled in the art. For example, the presence of a flavonoid such as naringenin can be determined as described elsewhere for other flavonoids (See, e.g., Chen et al., *J. Chromatography A.*, 913:387-395 (2001); Justesen et al., *J. Chromatography A.*, 799:101-110 (1998); and Hughes et al., *Int. J. Mass Spectrom.*, 210/211:371-385 (2001)).

5. Producing Flavonoids and Other Organic Compounds

The cells described herein can be used to produce flavonoids (e.g., naringenin, eriodictyol, and homoeriodictyol) and other organic compounds. For example, a microorganism can be transfected with nucleic acid that encodes a polypeptide having TAL activity, a polypeptide having 4CL activity, and a polypeptide having CHS activity. Such a microorganism can produce more naringenin or other flavonoids than had the microorganism not been given that nucleic acid. Once transfected, the microorganism can be cultured under conditions optimal for flavonoid production.

In addition, substantially pure polypeptides having enzymatic activity can be used alone or in combination with cells to produce flavonoids or other organic compounds. For example, a preparation containing a substantially pure polypeptide having 4CL activity can be used to catalyze the formation of 4-coumaroyl-CoA. Further, cell-free extracts containing a polypeptide having enzymatic activity can be used alone or in combination with substantially pure polypeptides and/or cells to produce flavonoids or other organic compounds. For example, a cell-free extract containing a polypeptide having 4CL activity can be used to form 4-coumaroyl-CoA, while a microorganism containing a polypeptide having CHS activity can be used to produce naringenin. Any method can be used to produce a cell-free extract. For example, osmotic shock, sonication, and/or a repeated freeze-thaw cycle followed by filtration and/or centrifugation can be used to produce a cell-free extract from intact cells.

It is noted that a cell, substantially pure polypeptide, and/or cell-free extract can be used to produce any flavonoid or other organic compound that is, in turn, treated chemically to produce another compound. For example, a microorganism can be used to produce naringenin, while a chemical process is used to modify naringenin into a derivative such as apigenin or phloretin. Likewise, a chemical process can be used to produce a particular compound that is, in turn, converted into a flavonoid or other organic compound using a cell, substantially pure polypeptide, and/or cell-free extract described herein. For example, a chemical process can be used to produce 4-coumaroyl-CoA, while a microorganism can be used convert 4-coumaroyl-CoA into naringenin.

Typically, naringenin is produced by providing a microorganism and culturing the provided microorganism with culture medium such that naringenin is produced. In general, the culture media and/or culture conditions can be such that the microorganisms grow to an adequate density and produce naringenin efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing appropriate culture medium with, for example, a glucose carbon source is inoculated with a particular microorganism. After inoculation, the microorganisms are incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with glucose, while the second tank contains medium with glycerol.

Once transferred, the microorganisms can be incubated to allow for the production of naringenin. Once produced, any method can be used to isolate the naringenin. For example, common separation techniques can be used to remove the biomass from the broth, and common isolation procedures (e.g., extraction, distillation, and ion-exchange procedures) can be used to obtain the naringenin from the microorganism-free broth. In addition, naringenin can be isolated while it is being produced, or it can be isolated from the broth after the product production phase has been terminated.

Figure 28:
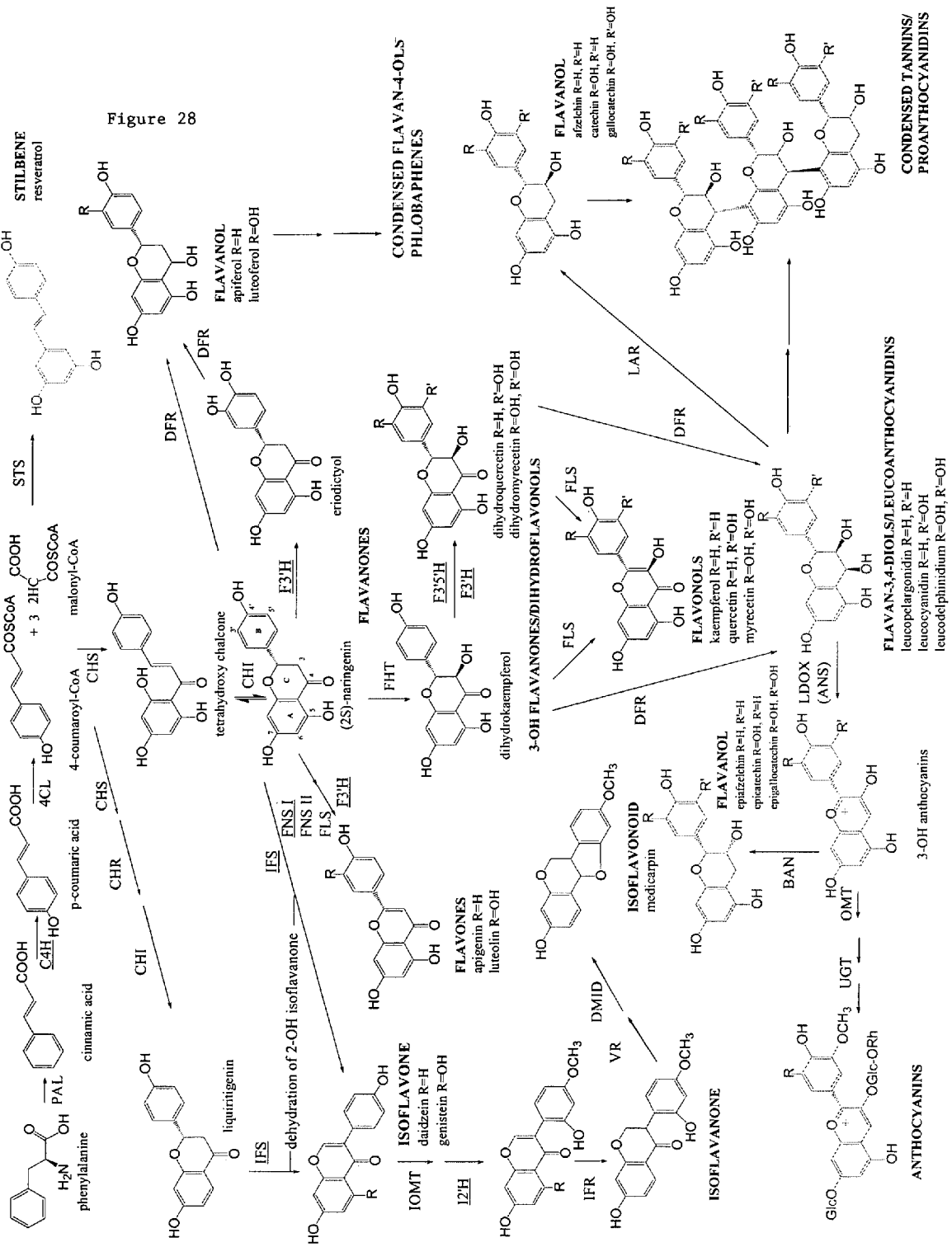
FIG. 28 is a diagram of pathways for making flavonoids.

In some embodiments, naringenin can be converted into another flavonoid such as a flavonoid depicted in FIG. 2 or 28. Once produced, the particular flavonoid can be isolated using common common isolation procedures (e.g., extraction, distillation, and ion-exchange procedures).

The invention will be further described in the following examples, which do not limit the scope of the invention described in the claims.

EXAMPLES

Example 1

Methods and Materials

1. Chemicals

Caffeic acid, ferulic acid, and 3-(4-hydroxyphenyl)-propionic acid were obtained from Sigma Aldrich (St. Louis, Mo.). Naringenin, 4-coumaric acid, phloretin, and arabinose were obtained from ICN (Aurora, Ohio). trans-Cinnamic acid was obtained from Acros Organics (Morris Plains, N.J.). All solvents were of HPLC grade and obtained from Fisher Scientific (Pittsburgh, Pa.). HPLC grade water was obtained from Mallinckrodt Chemicals (Phillipsburg, N.J.). T4 DNA ligase and Vent DNA polymerase were obtained from New England Biolabs (Boston, Mass.). Restriction enzymes were obtained from NEB or Promega (Madison, Wis.), and restriction enzyme buffers (the SuRE/Cut buffers) were obtained from Roche (Indianapolis, Ind.).

2. Strains and Culture Conditions

All cloning and DNA manipulations were carried out in *E. coli* JM109 using standard techniques (Sambrook and Russell, *Molecular Cloning—A Laboratory Manual, Vol.* 3, Third ed., Cold Spring Harbor Laboratory Press, Cold Spring Harbor, N.Y., 2001) and grown at 30° C. with 300 rpm shaking. Following sequencing, plasmids were transformed into *E. coli* strain BW27784 provided by the *E. coli* Genetic Stock Center (New Haven, Conn.), for expression (Table 2; Khlebnikov et al., *Microbiology,* 147, 3241-3247 (2001)).

*Rba. capsulatus* (DSM No. 1710) and *Rba. sphaeroides* (DSM No. 158) were obtained from Deutsche Sammlung von Mikroorganismen und Zellkulturen GmbH (DSMZ, Braunschweig, Germany). *Rba. capsulatus* was grown anaerobically at 30° C. under direct light in modified Van Niel's medium (ATCC medium 1676) for more than 5 days. *Rba. sphaeroides* 158 was grown aerobically at 30° C. in Luria-Bertani (LB) medium for 3 days. Genomic DNA was prepared with Wizard Genomic DNA kit from Promega. *E. coli* harboring either the *Arabidopsis* pathway (pACMod-PAL/C4H+pBADMod2-4CL/CHS) or TAL pathway (pACMod-TAL+pBADMod2-4CL/CHS) was grown in a modified M9, LB, or Terrific broth (TB) medium, supplemented with tetracycline (12.5 mg mL$^{-1}$) or chloramphenicol (50 mg mL$^{-1}$) and carbenicillin or ampicillin (100 mg mL$^{-1}$) to OD$_{600}$=0.4-0.6 and induced with arabinose (0.2% m/v). M9 medium was modified by addition of yeast extract (1.25 g L$^{-1}$) and glycerol (0.5% v/v) into standard M9 medium (Sambrook and Russell, *Molecular Cloning—A Laboratory Manual, Vol.* 3, Third ed., Cold Spring Harbor Laboratory Press, Cold Spring Harbor, N.Y., 2001).

3. Plasmid Construction and Nucleic Acid Cloning pBADMod1 was constructed from pBAD/Thio-TOPO (Invitrogen, Carlsbad, Calif.) by elimination of the NcoI/PmeI fragment using long-range PCR with primers (5'-GGCGCGCCTTAAACAAAATTATTTCTAG-3', SEQ ID NO:37; and 5'-TAATTAAGGTCTCCAGCTTGGCTG-3', SEQ ID NO:38) to introduce unique AscI and PacI sites downstream of the arabinose promoter. pBADMod2 was constructed in the same way by using primers (5'-GGTACCCTC-GAGGTTTAAACAAGCTTCGCTTC-TCTGAGTAG-GAC-3', SEQ ID NO:39; and 5'-CCATGGGCGGCCGCGAATTC-GTCGACCTCT-GAATGGCGGGAG-3', SEQ ID NO:40) to eliminate the arabinose promoter and terminator and introduce a multiple

TABLE 2

Strains and plasmids used.

| Strain or plasmid | Properties or genotype | Source |
|---|---|---|
| Strains | | |
| *E. coli* JM109 | recA1 supE44 endA1 hsdR17 (r$_K^-$m$_K^+$) gyrA96 relA1 thi Δ(lac-proAB)[F'traD36 proAB$^+$ lacI$^q$ lacZΔM15] | 1 |
| *E. coli* BW27784 | lacI$^q$ rrnB3 ΔlacZ4787 hsdR514 Δ(araBAD)567 Δ(rhaBAD)568 Δ (araFGH) Δ ( Δ araEp P$_{CP18}$-araE) | 2 |
| *Rba. capsulatus* 1710 | Type strain | 3 |
| *Rba. sphaeroides* 158 | Type strain | 3 |
| Plasmids | | |
| pUCMod | Cloning vector, constitutive lac promoter, Amp$^r$ | 4 |
| pACMod | Cloning vector, Tet$^r$, Cm$^r$ | 4 |
| pBADMod1 | Cloning vector from pBAD-Thio/TOPO, Amp$^r$ | |
| pBADMod2 | Cloning vector, Amp$^r$ | |
| pBADMod1-PAL | Arabinose inducible PAL from *A. thaliana* | |
| pBADMod1-C4H | Arabinose inducible C4H from *A. thaliana* | |
| pBADMod1-4CL | Arabinose inducible 4CL from *A. thaliana* | |
| pBADMod1-CHS | Arabinose inducible CHS from *A. thaliana* | |
| pACMod-PAL/C4H | Arabinose inducible PAL and C4H, Tet$^r$ | |
| pBADMod2-4CL/CHS | Arabinose inducible 4CL and CHS, Amp$^r$ | |
| pUCMod-TAL | Constitutively expressed TAL from *Rba. sphaeroides* | |
| pACMod-TAL | Constitutively expressed TAL from *Rba. sphaeroides*, Cm$^r$ | |

1: Yanisch-Perron et al., Gene, 33, 103-119 (1985).
2: Khlebnikov et al., Microbiology, 147, 3241-3247 (2001).
3: Obtained from Deutsche Sammlung von Mikroorganismen und Zellkulturen GmbH (DSMZ, Braunschweig, Germany).
4: Schmidt-Dannert et al., Nat. Biotechnol, 18, 750-753 (2000).

cloning site. pUCMod and pACMod have been described elsewhere (Schmidt-Dannert et al., *Nat. Biotechnol.*, 18, 750-753 (2000)).

Nucleic acid sequences encoding a polypeptide having PAL activity (GenBank Accession No. AY303128), a polypeptide having C4H activity (GenBank Accession No. U71080), a polypeptide having 4CL activity (GenBank Accession No. U18675), and a polypeptide having CHS activity (GenBank Accession No. AF112086) were cloned from a pFL61 *Arabidopsis thaliana* cDNA library obtained from the American Type Culture Collection (Manassas, Va., ATCC No. 77500) with forward primers containing a 5' AscI site followed by an optimized Shine-Dalgarno sequence (5'-AGGAGGATTA-CAAAATG-3', SEQ ID NO:41) and the start codon for each gene, followed by an additional 10-15 nucleotides corresponding to the respective gene sequences. Reverse primers contained a PacI site for directional cloning into pBADMod1. PCR was carried out with Vent polymerase, and conditions were as follows: 94° C. for 2 minutes, 30 cycles of 94° C. for 30 seconds, 50° C. for 30 seconds, 72° C. for 1 minute followed by a final extension step at 72° C. for 4 minutes. The nucleic acid sequences encoding a polypeptide having PAL activity and a polypeptide having C4H activity were subcloned, along with the arabinose promoter from pBADMod1, into pACMod using the NcoI and EcoRI sites, respectively, to create pACMod-PAL/C4H. The nucleic acid sequences encoding a polypeptide having 4CL activity and a polypeptide having CHS activity were subcloned in the same way into the NcoI and XhoI sites, respectively, of pBAD-Mod2 to create pBADMod2-4CL/CHS.

Nucleic acid encoding a polypeptide having TAL activity (hypothetical protein listed as GenBank Accession No. ZP_00005404) was cloned from *Rba. sphaeroides* 158 genomic DNA into XbaI/SmaI sites of pUCMod using primers designed as described above with the forward primer providing a Shine-Dalgarno sequence and start codon. PCR conditions were the same as described above except for addition of DMSO (10% v/v) and betaine monohydrate (final concentration 1 M). The nucleic acid encoding a polypeptide having TAL activity was subcloned into the BamHI site of pACMod to create pACMod-TAL.

4. Feeding Experiments

Overnight cultures (5 mL) of *E. coli* transformants harboring pACMod-PAL/C4H+pBADMod2-4CL/CHS, pBAD-Mod2-4CL/CHS, or pBADMod2 alone were inoculated (1:100) into modified M9 medium (50 mL) supplemented with tetracycline and carbenicillin or carbenicillin alone. Cultures were induced with arabinose and supplemented with 4-coumaric acid, trans-cinnamic acid, caffeic acid, ferulic acid, or 3-(4-hydroxyphenyl)propionic acid (5 mg) and allowed to grow for an additional 24 hours before harvest. Additional *E. coli* controls carrying plasmids pBADMod1-4CL or pBADMod1-CHS were tested in the same way as above with 3-(4-hydroxyphenyl)propionic acid.

5. Growth Curves

Overnight cultures (5 mL) of recombinant *E. coli* pAC-Mod-TAL+pBADMod2-4CL/CHS were inoculated 1:200 into modified M9 and TB medium (250 mL) supplemented with chloramphenicol and carbenicillin. Cultures (10 mL) were harvested at induction for the initial production time point and samples (10 mL) were removed at 12, 24, 36, and 48 hours after induction. Samples were centrifuged for 25 minutes at 4000 rpm at 4° C. to remove cells from culture media. Cell pellets were washed once with deionized water and frozen, along with the culture supernatants, at −20° C. prior to extraction.

6. Extraction Conditions

Methanol (5 mL) was added to thawed cell pellets and placed in a sonicating water bath for one hour at 4° C. Cell debris was removed by centrifugation, and methanol was decanted to a fresh conical tube. Water was added to give the final volume (15 mL). The pH of the water/methanol mixture was adjusted (approximately 9.0) to spontaneously convert chalcones to the corresponding flavanones, which aids detection and quantification of products (Mol et al., *Phytochemistry*, 24, 2267-2269 (1985)). The mixture was allowed to sit for one hour at room temperature, followed by two extractions with an equal volume (15 mL) of ethyl acetate. The pooled organic phase was frozen at −80° C. for more than 2 hours, then allowed to warm to room temperature, and residual water was removed. The ethyl acetate was dried under vacuum and resuspended in acetonitrile (100-200 µL).

Culture supernatants (10 mL) were pH adjusted the same as above and incubated at room temperature for one hour and then extracted twice with an equal volume (10 mL) of ethyl acetate. The pooled organic phase was frozen and dried in the same way as above and resuspended in acetonitrile (100 µL). All samples were stored at −20° C. prior to HPLC and MS analysis. Extraction of 4-coumaric acid, 3-(4-hydroxyphenyl)propionic acid, and phloretin were conducted in the same way as above but without adjusting the pH of the culture medium prior to extraction.

7. HPLC Analysis

Pellet and culture supernatant extracts (10 µL) were applied to a Zorbax SB-C18 column (4.6×250 mm, 5 µm; Agilent Technologies, Palo Alto, Calif.) and eluted with an isocratic mobile phase of water:acetonitrile:acetic acid (69.3:30:0.7 flow rate 1 mL min$^{-1}$) using an Agilent 1100 HPLC system equipped with a photodiode array detector. Compound peaks were identified by comparison to retention times and UV/V is spectra of standard compounds. Peak integrations of known amounts of standard to peak areas of unknown were used for quantification.

8. LC/ESI-MS and LC/MS/MS

LC-Mass spectrometry was carried out with a LCQ mass spectrophotometer (Thermo Finnigan, USA) equipped with a Zorbax SB-C18 column under the same elution conditions as HPLC analysis. Mass fragmentation spectra of standard compounds and the extracted compounds were monitored in a mass range of m/z 60-400 with a negative electron spray ionization (ESI) interface (Lee et al., *Chem. Biol.*, 10, 453-462 (2003)). Parent molecular ions were further fragmented by MS/MS analysis using an ESI interface at optimal collision-induced dissociation energy (25-30%). Negative ion values for standard compounds were as follows: 4-coumaric acid (m/z 163.1), trans-cinnamic acid (m/z 146.9), naringenin (m/z 271.1), and phloretin (m/z 273.1).

Example 2

Cloning and Assembly of Naringenin Pathway in *E. coli*

Figure 17:
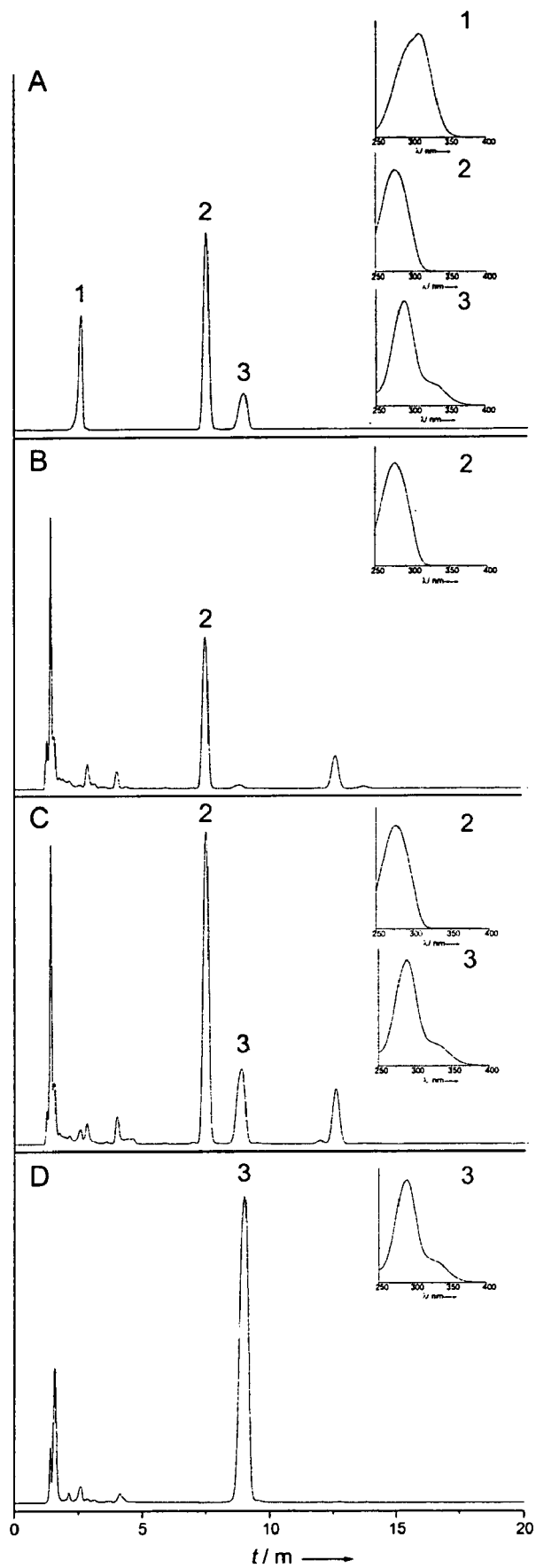
FIG. 17 contains graphs generated from the HPLC analysis of extracts from culture supernatants of *E. coli* cells in modified M9 medium after 24 hours induction. Panel A: Standard compounds, 4-coumaric acid (1), trans-cinnamic acid (2), and naringenin (3). Panel B: *E. coli* pAC-PAL/C4H+pBAD-4CL/CHS. Panel C: *E. coli* pAC-PAL/C4H+pBAD-4CL/CHS fed 4-coumaric acid. Panel D: *E. coli* pBAD-4CL/CHS fed 4-coumaric acid. Absorbance monitored at 290 nm. The insets contain graphs plotting the UV/V is spectra of the indicated compound peaks. The maximum absorbance of 4-coumaric acid, trans-cinnamic acid, and naringenin are 310, 275 and 290 nm, respectively.

Nucleic acid sequences encoding a polypeptide having PAL activity and a polypeptide having C4H activity were cloned into a medium copy number plasmid pACMod (Table 2) under the control of the arabinose promoter (pACMod-PAL/C4H). Nucleic acid sequences encoding a polypeptide having 4CL activity and a polypeptide having CHS activity were cloned onto a high copy number plasmid pBADMod2 (pBADMod2-4CL/CHS) also with the arabinose promoter. This modified pBAD plasmid also contained the arabinose repressor, AraC, to control gene expression from the arabinose promoter (Guzman et al., *J. Bacteriol.*, 177, 4121-4130 (1995)). These two plasmids (pACMod-PAL/C4H+pBAD-Mod2-4CL/CHS) were co-transformed into *E. coli* BW27784, a strain that overexpresses a chromosomal low affinity, high-capacity arabinose permease, AraE (Khlebnikov et al., *Microbiology*, 147, 3241-3247 (2001)). After 24 hours induction, culture supernatants and pellets of cultures grown in modified M9, LB, and TB medium were extracted and analyzed by HPLC. Only trans-cinnamic acid was detected (FIG. 17; panal B) in both culture supernatants and cell pellets, with the majority found in the culture supernatants, indicating a blockage after the first enzymatic step catalyzed by a PAL activity (FIG. 1). When protein expression levels were checked by SDS-PAGE, the recombinant polypeptides were found in both the soluble and insoluble fractions.

These results suggest that a cytochrome P450 monooxygenase is non-functional in *E. coli* since trans-cinnamic acid was not hydroxylated to 4-coumaric acid by the polypeptide having C4H activity. To investigate whether the subsequent polypeptides in the pathway were functional, exogenous 4-coumaric acid was fed at induction to recombinant *E. coli* expressing pACMod-PAL/C4H+pBADMod2-4CL/CHS grown in modified M9 medium. After 24 hours induction, the culture was harvested, and naringenin was detected by HPLC (FIG. 17; panal C) in both the culture supernatant and cell pellet, with the majority found in the culture supernatant. Naringenin was identified by LC-MS/MS (m/z 271.1) and comparison of the obtained fragmentation pattern with that of an authentic standard and literature data (Hughes et al., *Int. J. Mass Spectrom.*, 210-211, 371-385 (2001)). No residual 4-coumaric acid was detected, indicating that 4-coumaric acid can be efficiently transported and metabolized by *E. coli* expressing polypeptides having 4CL and CHS activities. High levels of trans-cinnamic acid were detected due to the functional PAL still present in the assembled four-gene pathway.

To confirm the function of the polypeptide having 4CL activity and the polypeptide having CHS activity in a background devoid of PAL and C4H activities, 4-coumaric acid was fed in the same way to *E. coli* trasfected with only the pBADMod2-4CL/CHS plasmid. The transfected *E. coli* produced naringenin with no detectable trans-cinnamic acid (FIG. 17; panal D) as determined by HPLC and LC-MS. No naringenin was detected in unfed control cultures harboring pBADMod2-4CL/CHS.

Example 3

Feeding of Additional Phenylpropanoid Precursors

Caffeic, ferulic, and 3-(4-hydroxyphenyl)propionic acids were fed to *E. coli* cultures harboring pBADMod2-4CL/CHS to examine the substrate specificities of the polypeptide having 4CL activity and the polypeptide having CHS activity in vivo.

Figure 18:
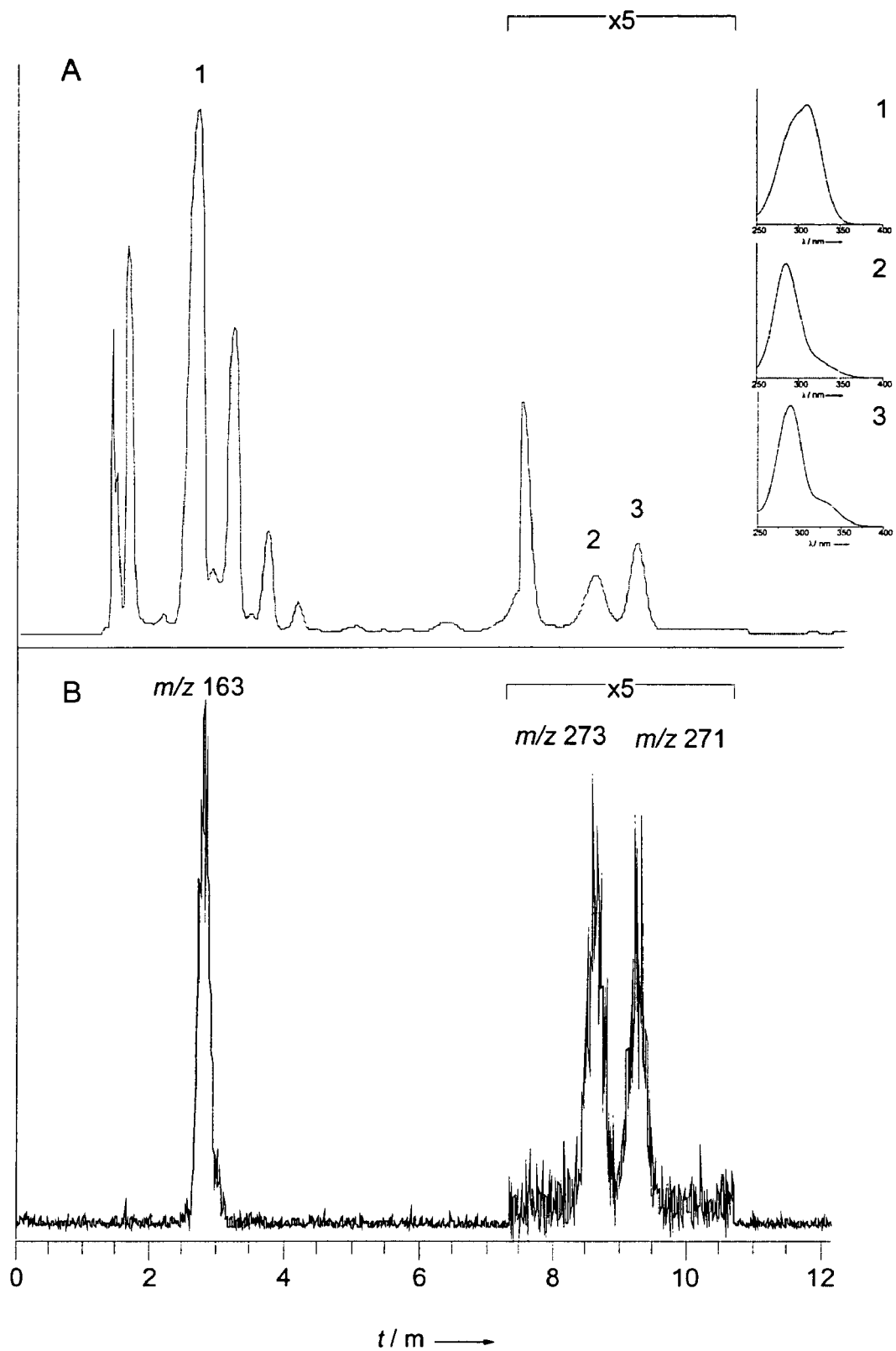
FIG. 18 contains graphs generated from the HPLC analysis of *E. coli* cells fed 3-(4-hydroxyphenyl)propionic acid. Panel A: HPLC chromatogram showing the accumulation of 4-coumaric acid (1) and production of both phloretin (2) and naringenin (3). Panel B: Selective ion chromatogram of the 3-(4-hydroxyphenyl)propionic acid fed culture confirming the masses of 4-coumaric acid, phloretin, and naringenin. Absorbance monitored at 290 nm. The insets contain graphs plotting the UV/V is spectra of the indicated compound peaks. The maximum absorbance of phloretin is 287 nm.

Caffeic and ferulic acids were not converted to the corresponding chalcones or flavanones (eriodictyol and homoeriodictyol, respectively) in modified M9 or TB media as determined by HPLC. Cultures fed with 3-(4-hydroxyphenyl)propionic acid, however, produced both the expected product, phloretin (m/z 273.1), and the 4-coumaric acid product, naringenin (FIG. 1) in equal amounts after 24 hours of cultivation as determined by HPLC and LC-MS analysis. In addition, 4-coumaric acid (m/z 163.0) accumulated to a large extent, with no detectable levels of 3-(4-hydroxyphenyl)propionic acid seen (FIG. 18).

To determine whether phloretin was converted to naringenin by *E. coli* or during the extraction process, phloretin was fed to control cultures containing empty vector (pBADMod2) at induction. After 24 hours, the culture was extracted and found to contain phloretin with no detectable naringenin. Extraction at pH 9.0 and extraction without adjusting the pH were both tested and found to be identical. Next, it was tested whether *E. coli* metabolized 3-(4-hydroxyphenyl)propionic acid into 4-coumaric acid by feeding 3-(4-hydroxyphenyl) propionic acid to control *E. coli* cultures containing empty vector (pBADMod2). After 24 hours, no 4-coumaric acid was detected, and only 3-(4-hydroxyphenyl)propionic acid was found. *E. coli* cultures expressing either the polypeptide having 4CL activity or the polypeptide having CHS activity alone were individually fed with 3-(4-hydroxyphenyl)propionic acid. *E. coli* expressing the polypeptide having 4CL activity alone converted 3-(4-hydroxyphenyl)propionic acid to 4-coumaric acid, indicating that there may be an unknown *E. coli* enzyme that acts on the CoA ester of 3-(4-hydroxyphenyl)propionic acid. With the polypeptide having CHS activity alone, only 3-(4-hydroxyphenyl)propionic acid was detected without any conversion.

Example 4

Cloning and Expression of *Rba. sphaeroides* TAL

Cloning of a recently described polypeptide having TAL activity from *Rhodobacter capsulatus* was attempted (Kyndt et al., *FEBS Lett.*, 512, 240-244 (2002)). The *Rhodobacter* TAL can produce 4-coumaric acid from tyrosine required for the formation of the chromophore of a photoactive yellow protein (Cusanovich and Meyer, *Biochemistry*, 42, 4759-4770 (2003)). Following the procedures described, PCR repeatedly failed to amplify a product of the expected size from genomic DNA.

A BLAST search was conducted using the available *Rba. capsulatus* amino acid sequence of the polypeptide having TAL activity as query. The BLAST search revealed a hypothetical polypeptide (GenBank Accession No. ZP_00005404) from *Rba. sphaeroides* with 51 percent amino acid identity. The nucleic acid sequence encoding this polypeptide was amplified from genomic DNA and cloned into pUCMod to produce pUCMod-TAL for expression under control of a constitutive lac promoter. *E. coli* cells containing pUCMod-TAL were able to produce 4-coumaric acid but not trans-cinnamic acid (the deamination products of tyrosine and phenylalanine, respectively) as determined by HPLC and LC-MS. Production of 4-coumaric acid was highest in TB medium, followed by modified M9 and LB.

Figure 19:
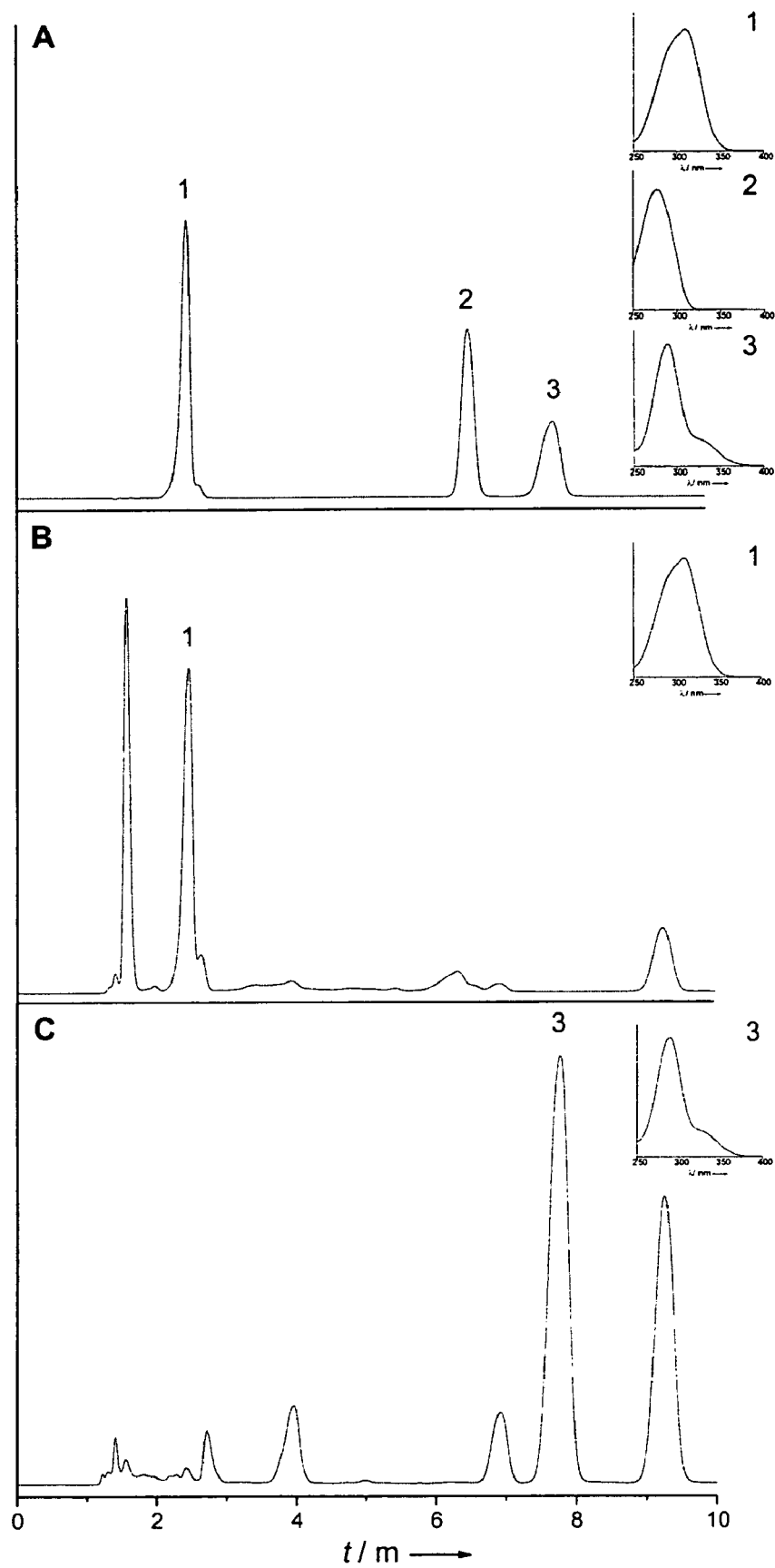
FIG. 19 contains graphs generated from the HPLC analysis of extracts from culture supernatants of *E. coli* transformants expressing *Rhodobacter sphaeroides* TAL alone and together with *Arabidopsis* 4CL and CHS in modified M9 medium after 24 hours induction. Panel A: standard compounds 4-coumaric acid (1), trans-cinnamic acid (2), and naringenin (3). Panel B: *E. coli* pAC-TAL+pBADMod2. Panel C: *E. coli* pAC-TAL+pBAD-4CL/CHS. Absorbance monitored at 290 nm. The insets contain graphs plotting the UV/V is spectra of compound peaks.

The nucleic acid encoding the polypeptide having TAL activity was subcloned into pACMod to allow co-expression in *E. coli* with pBADMod2-4CL/CHS. Transformation of pACMod-TAL into *E. coli* resulted in the production of 4-coumaric acid (2.30 mg L$^{-1}$) in the culture supernatant after 24 hours of cultivation in modified M9 medium (FIG. 19; panal B).

Example 5

Production of Naringenin in *E. coli* with a Three-Gene Hybrid Pathway

To establish a functional hybrid pathway for naringenin production, pACMod-TAL and pBADMod2-4CL/CHS were co-transformed into *E. coli* BW27784. *E. coli* cells expressing this three-gene pathway (TAL+4CL+CHS) were grown in modified M9, LB, and TB medium, and the culture media were extracted after 24 hours of induction. Naringenin was detected in all culture supernatants and cell pellets examined, with the majority found in the culture supernatants (FIG. 19; panal C).

*E. coli* cells expressing the TAL-4CL-CHS hybrid pathway were cultured in modified M9 and TB medium to monitor naringenin production levels during growth. Samples were removed from the cultures 12 hours following induction with arabinose for quantification of naringenin by HPLC. Naringenin production was highest in TB and seen almost exclusively in the culture media, which accounted for more than 90 percent of the total production amount. In TB medium (FIG. 20; panal A), naringenin was not detected at induction, but increased at 12 (1.45 mg $L^{-1}$), 24 (7.65 mg $L^{-1}$), 36 (13.5 mg $L^{-1}$), and 48 hours (20.8 mg $L^{-1}$) after induction. In modified M9 medium (FIG. 20; panal B), naringenin was also not detected at induction, but increased at 12 (0.93 mg $L^{-1}$), 24 (4.89 mg $L^{-1}$), 36 (7.39 mg $L^{-1}$), and 48 hours (7.53 mg $L^{-1}$) after induction. Production in the cell pellet reached a maximum in modified M9 medium 36 hours after induction (0.43 mg $L^{-1}$) and in TB 48 hours after induction (0.73 mg $L^{-1}$), which account for 5.8 percent and 2.9 percent of total production at those times, respectively.

These results indicate that microorganisms transfected with nucleic acid encoding a polypeptide having TAL activity, a polypeptide having 4CL activity, and a polypeptide having CHS activity can produce high levels of naringenin. In addition, these results demonstrate that *E. coli* can produce greater than 20 mg of naringenin per liter, which is a 250-fold increase over another report when no tyrosine is fed into the culture media (Hwang et al., *Appl. Environ. Microbiol.*, 69, 2699-2706 (2003)).

Example 6

Cloning and Expression of Nucleic Acid Encoding a Polypeptide Having NADPH-Cytochrome p450 Reductase Activity Flavonoid pathways contain many cytochrome p450 monooxygenases including polypeptides having C4H activity. Polypeptides having C4H activity can convert trans-cinnamic acid, which can be produced by polypeptides having PAL activity, into 4-coumaric acid. As disclosed in Example 2, an *Arabidopsis thaliana* polypeptide having C4H activity was found to lack function when expressed in *E. coli*.

The following experiment was performed to determine whether expression of a polypeptide having NADPH-cytochrome p450 reductase activity could allow the *A. thaliana* polypeptide having C4H activity to be active in *E. coli*. Nucleic acid encoding an *A. thaliana* NADPH-cytochrome p450 reductase (AtR2) polypeptide was obtained using sequence specific PCR primers in a PCR reaction with an *Arabidopsis* cDNA library obtained from the ATCC. The nucleic acid and amino acid sequences for the AtR2 polypeptide are available on GenBank (GenBank Accession Number NM_119167). The PCR product with the expected size (about 2.2 kb) was purified and digested with XbaI/NotI for cloning into a modified pUC19 plasmid, pUCMod. The nucleic acid was sequenced and found to match the sequence provided in GenBank Accession Number NM_119167.

Figure 21:
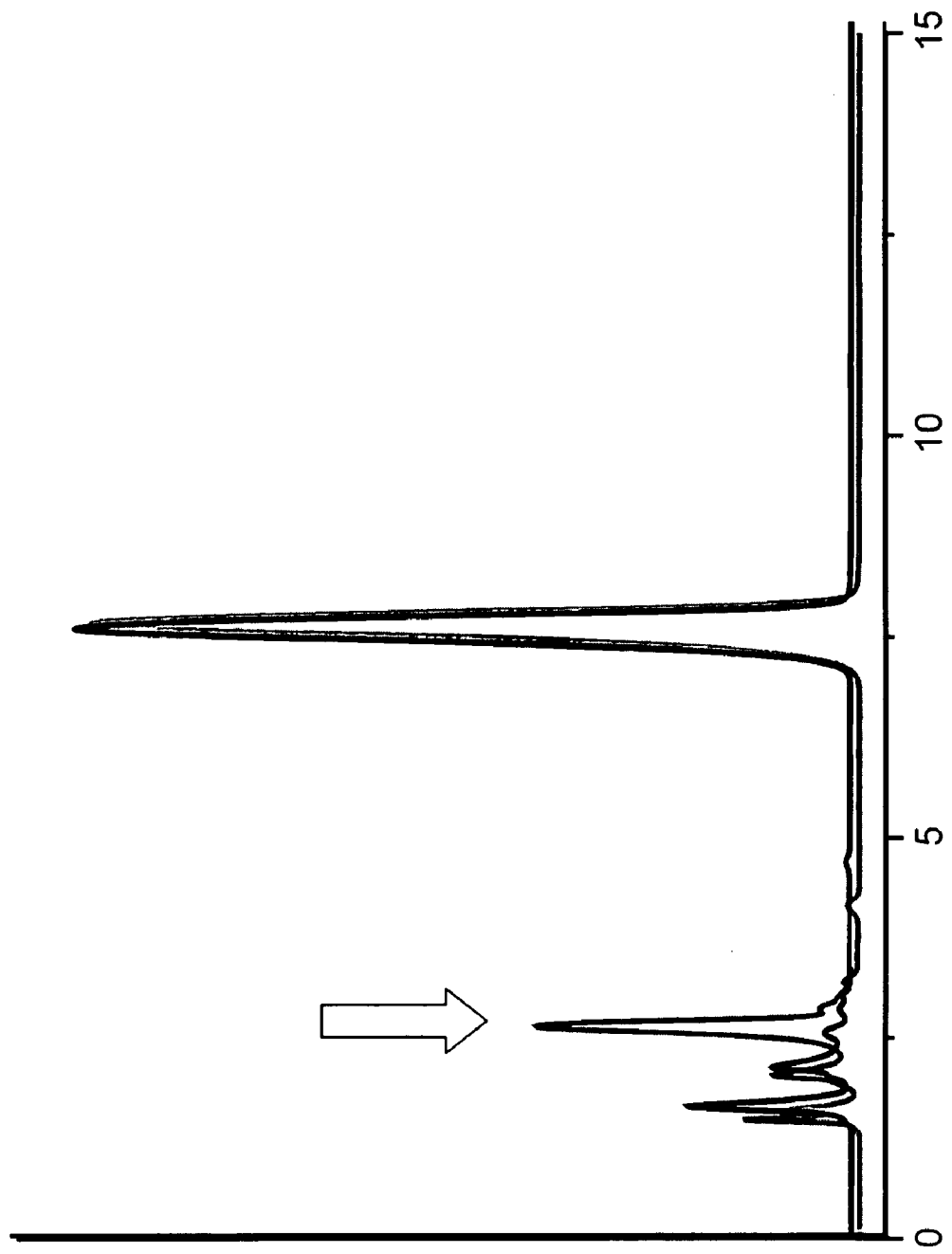
FIG. 21 is an HPLC chromatogram of extracts from culture supernatants of *E. coli* transformants expressing PAL+C4H (dark black) or PAL+C4H+AtR2 (light grey). The peak under the arrow corresponds to 4-coumaric acid.

*E. coli* expressing the polypeptide having PAL activity and the polypeptide having C4H activity (PAL+C4H) were transfected with the nucleic acid encoding the AtR2 polypeptide to produce *E. coli* expressing all three polypeptides (PAL+C4H+AtR2). When cultured as described above, the *E. coli* expressing all three polypeptides (PAL+C4H+AtR2) exhibited C4H activity in vivo (conversion of trans-cinnamic acid into 4-coumaric acid) as determined by HPLC analysis, while *E. coli* lacking expression of the AtR2 polypeptide (PAL+C4H) exhibited no C4H activity (FIG. 21). The large peak to the right of the 4-coumaric acid peak corresponds to trans-cinnamic acid.

To increase the activity and/or expression level of the AtR2 polypeptide, the nucleic acid encoding the AtR2 polypeptide is constructed to encode an AtR2 polypeptide having an N-terminal deletion as described elsewhere (Hull and Celenza, *Prot. Expr. Purif.*, 18, 310-315 (2000)). In addition, other polypeptides can be used with or instead of the AtR2 polypeptide. For example, a polypeptide having isoflavone synthase activity (IFS) can be obtained from *Medicago truncatula*, and uses in conjunction with the AtR2 polypeptide to produce isoflavones in *E. coli*.

Example 7

Cloning and Expression of Nucleic Acid Encoding Polypeptides Having CHS Activity Nucleic acid encoding *Medicago truncatula* polypeptides having chalcone synthase activity were provided by Dr. Deborah Samac's laboratory at the University of Minnesota. The nucleic acid and amino acid sequences are set forth in FIGS. 22-26.

Nucleic acid encoding the CHS5 polypeptide was subcloned into pUCMod behind a constitutive lac promoter for complementation to produce a pUC-CHS5 plasmid. *E. coli* transfected with the pUC-CHS5 plasmid were tested for the ability to use both 4-coumaroyl-CoA and additional CoA thoesters using a substrate feeding experiment. Briefly, the pUC-CHS5 plasmid was introduced into *E. coli* cells containing the plasmid pAC-TAL/4CL or pAC-4CL. The pAC-TAL/4CL and pAC-4CL plasmids contain nucleic acid encoding TAL and 4CL polypeptides or 4CL polypeptide only behind a constitutive lac promoter so that induction with arabinose is not necessary.

With *E. coli* containing pAC-TAL/4CL+pUC-CHS5, the cells were grown for 24 hours, and the culture media was harvested after centrifugation was used to remove the cells. The resulting media was extracted and analyzed. Naringenin was detected. With *E. coli* containing pAC-4CL+pUC-CHS5, the cells were grown to OD 0.4-0.6 and then fed 5.0 mg of either ferulic, caffeic, or 3-(4-hydroxy-phenyl)propionic acid. After an additional 24 hour incubation, the cells were removed, and the media extracted and analyzed. Cells fed 3-(4-hydroxyphenyl)propionic acid produced phloretin, which is similar to the results obtained using the *Arabidopsis* CHS polypeptide. Cells fed caffeic acid produced detectable levels of eriodictyol. These results demonstrate that cells can be engineered to express polypeptides that allow the cells to produce new organic compounds such as flavonoids by feeding the cells particular substrates.

Example 8

Cloning and Expression of Nucleic Acid Encoding Polypeptides Having STS Activity Nucleic acid encoding a polypeptide having STS activity was cloned from peanut (*Arachis hypogaea*). Once cloned, the nucleic acid was sequenced and found to be different from the sequence provided in GenBank accession number AB027606 (FIG. 35). In particular, there were nine amino acid differences.

E. coli designed to express the nucleic acid encoding a polypeptide having STS activity as well as nucleic acid encoding Rhodobacter sphaeroides TAL and A. thaliana 4CL produced a stilbene compound, resveratrol. This compound was extracted from the E. coli growth media in the same manner as described herein for naringenin. Briefly, cells were removed by centrifugation after about 24 hours of growth. The liquid media was decanted to a fresh tube and extracted with ethyl acetate. The pH of the liquid media optionally can be adjusted with hydrochloric acid prior to extraction to increase yield.

In addition, an in vivo feeding technique was used to produce several flavonoid compounds. This technique was similar to those described herein except that instead of adding a 5 mg quantity of a substrate (e.g., 4-coumaric acid) directly to a growing E. coli culture, a quantity of substrate was added in a small volume of DMSO or any possible solvent (e.g., methanol, ethanol, water, etc.) to make a concentrate in the solvent. This concentrate was then diluted to a working concentration in the culture. For example, a 1 molar solution of 4-coumaric acid was made in DMSO and then diluted to 1 mM for the final concentration in the growing culture.

In one experiment, resveratrol was produced by and obtained from E. coli cultures that (1) were designed to express a polypeptide having 4CL activity and a polypeptide having STS activity and (2) were fed 4-coumaric acid. The production of additional stilbene compounds, piceatannol and isorhapontigenin, was also observed via feeding the E. coli cultures caffeic and ferulic acids, respectively. Each of these stilbene compounds were extracted in a manner similar to those described herein.

Example 9

Cloning and Expression of Nucleic Acid Encoding Polypeptides Having FHT and FLS Activity Nucleic acid encoding a polypeptide having FHT activity was cloned from A. thaliana (FIG. 36). In addition, nucleic acid encoding a polypeptide having FLS activity was cloned from A. thaliana (FIG. 37). When the nucleic acid encoding a polypeptide having FHT activity was expressed in E. coli, the dihydroflavonol class of compounds were produced after using the in vivo feeding technique described herein to feed flavanones such as naringenin, eriodictyol, etc. as substrates. In particular, dihydrokaempferol was produced from E. coli expressing FHT that had been fed naringenin, while dihydroquercetin was produced when the E. coli were fed eriodictyol. The dihydroflavonols were extracted from the liquid media as described herein for other flavonoid classes and were readily detected on HPLC.

Flavonols were produced by co-expressing FHT and FLS in conjunction with feeding of flavanone (e.g., naringenin, eriodictyol, etc.) substrates. In particular, kaempferol was produced by E. coli that had been fed naringenin and that expressed both FHT and FLS polypeptides. Quercetin was produced by E. coli that had been fed eriodictyol and that expressed both FHT and FLS polypeptides. Small quantities of these flavonols were purified by extraction from the liquid media, but the vast majority was purified from the materials that were pelleted with the cells since the flavonols appeared water insolubility. Briefly, after centrifugation and decanting the media, a small amount of water (e.g., 50-150 µL) was added, and the cell material removed. The steps of centrifugation, water addition, and cell material removal were repeated several times. The flavonols can be purified away from the cell pellet using other methods such as solid phase extraction or gel filtration chromatography.

In addition, both dihydroflavonols and flavonols can be produced by (1) co-expressing 4CL and CHS along with FHT or FHT and FLS, and (2) in vivo feeding of phenylpropionic acids (e.g., 4-coumaric acid, caffeic acid, etc.) to produce the corresponding dihydroflavonol or flavonol. For example, E. coli expressing 4CL, CHS, and FHT, that are fed 4-couomaric acid, can produce dihydrokaempferol. Inclusion of FLS to that pathway can produce kaempferol.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An *E. coli* microorganism comprising an exogenous nucleic acid encoding a naturally occurring polypeptide having coumaroyl-CoA-ligase activity and an exogenous nucleic acid encoding a naturally occurring polypeptide having stilbene synthase activity, wherein the polypeptide having coumaroyl-CoA-ligase activity is a plant polypeptide, a *Streptomyces* polypeptide, a *Pseudomonas* polypeptide, or a *Rhodobacter* polypeptide, wherein the polypeptide having stilbene synthase activity is an *Arachis hypogaea* polypeptide, a *Vitis vinifera* polypeptide, a *Rheum tataricum* polypeptide, a *Psilotum nudum* polypeptide, or a *Pinus sylvestris* polypeptide, and wherein a culture comprising a plurality of said microorganisms produces and secretes at least 20 mg/L of a flavonoid compound.

2. The microorganism of claim 1, wherein said polypeptide having coumaroyl-CoA-ligase activity comprises the sequence set forth in SEQ ID NO:2.

3. The microorganism of claim 1, wherein said polypeptide having stilbene synthase activity comprises the sequence set forth in SEQ ID NO:6.

4. The microorganism of claim 1, wherein said flavonoid compound is resveratrol or piceatannol.

5. The microorganism of claim 1, wherein said microorganism further comprises an exogenous nucleic acid that encodes a polypeptide having tyrosine ammonia lyase activity, wherein said polypeptide is a *Rhodobacter capsulatus* or *Rhodobacter sphaeroides* polypeptide.

6. The microorganism of claim 1, wherein said microorganism further comprises an exogenous nucleic acid that encodes a tyrosine ammonia lyase polypeptide comprising the sequence set forth in SEQ ID NO:8.

7. The microorganism of claim 1, wherein an expression vector comprises said exogenous nucleic acid encoding said polypeptide having coumaroyl-CoA-ligase activity and said exogenous nucleic acid encoding said polypeptide having stilbene synthase activity.

8. A method of producing resveratrol, said method comprising culturing said microorganism of claim 1 in the presence of 4-coumaric acid.

9. An *E. coli* microorganism comprising an exogenous nucleic acid encoding a polypeptide having coumaroyl-CoA-ligase activity, wherein said polypeptide having coumaroyl-CoA-ligase activity is an *Arabidopsis thaliana, Medicago truncatula, Arachis hypogaea, Streptomyces coelicolor, Streptomyces avermitilis, Pseudomonas* spp. or *Rhodobacter* spp. polypeptide, and an exogenous nucleic acid encoding a polypeptide having stilbene synthase activity, wherein said polypeptide having stilbene synthase activity is an *Arachis hypogaea, Vitis vinifera, Rheum tataricum, Psilotum nudum*, or *Pinus sylvestris* polypeptide, and wherein a culture comprising a plurality of said microorganisms produces and secretes at least 20 mg/L of resveratrol.

10. The *E. coli* microorganism of claim 9, wherein said microorganism further comprises an exogenous nucleic acid that encodes a polypeptide having tyrosine ammonia lyase activity, wherein said polypeptide having tyrosine ammonia lyase activity is a *Rhodobacter capsulatus* or *Rhodobacter sphaeroides* polypeptide.

11. An *E. coli* microorganism comprising exogenous nucleic acids encoding polypeptides having phenol-type CoA-ligase activity and stilbene synthase activity, wherein said polypeptide having phenol-type CoA-ligase activity comprises the sequence set forth in SEQ ID NO:2, wherein said polypeptide having stilbene synthase activity comprises the sequence set forth in SEQ ID NO:6, and wherein said microorganism produces and secretes a flavonoid compound.

12. The microorganism of claim 11, wherein said microorganism further comprises an exogenous nucleic acid that encodes a tyrosine ammonia lyase polypeptide comprising the sequence set forth in SEQ ID NO:8.

13. An *E. coli* microorganism comprising an exogenous nucleic acid encoding a naturally occurring polypeptide having coumaroyl-CoA-ligase activity, an exogenous nucleic acid encoding a naturally occurring polypeptide having stilbene synthase activity, and an exogenous nucleic acid encoding a naturally occurring polypeptide having tyrosine ammonia lyase activity, wherein the polypeptide having coumaroyl-CoA-ligase activity is a plant polypeptide, a *Streptomyces* polypeptide, a *Pseudomonas* polypeptide, or a *Rhodobacter* polypeptide, wherein the polypeptide having stilbene synthase activity is an *Arachis hypogaea* polypeptide, a *Vitis vinifera* polypeptide, a *Rheum tataricum* polypeptide, a *Psilotum nudum* polypeptide, or a *Pinus sylvestris* polypeptide, wherein the polypeptide having tyrosine ammonia lyase activity is a *Rhodobacter capsulatus* or *Rhodobacter sphaeroides* polypeptide, and wherein a culture comprising a plurality of said microorganisms produces and secretes at least 20 mg/L of resveratrol.

14. The microorganism of claim 13, wherein an expression vector comprises said exogenous nucleic acid encoding said polypeptide having coumaroyl-CoA-ligase activity, said exogenous nucleic acid encoding said polypeptide having stilbene synthase activity, and said exogenous nucleic acid encoding said polypeptide having tyrosine ammonia lyase activity.

15. A method of producing resveratrol, said method comprising culturing said microorganism of claim 13 under conditions wherein said microorganism produces resveratrol.

\* \* \* \* \*

UNITED STATES PATENT AND TRADEMARK OFFICE
CERTIFICATE OF CORRECTION

PATENT NO. : 7,604,968 B2  
APPLICATION NO. : 11/069633  
DATED : October 20, 2009  
INVENTOR(S) : Schmidt-Dannert et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 245 days.

Signed and Sealed this

Fifth Day of October, 2010

David J. Kappos  
*Director of the United States Patent and Trademark Office*